(12) United States Patent
Sherman et al.

(10) Patent No.: US 11,253,858 B2
(45) Date of Patent: Feb. 22, 2022

(54) SYSTEMS AND METHODS FOR OPTICALLY PROCESSING SAMPLES

(71) Applicant: Bioelectronica Corporation, Reno, NV (US)

(72) Inventors: Leonard Sherman, Los Altos Hills, CA (US); Roger Chen, Saratoga, CA (US); Jonathan F. Hull, Reno, NV (US)

(73) Assignee: Bioelectronica Corporation, Reno, NV (US)

( * ) Notice: Subject to any disclaimer, the term of this patent is extended or adjusted under 35 U.S.C. 154(b) by 103 days.

(21) Appl. No.: 16/803,783

(22) Filed: Feb. 27, 2020

(65) Prior Publication Data
US 2020/0200729 A1 Jun. 25, 2020

Related U.S. Application Data

(63) Continuation of application No. 16/596,688, filed on Oct. 8, 2019.
(Continued)

(51) Int. Cl.
*B01L 3/00* (2006.01)
*G01N 15/14* (2006.01)
(Continued)

(52) U.S. Cl.
CPC .... *B01L 3/502761* (2013.01); *G01N 15/0205* (2013.01); *G01N 15/1404* (2013.01); *G01N 15/1475* (2013.01); *G01N 33/4833* (2013.01); *B01L 2200/0652* (2013.01); *B01L 2200/143* (2013.01); *B01L 2300/0663* (2013.01); *B01L 2400/0415* (2013.01);
(Continued)

(58) Field of Classification Search
CPC ....... B01L 2200/0652; B01L 2200/143; B01L 2300/0663; B01L 2400/0415; B01L 3/502761; G01N 15/0205; G01N 15/14; G01N 15/1404; G01N 15/1475; G01N 2015/0277; G01N 2015/1006; G01N 2015/1422; G01N 2015/149; G01N 21/33; G01N 21/64; G01N 33/483; G01N 33/4833
See application file for complete search history.

(56) References Cited

U.S. PATENT DOCUMENTS 5,534,441 A 7/1996 Miyazaki et al.
5,681,752 A 10/1997 Prather
(Continued)

OTHER PUBLICATIONS

Bishara, W. et al. (2010). "Lensfree on-chip microscopy over a wide field-of-view using pixel super-resolution," Optics Express 18:11181-11191.
(Continued)

*Primary Examiner* — Jennifer Wecker
(74) *Attorney, Agent, or Firm* — Cooley LLP

(57) ABSTRACT

A system for processing a sample includes a chamber having at least one inlet and at least one outlet, where the chamber is configured to accommodate flow of the sample from the at least one inlet toward the at least one outlet, and an imager array configured to image the flow of the sample in the chamber, where the imager array includes at least one lensless image sensor configurable opposite at least one light source.

10 Claims, 54 Drawing Sheets

Related U.S. Application Data

(60) Provisional application No. 62/859,666, filed on Jun. 10, 2019, provisional application No. 62/800,385, filed on Feb. 1, 2019, provisional application No. 62/742,833, filed on Oct. 8, 2018.

(51) Int. Cl.
    *G01N 15/02*      (2006.01)
    *G01N 33/483*      (2006.01)
    *G01N 15/10*      (2006.01)

(52) U.S. Cl.
    CPC ........... *G01N 2015/0277* (2013.01); *G01N 2015/1006* (2013.01); *G01N 2015/149* (2013.01); *G01N 2015/1422* (2013.01)

(56) References Cited

U.S. PATENT DOCUMENTS

| | | | |
|---|---|---|---|
| 7,635,420 | B1 | 12/2009 | Li et al. |
| 8,349,276 | B2 | 1/2013 | Pamula et al. |
| 8,866,063 | B2 | 10/2014 | Ozcan et al. |
| 8,974,652 | B2 | 3/2015 | Gascoyne et al. |
| 9,605,941 | B2 | 3/2017 | Ozcan et al. |
| 10,088,664 | B2 | 10/2018 | Morel et al. |
| 2002/0081014 | A1 | 6/2002 | Ravkin |
| 2002/0107131 | A1 | 8/2002 | Jorgensen et al. |
| 2003/0178310 | A1 | 9/2003 | Gawad et al. |
| 2005/0128479 | A1 | 6/2005 | Gilbert et al. |
| 2006/0037187 | A1 | 2/2006 | Sparks et al. |
| 2006/0038120 | A1 | 2/2006 | Lean et al. |
| 2008/0276690 | A1 | 11/2008 | Gupta et al. |
| 2009/0068170 | A1* | 3/2009 | Weitz ............ G01N 33/5052 424/130.1 |
| 2009/0131269 | A1 | 5/2009 | Martin et al. |
| 2012/0061584 | A1 | 3/2012 | Trinkle et al. |
| 2012/0140223 | A1 | 6/2012 | Mitchell et al. |
| 2012/0142032 | A1 | 6/2012 | Morgan et al. |
| 2012/0218379 | A1 | 8/2012 | Ozcan et al. |
| 2012/0264114 | A1 | 10/2012 | Wacogne et al. |
| 2013/0028812 | A1 | 1/2013 | Prieto et al. |
| 2013/0189794 | A1 | 7/2013 | Emeric et al. |
| 2015/0004627 | A1 | 1/2015 | Wu et al. |
| 2015/0081258 | A1 | 3/2015 | Calderon et al. |
| 2016/0153959 | A1 | 6/2016 | Vojnovic et al. |
| 2017/0220000 | A1 | 8/2017 | Ozcan et al. |
| 2018/0045634 | A1 | 2/2018 | Bachalo et al. |
| 2018/0056288 | A1* | 3/2018 | Abate ............ G01N 15/1484 |
| 2018/0333724 | A1 | 11/2018 | Hull et al. |

OTHER PUBLICATIONS

Cui, X. et al. (2008). "Lensless high-resolution on-chip optofluidic microscopes for *Caenorhabditis elegans* and cell imaging," PNAS 105:10670-10675.

Greenbaum, A. et al. (2012). "Imaging without lenses: Achievements and remaining challenges of wide-field on-chip microscopy," Nature Methods 9:889-895.

Hadwen, B. et al. (2012). "Programmable large area digital microfluidic array with integrated droplet sensing for bioassays," Lab Chip 12:3305-3313.

International Search Report dated Oct. 4, 2018, for PCT Application No. PCT/US2018/033955, filed on May 22, 2018, 4 pages.

International Search Report dated Feb. 14, 2020, for PCT Application No. PCT/US2019/055268, filed on Oct. 8, 2019, 4 pages.

International Search Report dated Feb. 24, 2020, for PCT Application No. PCT/US2019/057442, filed on Oct. 22, 2019, 4 pages.

Kemna, E.W.M. et al. (2013). "Label-free, high-throughput, electrical detection of cells in droplets," Analyst 138:4585-4592.

Lee, S.A. et al. (2011). "Color capable sub-pixel resolving optofluidic microscope and its application to blood cell imaging for malaria diagnosis," PLoS One 6:e26127, 6 total pages.

Lee, J. et al. (2014). "CMOS image sensor-based ELISA detector using lens-free shadow imaging platform," Sensors and Actuators 196:511-517.

Pang, S. et al. (2009). "Implementation of a color-capable optofluidic microsope on a RGB CMOS color sensor chip substrate," Lab Chip 10:411-414.

Rethore, E et al. (2011). "Digital volume correlation analyses of synchrotron tomographic images," In: The Journal of Strain Analysis for Engineering Design 46:683-695.

Shih, S.C.C. et al. (2013). "Digital microfluidics with impedance sensing for integrated cell culture and analysis," Biosensors and Bioelectronics 42:314-320.

Silicon Biosystems Menarini (2017). Home Page, located at http://www.siliconbiosystems.com/, 2 total pages.

Written Opinion of the International Searching Authority dated Oct. 4, 2018, for PCT Application No. PCT/US2018/033955, filed on May 22, 2018, 9 pages.

Written Opinion of the International Searching Authority dated Feb. 14, 2020, for PCT Application No. PCT/US2019/055268, filed on Oct. 8, 2019, 8 pages.

Written Opinion of the International Searching Authority dated Feb. 24, 2020, for PCT Application No. PCT/US2019/057442, filed on Oct. 22, 2019, 6 pages.

Zheng, G. et al. (2011). "The ePetri dish, an on-chip cell imaging platform based on subpixel perspective sweeping microscopy (SPSM)," PNAS 108:16889-16894.

U.S. Appl. No. 16/596,688, filed Oct. 8, 2019, by Sherman et al.

\* cited by examiner

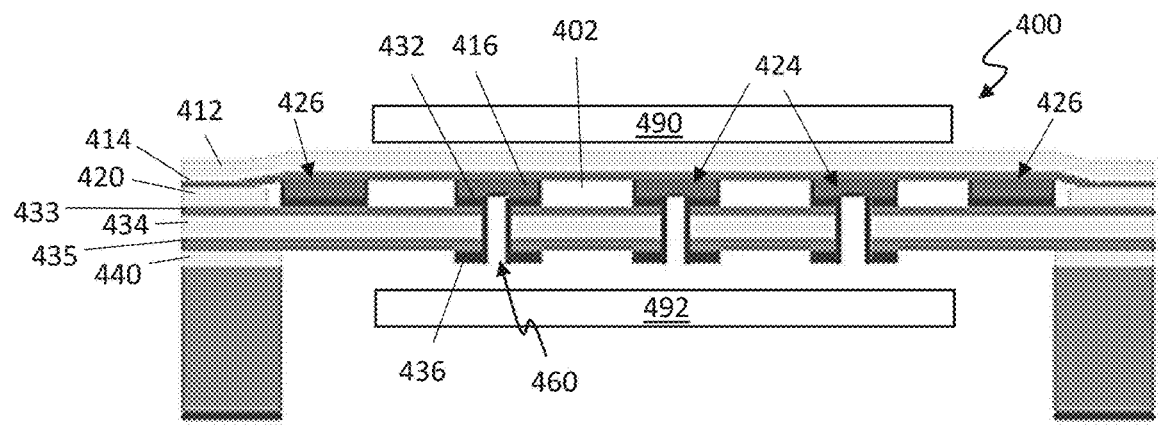
FIG. 4A
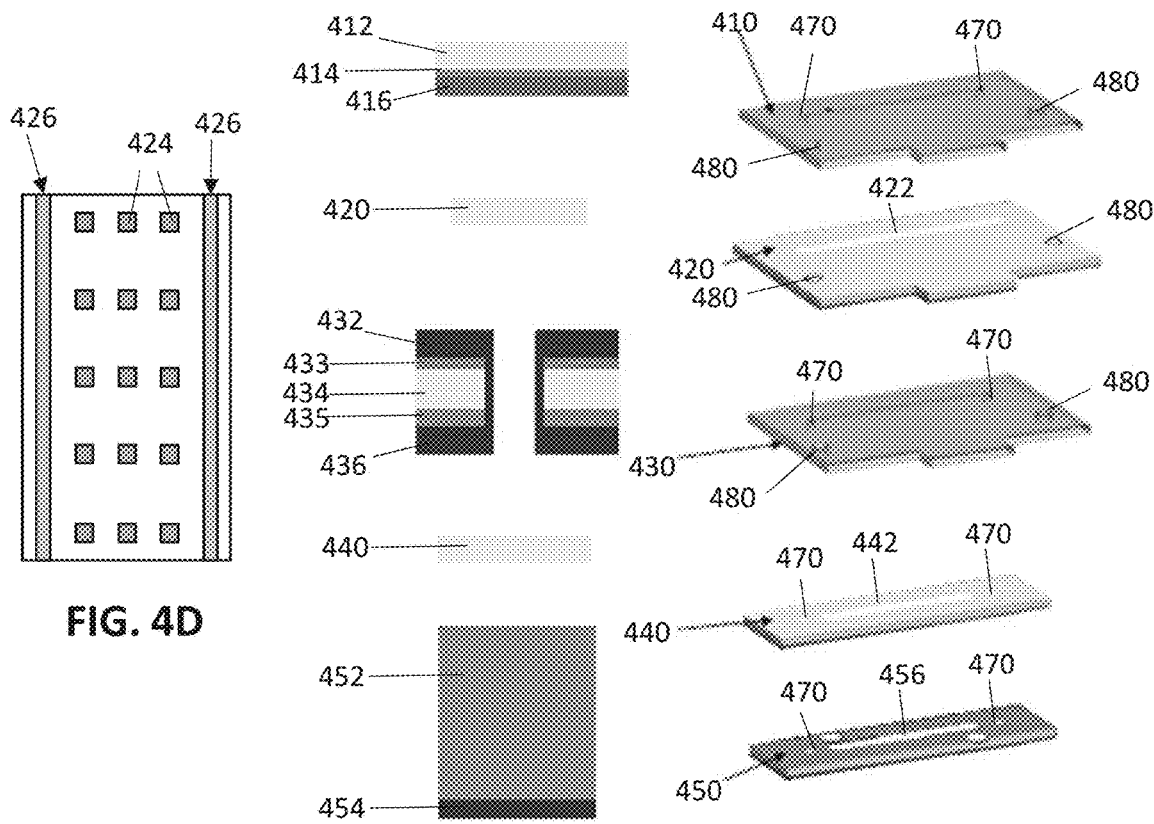
FIG. 4D
FIG. 4C
FIG. 4B 22 micron bead ~
Size of Circulating Tumor Cell

| Assay Type | Detected Marker | Research Application |
|---|---|---|
| Protein-Based Assays | Immunoglobulin G (IgG) | Immunity |
| | Lactate Dehydrogenase (LDH) | Cardiac Stress; Cancer |
| | Beta 2 Microglobulin (B2M) | Cancer Detection |
| | Cytokines: TNFa, IL-2 | Inflammation |
| | Streptavidin | Biotinylation |
| | Others | Partner-specific |
| Cell-Based Detection | WBC (anti-CD45) | Leukemia, cancer metastasis |
| | Red Blood Cells | General hemotology |
| | Yeast Cells | Expression Vectors |
| Expression Based Assays | Hybridomas | Drug Target ID |
| | B-cells | Drug Target ID |
| | Phage Display | Drug Target ID |

FIG. 12

0 ng/mL IgG 30 ng/mL IgG 480 ng/mL IgG

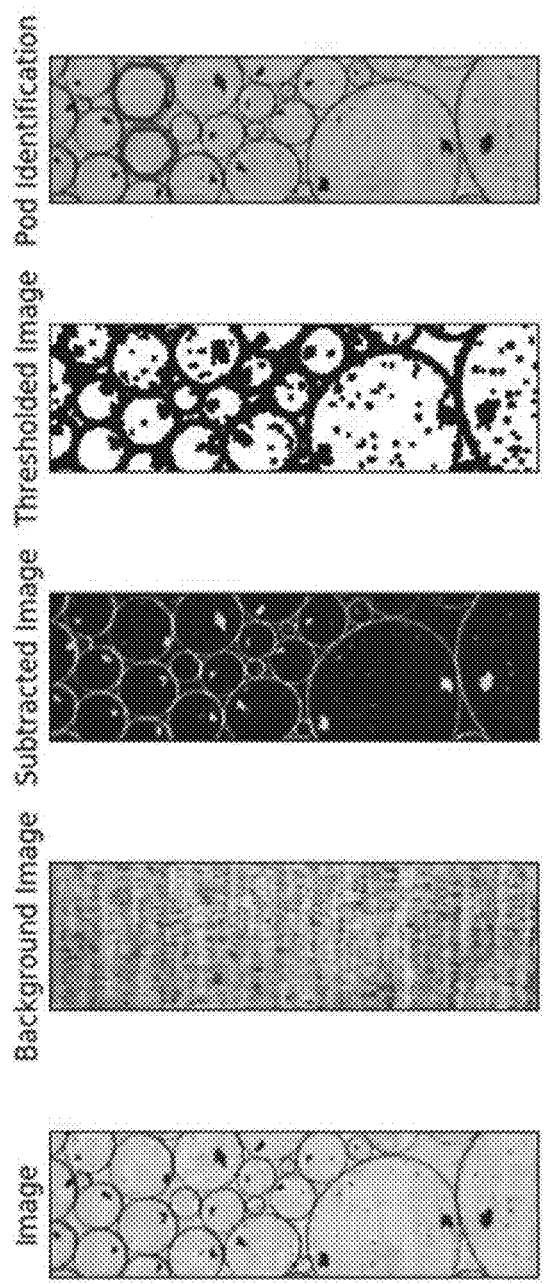

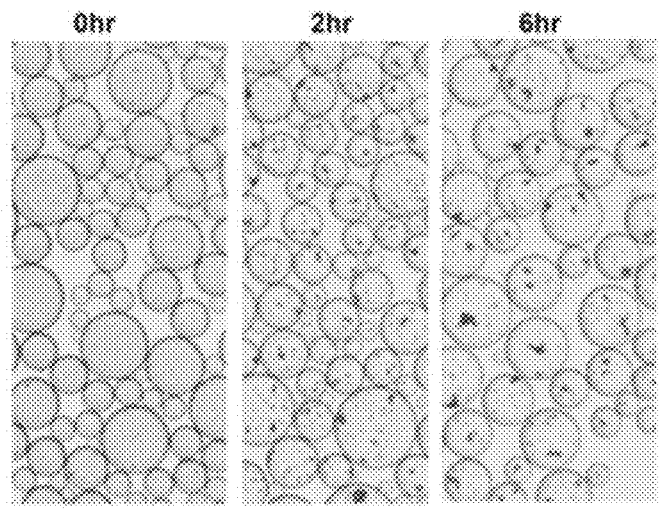
FIG. 25A  FIG. 25B  FIG. 25C
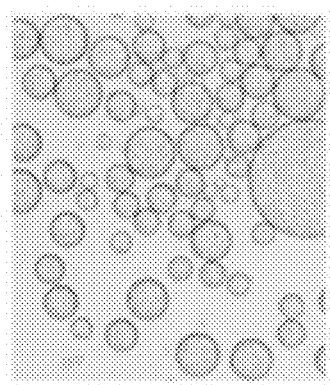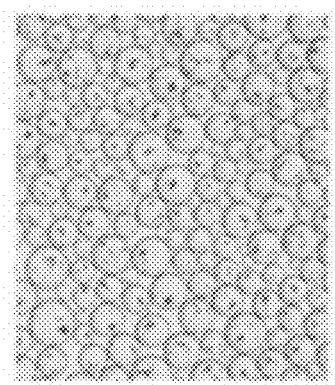
FIG. 26A  FIG. 26B

Exemplary System Parameters

| System Parameter | Value |
| --- | --- |
| Volume of aqueous cell media | 77 mL |
| Volume of carrier oil (fluoro-oil) with surfactant | 173 mL |
| Number of B cells in aqueous cell media | 10 million |
| % cells in aqueous cell media that are B cells | 0.65 |
| Total number of cells in aqueous cell media | 15.4 million |
| Number of empty PODS for each PODS with a cell in it | 9   ($\lambda=10$) |
| Total number of PODS generated | 154 million |
| Chamber gap height | 35 μm |
| Average volume per POD | 501 pL |
| Average diameter of POD | 135 μm |
| Cells not detected (per million PODS) | 170 |
| Total number of undetected cells | 2615 |

FIG. 29A

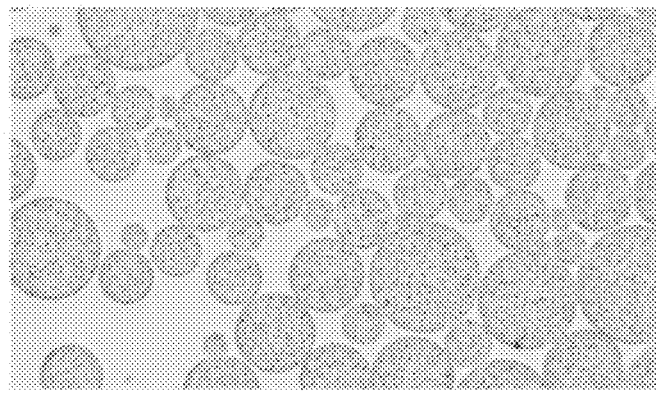
FIG. 39B
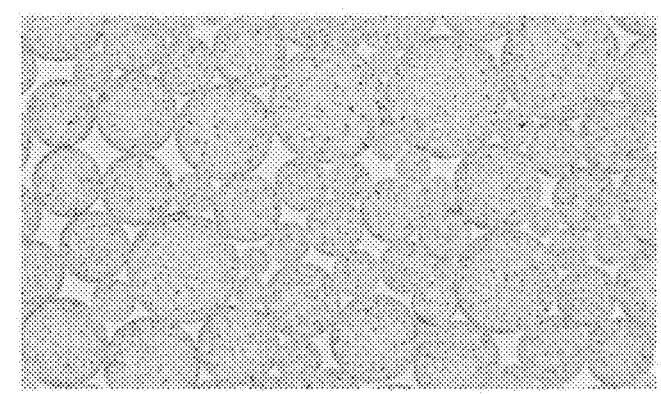
FIG. 39C
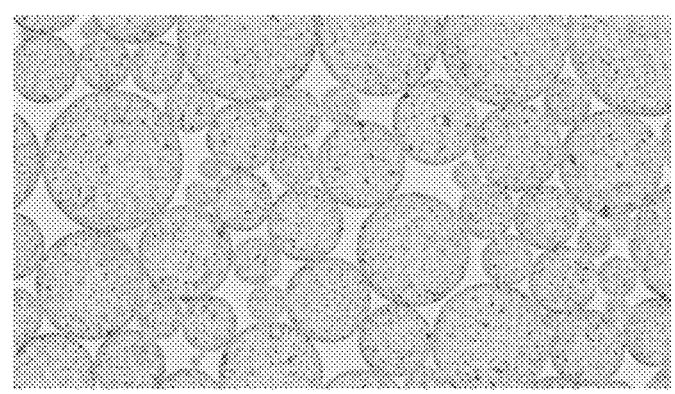
FIG. 39D

SYSTEMS AND METHODS FOR OPTICALLY PROCESSING SAMPLES

CROSS-REFERENCE TO RELATED APPLICATIONS

This application is a continuation of U.S. patent application Ser. No. 16/596,688, filed Oct. 8, 2019, now issued as U.S. Pat. No. 11,154,863, which claims priority to U.S. Provisional Application Ser. No. 62/859,666 filed Jun. 10, 2019, U.S. Provisional Application Ser. No. 62/800,385 filed Feb. 1, 2019, and U.S. Provisional Application Ser. No. 62/742,833 filed on Oct. 8, 2018, each of which is hereby incorporated by reference in its entirety.

TECHNICAL FIELD

This invention relates generally to the field of assays for processing sample entities.

BACKGROUND

Devices to conduct assays are commonly used for the purposes of biochemistry research, pharmaceutical discovery, cell screening, medical diagnostics, and other applications to detect and/or measure one or more components of a sample. A digital assay is one kind of assay that partitions a biological sample into multiple smaller containers such that each container contains a discrete number of biological entities. For example, a digital assay may be used to analyze microfluidic droplets including single cells or other entities, such as for quantifying nucleic acids, proteins, or other biological content.

Current microfluidic systems have a number of drawbacks. For example, conventional microfluidic digital assays require that droplets be monodisperse and of the same type (e.g., exclusively DNA) during an experiment, in order to, for example, accurately correlate measurements to analyte concentration and compare such measurements across different droplets. These devices require droplets to be pre-sorted to ensure that they are of suitably uniform size, which is time-consuming and reduces efficiency in processing droplets. Additionally, these devices include a linear, single-track microfluidic channel within which droplets travel in series for processing, which further limits the efficiency for analysis of the droplets. Accordingly, there is a need for new and improved digital assay systems and methods for processing samples.

SUMMARY

Generally, a system for processing a sample may include a chamber having at least one inlet and at least one outlet, where the chamber is configured to accommodate flow of the sample from the at least one inlet toward the at least one outlet. The system may further include an imager array configured to image the flow of the sample in the chamber, where the imager array includes at least one lensless image sensor configurable opposite at least one light source. In some variations, the chamber may be configured to accommodate a two-dimensional flow of the sample, such as movement in multiple directions (e.g., within an X-Y plane of the chamber). The imager may include a two-dimensional array of lensless image sensors for imaging sample flow in the chamber. As another example, the imager may include a one-dimensional or single-line array of lensless image sensors for imaging sample flow in the chamber. By being located opposite at least one light source across the chamber, the imager array may, in some variations, be configured to generate shadow images of the flow of the sample in the chamber.

The chamber may include opposing surfaces that are offset to form a spacing that receives sample flow. For example, the chamber may include a first surface and a second surface that is offset from the first surface. A plurality of spacers may be disposed between the first and second surfaces (e.g., to enforce and/or support the spacing between the first and second surfaces). At least one of the first surface and second surface may include an optically transparent material (e.g., polyimide, glass, etc.). At least one of the first surface and the second surface may be formed through planar processing techniques such as semiconductor manufacturing processes. The first surface and the second surface may be configured to flatten at least a portion of the sample, such that flattened samples or sample entities, as will be described in further detail herein, may flow through the chamber.

In some variations, the system may further include a light source, where the imager array and the light source are opposing each other across the chamber. The imager array may be embedded in a first structure having a first optically transparent portion adjacent the chamber. The light source may be embedded in a second structure having a second optically transparent portion adjacent the chamber.

Generally, another variation of a system for processing a sample may include a chamber defined at least partially by a first structure and a second structure opposing the first structure, where each of the first and second structures has at least a portion that is optically transparent. The system may further include at least one light source that is embedded in the first structure and configured to emit light toward the chamber, and an imager array embedded in the second structure and configured to image the chamber. The imager array may include at least one lensless image sensor. The imager array may include a one-dimensional or two-dimensional array of lensless image sensors. The imager array may be configured to generate shadow images of the flow of the sample. In some variations, the first structure and the second structure may be integrally formed.

The chamber may be configured to accommodate a two-dimensional flow of the sample between at least one inlet and at least one outlet of the chamber. The chamber may be configured to flatten at least a portion of the sample (e.g., between the opposing first and second structures). In some variations, a plurality of spacers may be disposed in the chamber between the first structure and second structure. At least one of such spacers may include an anchor bonding the first structure and the second structure together. For example, in some variations the anchor may include solder, polymer adhesive, or other suitable anchor material that may flow into one or more vias in a spacer and adjoin facing surfaces of the first and second structures.

In some variations, at least one of the first structure and second structure may include a laminated stack up of optically transparent layers. For example, at least one of the first structure and the second structure may be formed through planar processing.

The sample may, in some variations, include at least one POD as further described herein. At least one POD may include an analyte, such as a cell, DNA, RNA, a nucleotide, a protein, and/or an enzyme. Additionally or alternatively, at least one POD may lack, or not include, an analyte. In use, the assay system may be used to generate optical images of PODS and their contents, to generate information from which chemical and/or biological information may be derived.

Generally, in some variations, a system for processing a sample including a plurality of particles may include a chamber configured to accommodate the sample, where the chamber includes at least one electrode configured to deliver electrical energy sufficient to merge a selected portion of particles in the sample, and a sorting arrangement configured to separate particles of the sample based on particle size. For example, in some variations the chamber may include a plurality of electrodes extending between first and second opposing surfaces of the chamber (e.g., may provide structural support in combination with electrode functionality). The chamber may be configured to accommodate a two-dimensional flow of the sample. Furthermore, in some variations the system may further include an imager array (e.g., including a lensless image sensor) configured to generate one or more images of the sample in the chamber, and a controller configured to activate the at least one electrode to deliver electrical energy to the selected portion of particles based on the one or more images of the sample.

In some variations, the sorting arrangement may include a passive sorting arrangement. For example, the sorting arrangement may include a plurality of spacers. The spacers may be arranged in a staggered array and configured to perform particle separation via deterministic lateral displacement. As another example, the chamber may include a first outlet and a second outlet, where the first outlet is sized to pass substantially only particles below a predetermined threshold particle size, and the second outlet may be sized to pass particles above the predetermined threshold particle size. Additionally or alternatively, the chamber may include a plurality of branching channels configured to perform particle separation via hydrodynamic filtration. Additionally or alternatively, in some variations the chamber may include an active sorting arrangement (e.g., via active fluidic control, PDEP forces, etc.).

Generally, in some variations a system for processing a sample may include a chamber configured to accommodate the flow of a sample where the chamber includes at least one electrode configured to selectively deliver electrical energy to at least a portion of the sample, an imager array (e.g., including a lensless image sensor) configured to image the flow of the sample in the chamber, and a controller configured to activate the at least one electrode based on an analysis of the one or more images.

In some variations, the chamber may be configured to accommodate a two-dimensional flow of the sample. The chamber may include a plurality of electrodes, and the controller may be configured to selectively activate pairs of electrodes, such as adjacent electrodes. The activated electrodes may, for example, be capacitively coupled with one or more target particles, which may cause the target particles to merge.

In some variations, the system may further include a sorting arrangement configured to separate particles of the sample based on particle size. The sorting arrangement may include a passive sorting arrangement. The sorting arrangement may, for example, include a plurality of spacers arranged in a staggered array and configured to perform particle separation via deterministic lateral displacement. As another example, the chamber may include a first outlet and a second outlet, where the first outlet is sized to pass only particles below a predetermined threshold particle size, and the second outlet may be sized to pass particles above the predetermined threshold particle size. Additionally or alternatively, the chamber may include a plurality of branching channels configured to perform particle separation via hydrodynamic filtration. Additionally or alternatively, in some variations the chamber may include an active sorting arrangement (e.g., via active fluidic control, PDEP forces, etc.).

Generally, in some variations, a method for processing a sample including a plurality of particles (e.g., PODS) may include receiving a sample in a chamber including at least one electrode, characterizing one or more particles in the sample as discard particles, merging the discard particles by delivering electrical energy from the at least one electrode to the discard particles, and sorting particles of the sample based on particle size. In some variations, characterizing one or more particles may include receiving one or more images of the sample in the chamber and characterizing one or more particles based on the one or more images. The one or more images may include, for example, an optical shadow image of the sample.

In some variations, delivering electrical energy may include activating a pair of electrodes in accordance with a drive waveform. The drive waveform may, for example, be an AC waveform. The waveform may, in some variations, have a peak-to-peak voltage of between about 0.5 V and about 10 V, or between about 0.5 V and about 5 V. Furthermore, in some variations, the waveform may have a frequency between about 1 Hz and 1 MHz, or between about 50 Hz and about 20 kHz.

In some variations, sorting particles may include passively sorting the particles. For example, particles may be sorted via deterministic lateral displacement. As another example, particles may be sorted by permitting particles of a first size to pass through a first outlet of the chamber, and permitting particles of a second size to pass through a second outlet of the chamber. Additionally or alternatively, particles may be sorted via hydrodynamic filtration.

Furthermore, the method may in some variations be used to process a sample in which at least a portion of the particles contains one or more cells (e.g., CHO cells, hybridomas, B cells, myeloma cells, etc.) secreting a substance of interest (e.g., antibody, insulin, etc.). In these variations, characterizing one or more particles in the sample may include characterizing secretion levels of the one or more cells, such as by characterizing agglutination in the one or more cells. For example, particles lacking secretor cells and/or particles containing low secretor cells may be characterized as discard particles, while particles including high secretor cells may be characterized as particles of interest. Particles for discard and particles of interest may be sorted and separated. For example, sorting may include sorting particles below a threshold size as particles of interest (e.g., particles containing high secretor cells). In some variations, the sample may be prepared such that there is an average of about 0.1 cells per particle.

Generally, in some variations, a system for enabling selection of a cell of interest from a population of cells may include an encapsulation reagent, where the encapsulation reagent has a density greater than about 1.0, and a first plurality of particles suspended in aqueous media, where each particle of the first plurality of particles includes a first binding partner that is specific to a second binding partner secreted by the cell of interest. In some variations, the encapsulation reagent may include a surfactant. In some variations, the surfactant includes at least one of fluorine and polyethylene glycol. In some variations, each particle of the first plurality of particles may have a diameter between about 30 nm to about 50 µm. In some variations, each particle of the first plurality of particles may include at least one of polystyrene, gold, cellulose, latex, agarose, polyethylene glycol (PEG), glass, and magnetic beads. In some variations, a first cluster site is formed by a binding of the first and second binding partners. In some variations, the first binding partner and the second binding partner may be a first and second protein. In these variations, the first binding partner or the second binding partner may be an antigen or antibody. For example, the antibody may be IgG. In some variations, the first binding partner and the second binding partner may be a first and second peptide.

Furthermore, the system in some variations may also include a second plurality of particles, where each particle of the second plurality of particles has a third binding partner that is specific to a fourth binding partner secreted by the cell of interest. In these variations, the system may further include a second cluster site formed by a binding of the third and fourth binding partners.

Generally, in some variations, a mixture may include an encapsulation reagent, one or more first particles suspended in aqueous media, where each first particle includes a first binding partner, and a population of cells with at least one cell of interest that secretes a protein of interest having a second binding partner, where the first binding partner is specific to the second binding partner. In some variations, the encapsulation reagent may include a surfactant. In some variations, the surfactant includes at least one of fluorine and polyethylene glycol. In some variations, the encapsulation reagent may be between about 60% and 90% of the mixture by volume. In some variations, the one or more first particles may be between about 5% and 20% of the mixture by volume. In some variations, the population of cells may be between about 5% and 20% of the mixture by volume. In some variations, each particle of the first plurality of particles may have a diameter between about 30 nm to about 50 μm. In some variations, each particle of the first plurality of particles may include at least one of polystyrene, gold, cellulose, latex, agarose, polyethylene glycol (PEG), glass, and magnetic beads. In some variations, the mixture may further include a first cluster site formed by a binding of the first and second binding partners. In some variations, the first binding partner and the second binding partner may be a first and second protein. In these variations, the first binding partner or the second binding partner may be an antigen or antibody. For example, the antibody may be IgG. In some variations, the first binding partner and the second binding partner may be a first and second peptide. In some variations, the population of cells may include at least one or more of CHO cells, B cells, hybridoma cells, plasma cells, HEK293 cells, myeloma cells, and T cells. In some variations, the one or more first particles may include one or more cells, and the first binding partner may include antigens expressed on the one or more cells. In some variations, the first plurality of particles may include a second population of cells, and the first binding partner may include antigens expressed on the second population of cells.

Furthermore, in some variations, the mixture may also include a plurality of sample entities, where each sample entity encapsulates at least one or more of the one or more first particles, at least one cell from the population of cells, and the aqueous media. In these variations, the plurality of sample entities may be polydisperse sample entities.

Furthermore, the mixture in some variations may also include a second plurality of particles, where each particle of the second plurality of particles has a third binding partner that is specific to a fourth binding partner secreted by the at least one cell of interest. In these variations, the system may further include a second cluster site formed by a binding of the third and fourth binding partners.

Generally, in some variations, a method for preparing a sample for a clustering assay system may include providing a population of cells having at least one cell of interest, combining the population of cells, a first plurality of particles, and an encapsulation reagent to create a mixture, where each particle of the first plurality of particles is suspended in aqueous media and includes a first binding partner that is specific to a second binding partner secreted by the at least one cell of interest; and agitating the mixture to create an emulsion, thereby encapsulating the population of cells into a plurality of polydisperse sample entities (e.g., PODS). In some variations, the first binding partner and the second binding partner may be a first and second protein. In these variations, the first binding partner or the second binding partner may be an antigen or antibody. For example, the antibody may be IgG. In some variations, the first binding partner and the second binding partner may be a first and second peptide. In some variations, the population of cells may include at least one or more of CHO cells, B cells, hybridoma cells, plasma cells, HEK293 cells, myeloma cells, and T cells. In some variations, the first plurality of particles may include a second population of cells, and the first binding partner may include antigens expressed on the second population of cells.

In some variations, providing the population of cells may include diluting the population of cells to obtain a desired cell concentration of between about 100,000 and 300,000 cells per milliliter. In these variations, the desired cell concentration may be about 220,000 cells per milliliter.

Furthermore, in some variations, combining the population of cells, the first plurality of particles and the encapsulation reagent may also include adding a second plurality of particles to form the mixture, where each particle of the second plurality of particles comprises a third binding partner that is specific to a fourth binding partner secreted by the at least one cell of interest. In these variations, the second binding partner and the fourth binding partner may be a first component and a second component of an antibody, respectively.

Furthermore, in some variations, the emulsion may be characterized by a λ value, where λ is a number of cells per sample entity of the plurality of polydisperse sample entities. In these variations, the λ value may be between about 0 and about 10 cells per sample entity.

Furthermore, the method in some variations may also include incubating the emulsion for a predetermined length of time. In these variations, the predetermined length of time may be between about 1 and about 6 hours.

Generally, in some variations, a method for selecting at least one cell of interest from a population of cells may include providing an emulsion having the population of cells and a first plurality of particles, where the population of cells and the first plurality of particles are encapsulated into a plurality of polydisperse sample entities (e.g., PODS), and where each particle of the first plurality of particles is suspended in aqueous media and includes a first binding partner that is specific to a second binding partner secreted by the at least one cell of interest, measuring a signal for at least one sample entity, where the signal is at least partially associated with binding of the first and second binding partners; and identifying the at least one cell of interest based at least in part on the measured signal. In some variations, the second binding partner may be coupled to a first component of a protein of interest secreted by the at least one cell of interest, and where the measured signal quantifies the protein of interest in the at least one sample entity. In some variations, the first plurality of particles may include a second population of cells, and the first binding partner may include antigens expressed on the second population of cells.

In some variations, the emulsion may also include a second plurality of particles encapsulated into the plurality of polydisperse sample entities (e.g., PODS), where each particle of the second plurality of particles includes a third binding partner that is specific to a fourth binding partner secreted by the at least one cell of interest. In these variations, the signal may at least partially be associated with a binding of the first and second binding partners, and may at least partially be associated with a binding of the third and fourth binding partners. In these variations, the second binding partner and the fourth binding partner may be associated with a protein of interest secreted by the at least one cell of interest, and the measured signal may quantify binding affinity and/or specificity of the protein of interest to the first binding partner or the third binding partner. In these variations, the measured signal may quantify antigen binding affinity and/or specificity of an antibody secreted from a cell of interest.

In some variations, identifying the at least one cell of interest may include identifying at least a portion of the sample entities that has a measured signal greater than a predetermined threshold. In some variations, measuring the signal for the at least one sample entity may include receiving at least one shadow image of the at least one sample entity, and determining a size score of at least one object in the sample entity based on the at least one shadow image, where the measured signal is based at least in part on the size score.

Furthermore, in some variations, the method may also include introducing the emulsion into a chamber adjacent an imager array configured to generate the at least one shadow image.

Furthermore, in some variations, the method may also include removing at least one cell of interest from the polydisperse sample entities. In these variations, the method may also include analyzing the at least one cell of interest with one or more of PCR, FACS, DNA sequencing, and ELISA.

BRIEF DESCRIPTION OF THE DRAWINGS

FIGS. 4A-4D depict schematic illustrations of an exemplary variation of a chamber arrangement. FIG. 4A depicts a cross-sectional view of a variation of a chamber arrangement. FIG. 4B depicts an exploded view of a portion of the chamber arrangement depicted in FIG. 4A. FIG. 4C depicts a cross-sectional view of the portion of the chamber arrangement depicted in FIG. 4B. FIG. 4D is a partial top plan view of the chamber arrangement depicted in FIG. 4A.

FIG. 7A depicts a cross-sectional view of a variation of a chamber arrangement. FIG. 7B depicts a detailed partial cross-sectional view of the chamber arrangement depicted in FIG. 7A.

FIG. 8A depicts a cross-sectional view of a variation of a chamber arrangement. FIG. 8B depicts a top plan view of the chamber arrangement depicted in FIG. 8A.

FIG. 12 depicts a chart showing exemplary assay types that may be performed by the assay system.

FIG. 14A is an exemplary image of computer vision detection of PODS containing IgG at a concentration of 0 ng/mL. FIG. 14B is an exemplary image of computer vision detection of PODS containing IgG at a concentration of 30 ng/mL. FIG. 14C is an exemplary image of computer vision detection of PODS containing IgG at a concentration of 480 ng/mL.

FIGS. 21A-21E illustrate an exemplary method for processing an image of one or more PODS and identifying PODS in the processed image.

FIGS. 25A-25C are images illustrating exemplary hybridoma growth rates over time, as viewed with imager systems described herein.

FIGS. 26A and 26B are images illustrating exemplary hybridoma secretion ranges associated with low and high IgG concentrations, respectively, as viewed with imager systems described herein.

FIG. 29A is a table of system parameters for an exemplary electromerging chamber arrangement and exemplary sample with B cells.

FIGS. 36A-36C show that all batches of beads showed clustering when 10 µg/ml of mouse or human IgG were present. Each batch is shown against a no cell (NC) control.

FIGS. 39B-39D depict 10× objective microscope images at time=0, t=1 hour, and t=3 hours, showing that clustering occurred starting from t=1 hour.

DETAILED DESCRIPTION

Figure 1A:
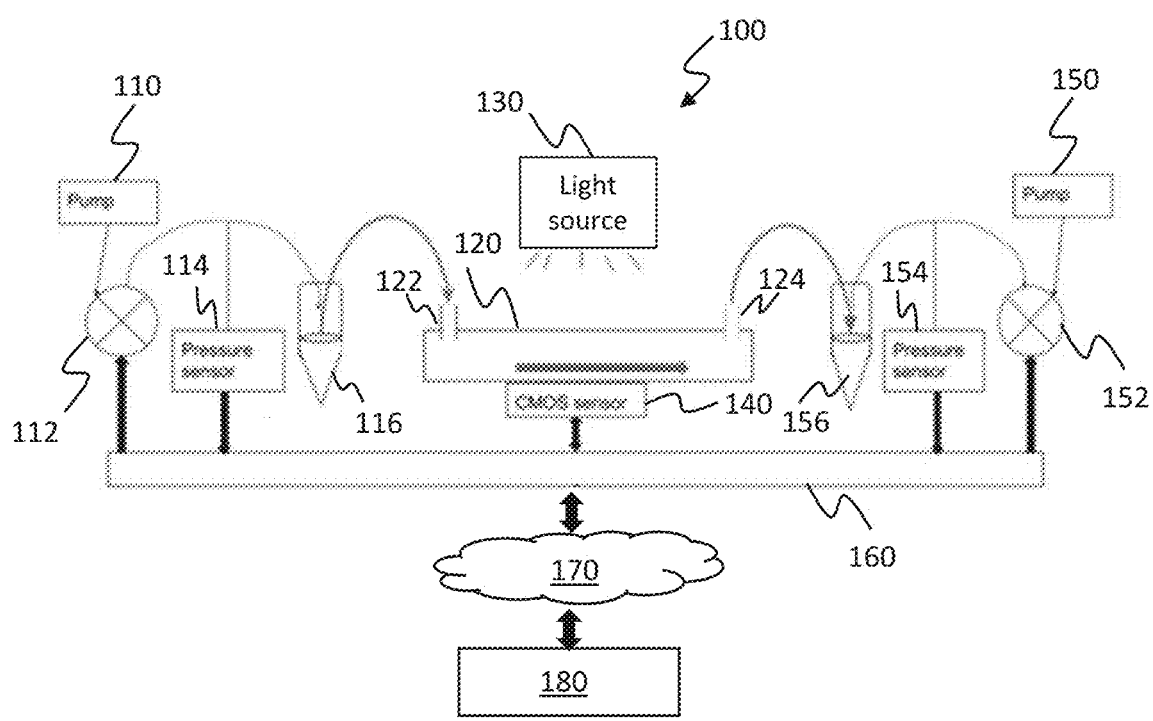
FIGS. 1A and 1B depict schematic illustrations of exemplary variations of an assay system for optically processing samples.

Non-limiting examples of various aspects and variations of the invention are described herein and illustrated in the accompanying drawings.

Generally, described herein are exemplary variations of assay systems and methods for processing samples. For example, such systems and methods may process a large number of entities within the sample substantially in parallel, such as to enable rapid experimental analysis of the sample. Furthermore, the systems and methods described herein may be used to process polydisperse entities of non-uniform size. Generally, the systems and methods described herein may facilitate measurements of diagnostic- and/or research-related events or sample characteristics, such as agglutination, colloidal stability, cell growth, cell surface profiling, cell size profiling, and/or the profiling of concentration of proteins, antibiotics, nucleotides, other analytes, and the like. Applications may include diagnostics, drug research, environmental research, and the like.

PODS

As described in further detail below, the systems and methods may, for example, process partitioned samples. For example, the systems and methods may process suitable experimental dispersion, a type of which is also referred to herein as Polydisperse Oblate Dispersion System ("PODS.") A POD may include in its body any suitable experimentally useful content, such as bacterial or mammalian cells, DNA, RNA, nucleotides, proteins, enzymes, and/or any suitable chemical and/or biological content for analysis. In other examples, a POD may include reagents that are used to confer signals to one or more image sensors such that the PODS may be processed by software to yield meaningful chemical and/or biological information. PODS may, for example, be used for the early detection of molecules secreted from a mammalian cell, such as IgG from a hybridoma or B cell. Suitable reagents or agglutinates may include, for example, beads coated with gold, latex, cellulose, agarose, polystyrene, magnetic, and/or other materials bound to biologically active proteins or scaffolds (e.g., materials suitable for ELISA kits and agglutination assays such as cell surface binding and cell agglutination assays). Additionally, in some variations (e.g., for samples with cell cultures), a substance such as L-glutamine may be encapsulated in the PODS so as to help keep cells viable. Furthermore, in some variations, PODS may include hydrogels or a porous solid or polymeric phase that serve as an anchor for a capture protein or antibody. A sandwich type assay can then be constructed with a sample that is specific to the capture protein, and a second detection antibody that is bound to a detection catalyst or enzyme such as Horse Radish Peroxidase, HRP. A darkening substrate such as PCIB can then be added.

For example, a POD could include any such bead having a size between about 10 nm to about 50 µm, and coated with a biomarker (e.g., antibody). As another example, a POD could include a bead having a size between about 30 nm to about 50 µm. The degree of agglutination resulting from self-aggregation of such reagents or agglutinates (which may be monodisperse or polydisperse) in the assay system described herein may, for example, enable inference of protein and/or analyte concentrations. Thus, analytes of interest include, but are not limited to, various chemical and/or biological mixtures including buffers, cells, tissues, lysates, agglutinates, aggregate proteins, drugs, antibodies, nucleotides, dyes, and/or coated particles, etc. Exemplary applications of the systems and methods described herein are shown in FIG. 12 and described in further detail below.

In some variations, each POD may be considered a separate experiment, such that processing of multiple PODS enables the fast and efficient performance of multiple experiments in parallel. Processing PODS may involve, without limitation, analyzing one or more characteristics of PODS, tracking location and/or predicting trajectory of PODS within the chamber, and/or manipulating PODS for sorting.

In some variations, a POD may include an aqueous phase that is stabilized and is transportable in a surrounding medium such as a liquid or other fluid (e.g., a non-aqueous solution containing a surfactant or lipid, or mixture thereof). In some variations, a POD being processed by the assay device may be distinct from a droplet at least in part because a POD is not spherical. For example, a processed POD might not be spherically symmetrical. The processed POD may be smaller in one dimension (e.g., in a dimension measured generally orthogonal to an electrode surface as described below) than in another dimension (e.g., oblate). For example, the processed POD may be generally flattened on at least one side, similar to a generally hemi-spherical shape, or may be generally flattened on at least two opposing sides, similar to a disk-like or "pancake" shape. As described in further detail below, a POD that is flattened on at least one side may have increased surface area of contact with measurement electrodes in the assay device, such that electrode measurements may have reduced noise and generally improved signal quality. Additionally, as described in further detail below, a POD that is flattened on at least one side may be volumetrically restricted so as to concentrate the POD contents into a shape approximating a two-dimensional focal plane of a camera, thereby improving visibility of the POD contents by the camera. Furthermore, a POD may be distinct from a droplet at least in part because multiple PODS being processed simultaneously by the assay device may be polydisperse, in contrast to droplets which are conventionally thought of as being the same size (e.g., having monodisperse characteristics).

For example, a POD may be pressed into a flattened form (e.g., by mechanical compression between two plates, between opposing surfaces of a chamber such as that described below, or other suitable mechanism), by increasing surfactant concentration, or in any suitable manner.

The surrounding medium for the PODS may, for example, include a non-aqueous continuous phase. In some variations, the surrounding medium may be fluorous. For example, the medium may include a fluorinated oil or other liquid (e.g., HFE 7500 available as Novec™ manufactured by 3M™ or FC-40, available as Fluorinert™ manufactured by 3M). As another example, the medium may include hydrocarbon oil. The medium may, in yet other variations, additionally or alternatively include PEG and fluoridated derivatives (e.g., derivatives of Krytox™ fluorinated oils manufactured by The Chemours Company, which may be polymerized or co-polymerized with PEG or other suitable glycol ethers), and may include lipids or other phosphoric, carboxylated or amino-terminated chains.

In some variations, a POD may have an overall density that is lower than the density of the surrounding medium, such that aqueous PODS within the medium are more buoyant and tend to rise within the surrounding medium. For example, the surrounding medium may include a fluid denser than water, such as HFE-7500 and/or FC-40, which may be mixed with co-block polyethylene glycol/Krytox™ polymer. In other variations, a POD may have an overall density that is higher than the density of the surrounding medium such that aqueous PODS within the medium are less buoyant tend to sink within the surrounding medium. For example, the surrounding medium may include a fluid less dense than water, such as hexadecane and a phospholipid bilayer. In yet other variations, a POD and its surrounding medium may have substantially similar or equal densities. It should be understood that various combinations of relative densities of PODS and the surrounding medium may provide varying levels of buoyancy of the PODS within the surrounding medium (e.g., a set of PODS within a particular medium may include some PODS that tend to rise and some PODS that tend to sink). For example, relative buoyancy of the PODS may be beneficial in some applications to leverage gravity in the sorting of PODS. However, the POD may be surrounded by any suitable medium.

One or more PODS may be introduced in combination with a suitable surrounding medium as an emulsion into an assay device and processed as described herein. In some variations, mixing to create PODS may occur outside of the assay device (e.g. adjacent an external side of an inlet of the device prior to introduction into the device), while in other variations such mixing may additionally or alternatively occur inside the assay device. For example, PODS may be generated by agitating two solutions including a biological reagent and a fluorinated liquid. Furthermore, larger PODS may be transformed into smaller PODS (e.g., by interaction with spacers in the assay device as described below, or interaction with any other suitable device feature) to control or adjust polydispersity among the PODS.

The assay devices and methods may be used to process polydisperse sample entities. For example, various aspects of the devices and methods described herein may enable substantially simultaneous processing of PODS of different sizes, in contrast to conventional systems which require samples to be monodisperse. In some variations, the assay devices and methods described herein may simultaneously process sample entities having at least 5%, at least 10%, at least 25%, or at least 50% variance in size (e.g., POD diameter, POD circumference, POD surface area, POD volume, etc.). The ability to handle polydisperse samples may, for example, provide sample analysis that is simpler and more efficient (e.g., by not requiring the sample entities to be sorted by size in a separate, time-consuming process before introducing them into an assay device).

Exemplary applications of the assay devices and methods described herein include processing PODS to measure analyte concentration, measure cell division, measure morphology, size, and/or number of cells or particles within a POD or other sample entity, measure relative sizes of cells (and/or agglutinates) and the PODS within which they are contained (e.g., ratio between circumference of a POD and the circumference of a cell within the pod), and the like. For example, the devices and methods may be used for pathology, oncology, determining white or red blood cell counts, etc. Furthermore, the assay devices and methods described herein may be used to perform any of a wide variety of agglutination tests.

Assay System for Processing a Sample

Generally, as shown in the schematic of FIG. 1A, in some variations, an assay system 100 for processing a sample includes a chamber 120 having at least one inlet 122 and at least one outlet 124, wherein the chamber is configured to accommodate flow of the sample from the at least one inlet toward the at least one outlet, and an imager array 140 configured to image the flow of the sample in the chamber 120. The imager array 140 may include at least one lensless image sensor configurable opposite at least one light source 130. In some variations, the assay system 100 may include a fluidic control system with one or more pumps, valves, and/or fluid sensors to manipulate flow of the sample. The system 100 may further include an electronics system 160 (e.g., PCBA with one or more processors, etc.) configured to control and/or receive signals from other components of the assay system 100, as further described below. In some variations, the electronics system 160 may further include one or more communication components (e.g., Bluetooth, WiFi, etc.) configured to communicate data (e.g., image data) to a network 170 for analysis by one or more remote processors 180. Additionally or alternatively, at least some of the data may be analyzed by one or more processors located in the electronics system 160.

Figure 1B:
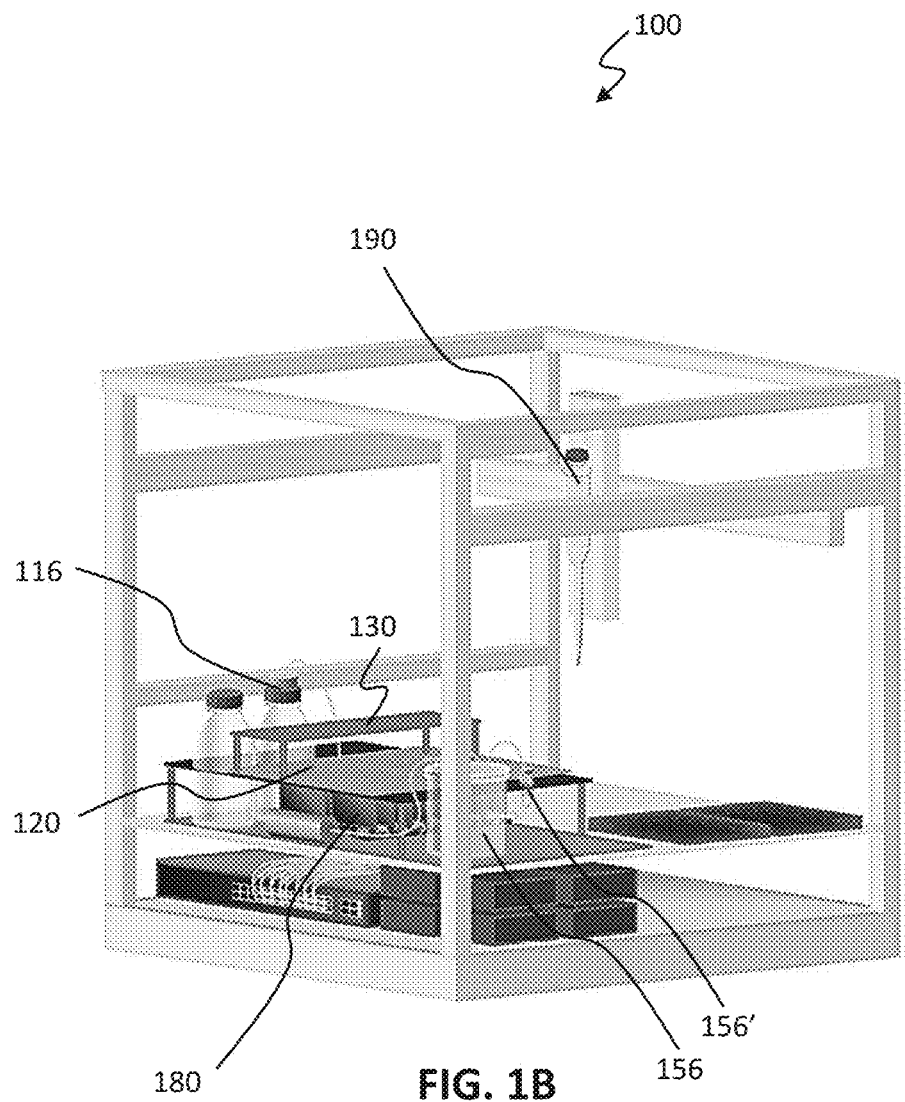

FIG. 1B depicts a schematic of an exemplary variation of a system 100 for processing a sample including a chamber 120 configured to receive a sample (e.g., emulsion) from a reservoir 116 coupled to an inlet of the chamber 120. The chamber 120 may be arranged between one or more light sources 130 and an imager array such that the imager array may produce optical shadow images of the sample within the chamber 120. The images may be analyzed using techniques such as those described herein, the sample may be processed (e.g., characterized and output into one or more waste containers such as a reservoir 156 and/or other receptacle 156' (e.g., Eppendorf tube). Furthermore, the system 100 may include a robotic or automated pipette 190 for drawing portions of the sample that may be of interest for further analysis or other processing.

Chamber Arrangement

As described above, the assay system may include a chamber having at least one inlet and at least outlet, and may be configured to accommodate flow of the sample from the at least one inlet toward the at least one outlet. Generally, the chamber may be configured to accommodate a two-dimensional flow of the sample, such that PODS (or other entities in the sample) may circulate within the volume of the chamber (e.g., in multi-directional flow). For example, the chamber may include a generally rectangular volume. In some variations, the chamber may be defined at least partially by a first structure and a second structure opposing the first structure, where each of the first and second structure has at least a portion that is optically transparent. In some variations, the chamber may be implemented at least in part on a flexible printed circuit board ("flex" circuit).

Furthermore, at least one light source may be positioned on one side of the sample flow in the chamber, and an imager array including at least one lensless image sensor may be positioned on the other side of the sample flow (opposite the light source) in the chamber. In such an arrangement, the imager array may be configured to generate "shadow images," or images through shadowgraphy, of chamber contents that are backlit by the at least one light source. Information (e.g., chemical and/or biological information) about samples may be derived from such shadow images of the samples.

In some variations, the assay device may additionally or alternatively include one or more electrodes configured to measure electronic characteristics of samples (e.g., perform impedance measurements that may be correlated to chemical and/or biological information about the samples, for example) and/or generate electrical fields to enable dielectrophoresis. For example, the chamber may include electrodes similar to those described in U.S. patent application Ser. No. 15/986,416 which is hereby incorporated in its entirety by this reference. Additional examples of such electrodes are described in further detail below, with respect to exemplary variations of chamber arrangements.

Figure 2A:
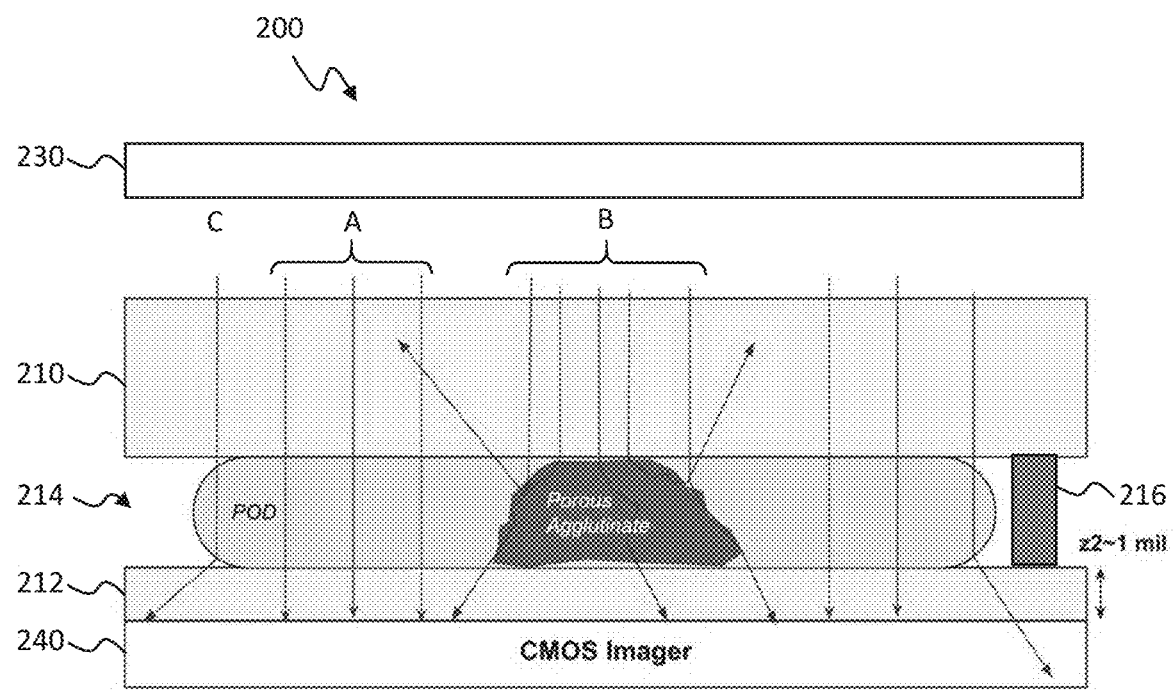
FIG. 2A depicts a schematic illustration of a chamber arrangement with a lensless image sensor.

Generally, as shown in in the cross-sectional view schematic of FIG. 2A, a chamber arrangement may include a chamber 200 having a first structure 210 and a second structure 212, where the first and second structures include an optically transparent material and are offset from each other to form a gap 214 or at least partially defining a chamber volume. Spacing between the first structure 210 and the second structure 212 may, in some variations, be supported or enforced by one or more spacers 216 as further described herein. Thickness of spacers may be determined to, for example, adjust chamber height and/or operational parameters such as emulsion stability, POD flow rate, etc. In some variations, chamber height may be at least part based on the kind of PODS or sample desired to be analyzed. Suitable chamber heights may range, for example, between about 0.1 µm to about 200 µm. For example, some PODS may include cells that may be best analyzed using a chamber having a taller height such as 25-30 µm, while some PODS may include proteins that may be best analyzed using a chamber having a shorter height such as less than 1 µm.

The first structure 210 and the second structure 212 may include multi-layer stackups formed with semiconductor planar processing techniques (e.g., adding material on a substrate with deposition, sputtering, plating, and/or immersion processes, subtracting material to introduce patterning such as with photolithography or other etching processes, or laser-defined imaging processes, etc.). A layer may be a continuous structure (e.g., a nonpatterned thin film) or a discontinuous structure (e.g., a patterned thin film with cutouts, gaps, etc.). By utilizing such planar processing techniques, the structures forming the chamber may be dimensionally scaled at low cost. Scalability across a plane enables the assay device to image or detect many PODS simultaneously, thereby increasing analysis throughput, or the total number of events (e.g., PODS, or reactions within PODS, etc.) that may be detected over a period of time. Furthermore, these manufacturing techniques enable precise control of chamber height, shape, and footprint area, thereby allowing for flexibility in customizing the overall assay device for a wide range of applications (e.g., sample types with different POD sizes, for example).

A light source 230 may be positioned on one side of the chamber and be configured to emit light toward the gap 214. An imager array 240 with a lensless image sensor (e.g., CMOS imager) may be positioned on the other side of the chamber, opposite the light source 230, and configured to image the region of the gap 214. Specifically, the lensless image sensor may be placed directly on the chamber (or alternatively used to directly form the boundary of the chamber), without an objective lens or other optical focusing lenses in the line of sight between the lensless image sensor and the chamber. The first structure 210 and the second structure 212 may include an optically transparent material, such that light from the light source 230 may pass through an optically transparent portion of the first structure 210, travel across the gap 214, pass through an optically transparent portion of the second structure 212, and be incident on the imager array 240.

A sample may flow through the chamber 200 in the gap 214, as represented in FIG. 2A as a POD passing through gap 214. For purposes of illustration, the POD can include an analyte such as an agglutinate, as shown in FIG. 2A, though it should be understood that a POD can include other kinds of analytes (or no analyte). Light from the light source 230 may be emitted toward the chamber (and toward the POD within the chamber) and interact with the POD and its contents when the POD is in the chamber. The imager array 240 may be configured to detect and image the optical phenomena resulting from these interactions, including, for example, shadows, absorbance or emission spectra (e.g., fluorescence), extinction coefficient, light scattering, etc.

Figure 2B:
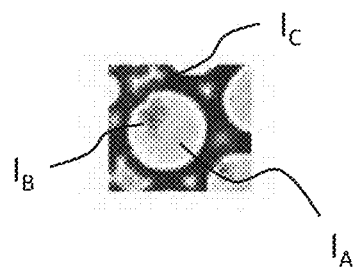
FIG. 2B depicts an exemplary shadow image obtained with a lensless image sensor in the chamber arrangement of FIG. 2A.

For example, FIG. 2A illustrates a system in which the imager array 240 is configured to generate shadow images of the sample flow in the chamber. The light source 230 may be configured to emit light (e.g., visible light) toward the sample flow. As shown in FIG. 2A, some light rays (e.g., light rays "A") may enter the chamber and pass through the aqueous portion of the POD relatively undisturbed, which causes the aqueous portion of the POD to be imaged by the imager array 240 as a bright, backlit region (e.g., region $I_A$ in FIG. 2B). Some light rays (e.g., light rays "B") may enter the chamber and be scattered or reflected due to the agglutinate (or other analyte(s)) in the POD, which causes the agglutinate (or other analyte(s)) to be imaged by the imager array 240 as a somewhat darkened, indefinite or "fuzzy" region (e.g., region $I_B$ in FIG. 2B). In some variations, information about the POD and its contents, such as size, shape, and/or density of the agglutinate, may be determined based at least in part on the darkened, indefinite region of the image (e.g., based on size, shape, pixel intensity, etc. of the region). Furthermore, some light rays (e.g., light rays "C") may enter the chamber and undergo diffraction at the POD boundary, which causes the POD boundary to be imaged as a dark, shadowed border region (e.g., $I_C$ in FIG. 2B). In some variations, the overall shape and/or size of the POD may be determined based at least in part on the border region (e.g., shape, size, pixel intensity, etc. of the border region). Accordingly, one or more lensless image sensors in the imager array 240 may be configured to generate "shadow images" of the backlit contents of the chamber. Chemical and/or biological properties may be derived from these shadow images.

Figure 9:
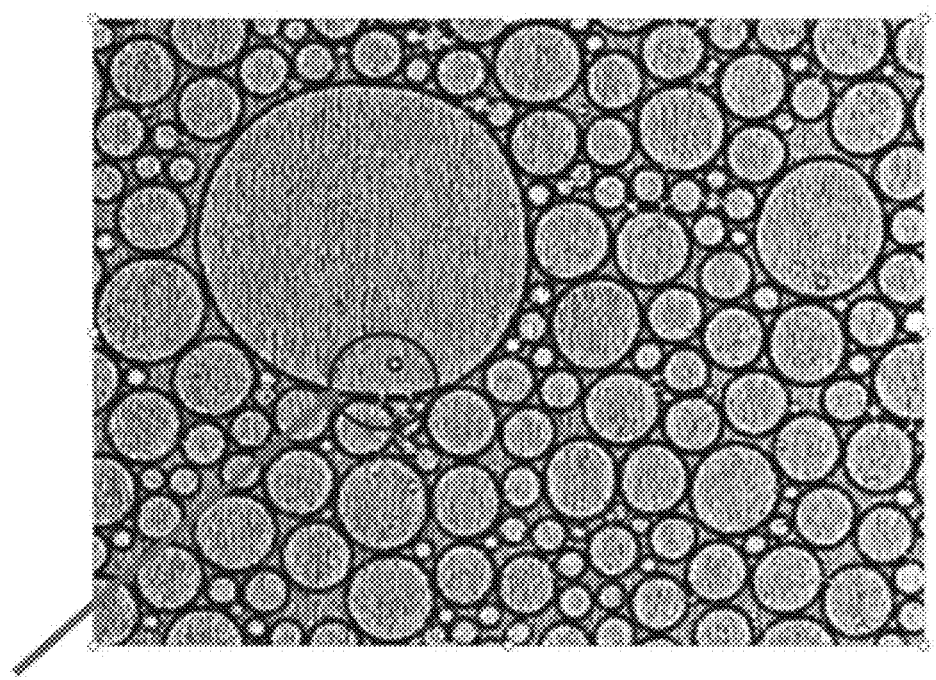
FIG. 9 depicts an exemplary image taken with a lensless image sensor in an exemplary variation of an assay system for optically processing samples.

FIG. 9 is an exemplary shadow image of sample flow in a chamber such as that shown in FIG. 2A. The shadow image is the result of processing a raw shadow image taken by a lensless CMOS image sensor adjacent the chamber and opposite a light source that provides backlighting of the sample flow in the chamber. The sample flow includes multiple polydisperse PODS passing through the chamber. Some of these PODS include a bead about 22 μm in diameter, which is approximately the size of a circulating tumor cell and may be coupled to an antibody. Thus, the bead has an analyte that may be imaged (or is otherwise representative of another analyte that can be similarly imaged), if present in the POD. For example, a POD that includes a bead (e.g., latex, polystyrene, magnetic material, gold, etc.) coated with a biomarker may have a visually distinct pattern when the contents of the POD also include an entity that reacts or binds to the biomarker (e.g., epitope, antigen, or other marker). Such a visually and/or quantifiably distinct pattern (or change in pattern) may be used to quantitate the biomarker. As shown in the shadow image of FIG. 9, the size and shape of the POD are identifiable and measurable based on the appearance of darkened patterns within the PODS. Additionally, characteristics of beads in certain PODS are identifiable, such as presence of beads, size, shape, etc. Furthermore, by analyzing the appearance of the PODS and their contents over time across multiple shadow images, dynamic characteristics (e.g., movement and/or change in shape or size of POD contents) can be analyzed to provide additional information about the chemical and/or biological nature of the PODS.

Figure 10:
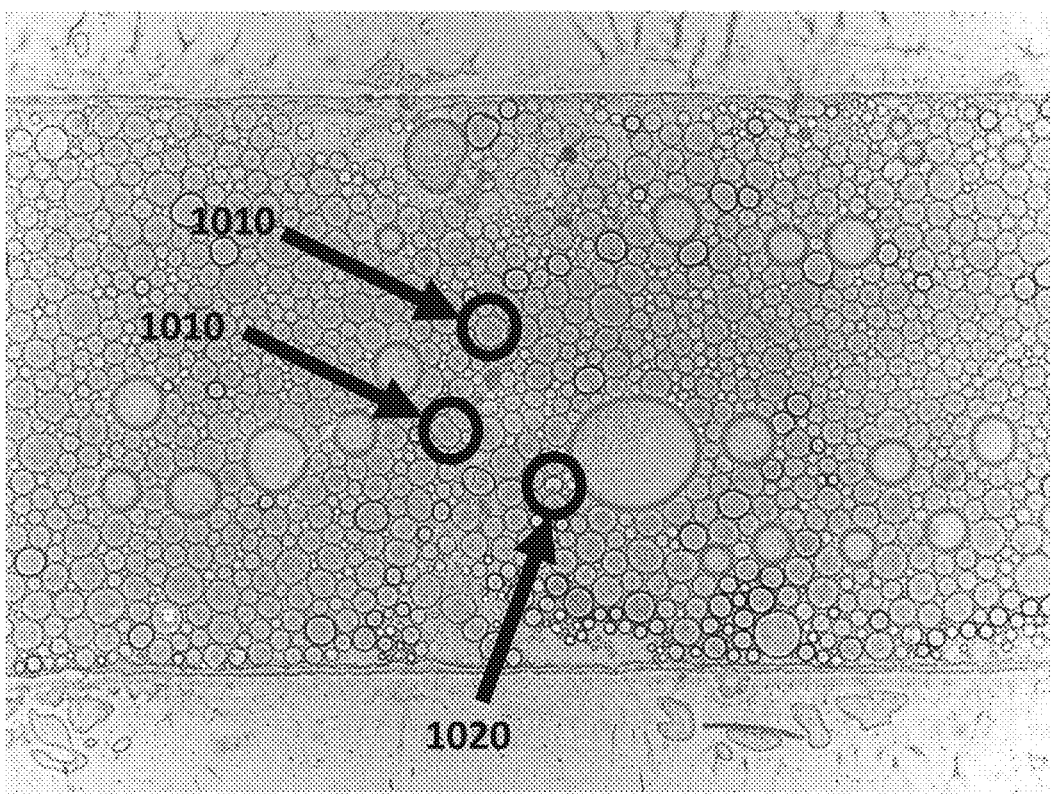
FIG. 10 depicts another exemplary image taken with a lensless image sensor in an exemplary variation of an assay system for optically processing samples.

FIG. 10 is another exemplary shadow image of sample flow in a chamber such as that shown in FIG. 2A. The sample flow includes multiple polydisperse PODS passing through the chamber. Some of these PODS (e.g., PODS 1010), may contain one or more red blood cells, while some PODS (e.g., PODS 1020) may be "empty" in that they lack red blood cells or other analytes. As shown in the shadow image of FIG. 9, the size and shape of the POD are identifiable and measurable based on the appearance of darkened lines outlining the PODS. Additionally, characteristics of the red blood cells in certain PODS are identifiable (e.g., number of red blood cells, etc.). Furthermore, similar to that described above with respect to FIG. 9, by analyzing the appearance of the PODS and their contents over time across multiple shadow images, dynamic characteristics (e.g., movement and/or change in shape or size of POD contents) can be analyzed to provide additional information about the chemical and/or biological nature of the PODS.

Figure 11A:
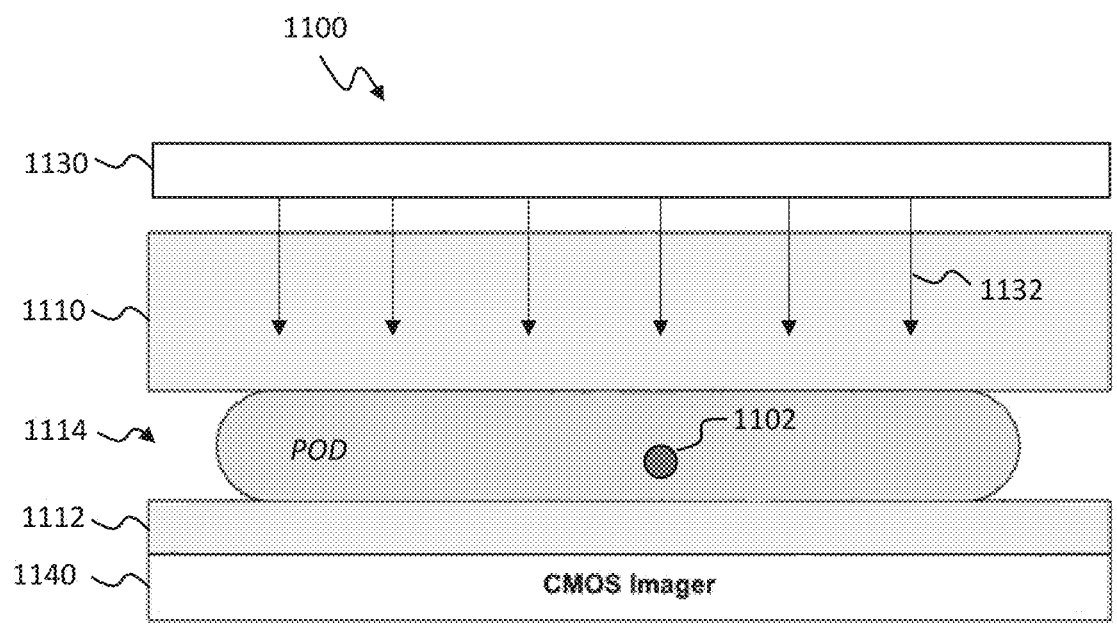
FIGS. 11A and 11B depict schematic illustrations of another exemplary variation of a chamber arrangement with a lensless image sensor.
Figure 11B:
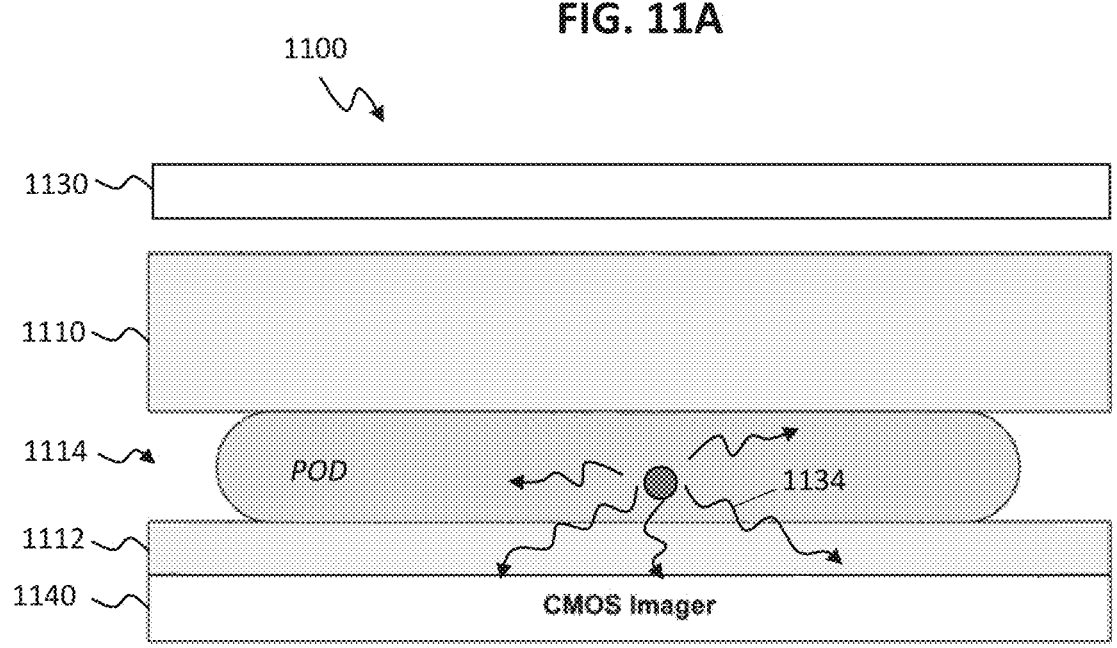

FIGS. 11A and 11B illustrate another exemplary variation in which the imager array is configured to obtain fluorescent images of the sample flow in the chamber. FIGS. 11A and 11B illustrate a chamber arrangement having a first structure 1110, a second structure 1112 offset with a gap 1114 as previously described and similar to the chamber arrangement described above with reference to FIG. 2A, except as described below. As shown in FIG. 11A, the light source 1130 may be configured to emit light 1132 suitable for inducing fluorescence or other emission spectra toward the sample flow. The emitted light 1132 may, for example, include ultraviolet light (UV). At least some PODS in the sample flow may include a bead or biological sample 1102 or other substance configured to absorb the emitted light and emit light in response (e.g., of a different wavelength). For example, as shown in FIG. 11B, at least some emitted light may be absorbed by a POD or contents therein, which may in turn emit fluorescence or other light emission 1134. The emitted fluorescence may be imaged as a fluorescent image by at least a portion of the image sensors in the imager array 1140. Chemical and/or biological properties may be derived from these fluorescent images (e.g., based on wavelength of emitted light, intensity of emitted light, etc.).

Furthermore, although the chamber arrangement of FIGS. 11A and 11B depict an imager array 1140 that is opposite the light source 1130 emitting light for inducing fluorescence, it should be understood that in other variations, the imager array 1140 may be located in any suitable location proximate the light source 1130 so as to capture fluorescence or other emission spectra from the sample flow. For example, at least a portion of the imager array 1140 and at least a portion of the light source 1130 may be orthogonal to each other (e.g., one on a side wall of the chamber 1100, the other on an upper structure or lower structure of the chamber 1100). As another example, additionally or alternative, at least a portion of the imager array 1140 and at least a portion of the light source 1130 may be adjacent to each other (e.g., on the same surface such as on the upper structure or lower structure, in an alternating or other distributed pattern).

Lensless imaging may provide several advantages compared to conventional optical systems with lenses. For example, lensless image sensors may provide high resolution imaging over a large field of view. This may enable the imager array to successfully image a high number of PODS (e.g., over 100, or over 200) in the chamber in a single image frame. Furthermore, because lensless image sensors do not require focusing, there may be less need for precise optical alignment and positioning of optical components, thereby easing manufacturing processes and reducing burden on the user and/or software to adjust the focus of the imager array. The absence of lenses may also alleviate challenges with focal gradients that are common in lenses, and lowers overall part count and cost of the assay device. Accordingly, the incorporation of lensless image sensors in chamber arrangements (such as those described herein) may further enable dimensional scalability at low cost.

Figure 3:
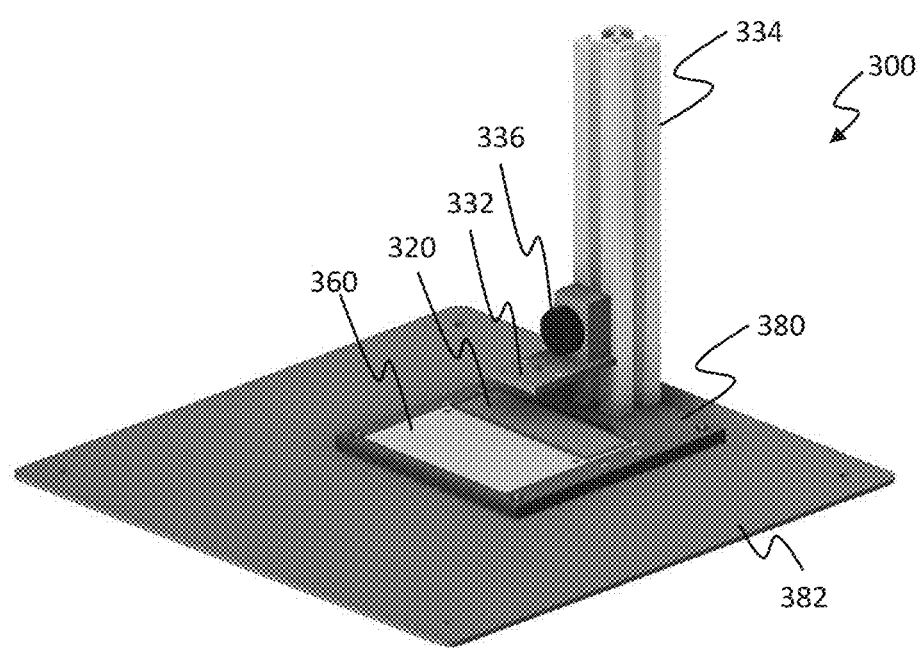
FIG. 3 depicts an exemplary variation of an assay system for optically processing samples.

The arrangement of the chamber, the one or more light sources, and the imager array may be constructed in various suitable manners. For example, FIG. 3 shows an exemplary variation of an assay system 300 for processing a sample. Generally, assay system 300 may include components similar to assay system 100 described above and shown in FIG. 1. As shown in FIG. 3, assay system 300 further includes one or more supports, including a base 380 and a light source post 334 coupled to the base 380. The base 380 may include a plate or other suitable stable surface for receiving a chamber 320, an imager array (not shown) underneath the chamber 320 and/or at least part of an electronics system 360. For example, the base 380 may include at least one recess shaped to complementarily receive the chamber 320, imager array, and/or electronics system 360. The chamber 320, imager array, and/or electronics system 360 may be coupled to the base 380 with fasteners, epoxy, interlocking mating features, and/or other suitable features. In some variations, the base 380 may be secured to a desktop, tabletop, or other suitable surface directly or indirectly (e.g., via a base mount 382 such as a secondary plate).

A light source post 334 may be mounted to the base 380 (e.g., with fasteners or interlocking features, etc.). In some variations, the light source post 334 may be vertical and mounted orthogonally to the base 380. A light source housing 332 may house a light source (e.g., LED, or coherent light sources such as a laser, or other suitable light source) and may be coupled to the light source post 334 (e.g., via a clamp or pin mechanism, etc.) such that that the light source is positioned over the chamber 320 on the base 380. The light source housing 332 may be adjustably coupled to the light source post 334 so as to enable adjustment of the relative positions of the light source and the chamber 320. For example, an adjustment knob 336 may be turned to loosen a clamp that couples the light source housing 332 to the light source post 334, such that the light source housing 332 may be adjusted vertically along the light source post 334. Upon the light source housing 332 being positioned in a desired location, the adjustment knob 336 may be tightened to secure the position of the light source housing 332 on the light source post 334. In other variations, other suitable mechanisms may enable adjustment of the light source housing (e.g., threaded attachments, one or more pins insertable in holes located at discrete heights, etc.). Furthermore, it should be understood that in some variations, the chamber 320 location may additionally or alternatively be adjusted (e.g., by moving the location of the base 380) relative to the light source. In some variations, the relative locations of the light source and the chamber are such that the light emitted from the light source are substantially collimated when incident on and entering the chamber. In one exemplary variation, the light source housed in the light source housing 332 may include one or more white light LEDs positioned at a distance of about six inches above the chamber mounted in the base 380.

An exemplary variation of a chamber arrangement is shown in FIGS. 4A-4D. As best shown in FIG. 4B, the chamber arrangement includes a chamber 400 with a first, upper structure 410 and a second, lower structure 430. For example, as shown in FIGS. 4A and 4C, the upper structure 410 may include a laminate composite including an optically transparent layer 412, a patterned structural layer 416 (e.g., copper or other suitable metal), and an adhesive layer 414 (e.g., acrylic adhesive) for bonding the optically transparent layer 412 and the structural layer 416 together. The lower structure 430 may include a laminate composite including an optically transparent layer 434, an upper patterned structural layer 432, a lower patterned structural layer 436, and adhesive layers 433 and 435 for bonding the optically transparent layer 434 to the upper and lower patterned structural layers, respectively. The optically transparent layer, structural layers, and adhesive layers in the lower structure 430 may be made of similar materials as the upper structure 410. Exemplary materials for at least part of one of the above-described optically transparent layers include polyimide and glass (e.g., flexible Willow® glass manufactured by Corning®, or other suitable glass material), other suitable optically transparent substrates, or any combination thereof.

As shown in FIG. 4A, one or more light sources 490 may be located on one side of the chamber volume, and an imager array 492 may be located on another side of the chamber volume opposing the one or more light sources 490. For example, one or more light sources 490 may be located above the upper structure 410 and directed to emit light toward the chamber volume. In some variations, a light source 490 may be an LED or other suitable light source embedded or placed within layers of the upper structure 410, while in other variations a light source 490 may be located external to the upper structure 410. An imager array 492 may be located below the lower structure 440 and directed to image the chamber volume. In some variations, the imagery array 492 may include one or more lensless CMOS image sensors. Alternatively, one or more light sources 490 may be located below the lower structure 430 and the imager array 492 may be located above the upper structure. Furthermore, although the chamber 400 is shown and described with the structures 410 and 430 being upper and lower structures, it should be understood that the orientation of chamber, light sources, and imager array may be different (e.g., the orientation may be rotated 90 degrees or 180 degrees from that shown in FIG. 4A).

The upper structure 410 and the lower structure 430 may be joined together, such that the upper structure 410 provides an upper surface of the chamber 400 and the lower structure 430 provides a lower surface of the chamber 400, as shown in the orientation of FIG. 4A. For example, the upper structure 410 and lower structure 430 may be bonded at least in part by an intervening adhesive layer 420, where the adhesive layer 420 may have a channel cutout 422 providing a central empty space for the chamber volume between the upper structure 410 and the lower structure 430. Registration features, such as alignment holes 470 in each of the upper structure 410 and lower structure 430, may facilitate alignment of the structures to form the chamber.

Figure 24A:
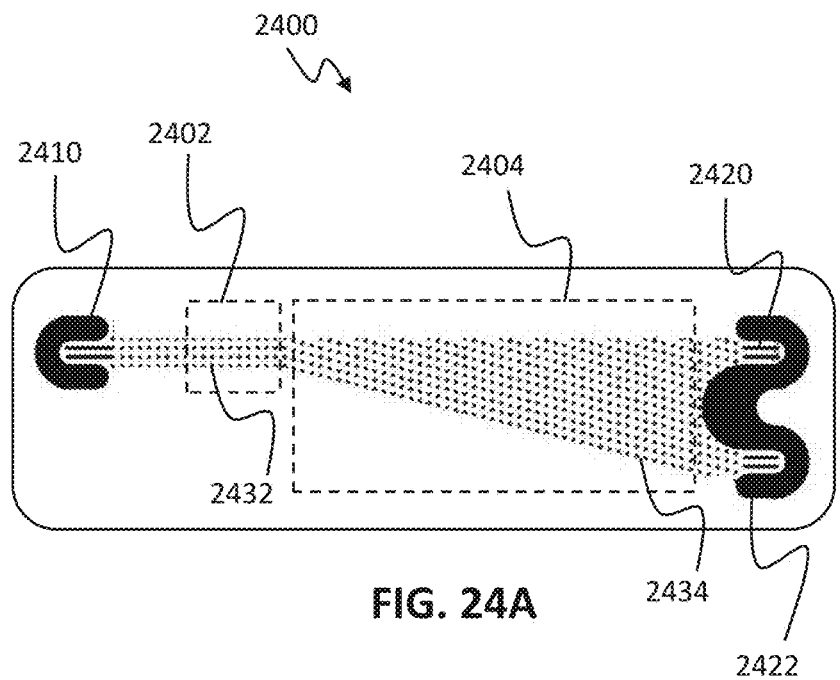
FIG. 24A depicts an illustrative schematic of an exemplary variation of an electromerging chamber arrangement.

One or more spacers may be located in the chamber volume to support the spacing between the upper structure 410 and the lower structure 430 and/or facilitate coupling of the upper structure 410 and the lower structure 430. As shown in the top plan view of FIG. 4D and the cross-sectional view of FIG. 4A, one or more boundary spacers 426 may form side walls of the chamber volume. For example, a boundary spacer 426 may be generally oval-shaped or rectangular-shaped (e.g., may include linear sides located on left and right sides of the chamber as shown in FIG. 4D). Furthermore, one or more spacer posts 424 may be arranged within the chamber volume. The spacer posts 424 may, in some variations, provide columnar support to enforce spacing between the upper and lower structures of the chamber. In some applications, the spacer posts 424 may additionally function to break up aggregated PODS, induce turbulence in sample flow, and/or other affect flow of the sample in the chamber. The spacer posts 424 may be distributed in a regular array (e.g., rectangular array as shown in FIG. 4D, staggered array as shown in FIG. 24A), or alternatively in an irregular array or other suitable pattern.

Although the boundary spacers 246 are depicted in FIG. 4D as elongated, linear strips, it should be understood that other shapes (e.g., wavy strips, irregular lengths) may be suitable. Furthermore, the boundary spacers 246 may be intermittently placed on the sides of the chamber, such as to accommodate additional sample inlets and/or outlets for the chamber between intermittent boundary spacers 246. Similarly, although the spacer posts 424 are depicted in FIG. 4A as having square cross-sections, it should be understood that in other variations, the spacer posts 424 may have other suitable cross-sections, such as circular or triangular.

In some variations, the spacers 424 and/or 426 may be formed from the patterned structural layers of the upper structure 410 and lower structure 430. For example, the patterned structural layer 416 of the upper structure 410 may adjoin the patterned structural layer 432 of the lower structure 430 such that the structural layers in combination form the spacers 424 and/or 426. In some variations, the structural layers 416 and 432 may be equal in thickness so as to each provide half of the height of the spacers. In other variations, the structural layers 416 and 432 may have different thicknesses (e.g., the structural layer 416 may be thicker or thinner than the structural layer 432). Alternatively, in some variations, the spacers 424 and/or 426 may be formed from any combination of layered structures. Furthermore, additionally or alternatively, non-layered components (e.g., beads) may provide spacing between the upper and lower surfaces of the chamber 400.

Figure 5:
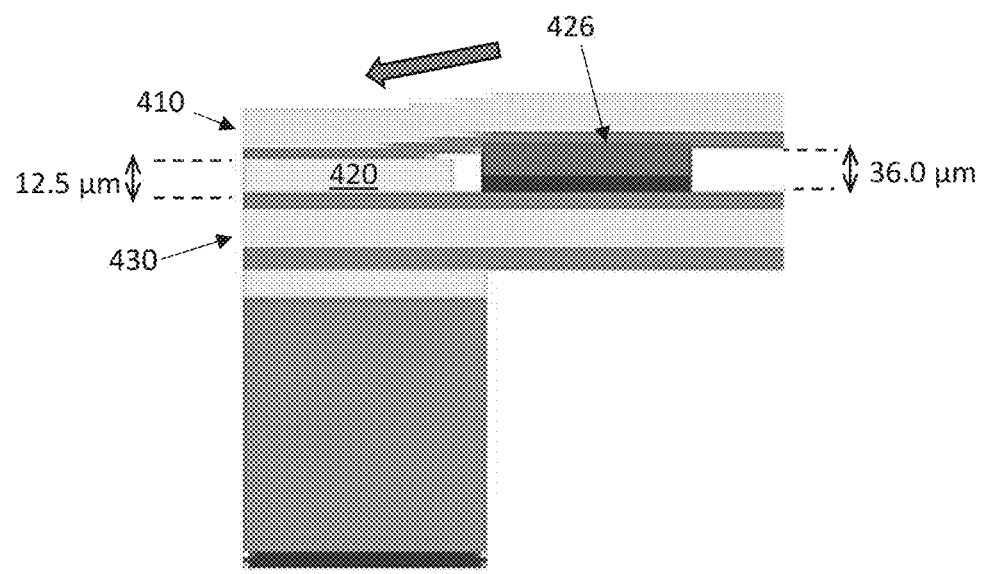
FIG. 5 depicts a detailed partial cross-sectional view of the chamber arrangement depicted in FIG. 4A.
Figure 6:
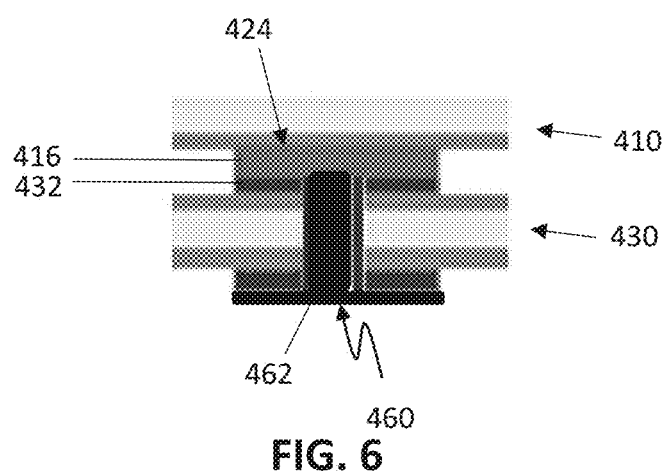
FIG. 6 depicts another detailed partial cross-section view of the chamber arrangement depicted in FIG. 4A.

In some variations, as shown in the detailed view of FIG. 5, the height of the spacers relative to the thickness of the intervening adhesive layer 420 between the upper structure 410 and the lower structure 430 may be selected to introduce a "stretched drum" effect on the upper structure 410 to enhance the coupling between the upper and lower structures and/or compress the patterned layers forming the spacers. For example, the height of the spacers 424 and/or 426 may be slightly greater than the thickness of the adhesive layer 420, such that the upper structure 410 is generally urged downward toward the lower structure 430 at the border of the chamber volume. This "stretched drum" effect may, for example, help compress the upper structure 410 and the lower structure 430 together and against the adhesive layer 420, so as to form a fluidic seal for the chamber volume. In some variations, the ratio between the height of the spacers and the thickness of the adhesive layer 420 may be between about 2 and about 4, or about 3.

Furthermore, as shown in FIG. 4A, at least some of the spacers may include a via 460 providing a passageway through the layers of the lower structure 430. The vias 460 may provide a passageway for an anchor material to bond the upper structure 410 and lower structure 420 together. For example, as shown in FIG. 4C, an anchor material 462 may be introduced into the via 460 to bond directly to the upper structure 410 and the lower structure 420, thereby joining the structures. In some variations, the anchor material may be solder or a polymer adhesive. In an exemplary method, the anchor material may be introduced into a via with the use of a patterned stencil having an opening aligned with the via (or multiple openings aligned with multiple vias). After placing the stencil over the via (e.g., on the underside of the lower structure 430), anchor material may be scraped over the stencil to force the anchor material into the via. Excess anchor material will stay on the stencil and be removed by removing the stencil and/or being wiped off the stencil, thereby leaving only anchor material in the via. Such anchoring may be used in addition to, or as an alternative to, the intervening adhesive layer 420 described above for bonding the upper structure 410 and the lower structure 420.

In addition to the upper and lower structures 410 and 430 described above, in some variations the chamber arrangement may further include a stiffener layer 450 and a stiffener adhesive layer 440 for bonding the stiffener layer 450 to the rest of the chamber 400 (e.g., to the underside of the lower structure 430). The stiffener layer 450 may provide structural support for manipulating and/or connecting components (e.g., port for a chamber inlet and/or chamber outlet) to the chamber 400. Like the first structure 410 and the second structure 430, the stiffener layer 450 and adhesive layer 440 may include reference features (e.g. holes 470) to enable alignments with the rest of the stackup layers. As shown in FIG. 4B, the stiffener layer 450 may include a channel cutout 456, and the adhesive layer 440 may include a channel cutout 442, where the channel cutouts 456 and 442 provide space for the imager array 492 in the fully assembled stackup. An additional structural layer 454 (e.g., copper or other metal) may also be bonded to the stiffener layer 450 for further structural support.

In an exemplary embodiment of the chamber arrangement shown in FIG. 4A, the upper structure 410 can include a one-sided copper-clad laminated composite (such as laminate composite LF8510 manufactured by DuPont™) including a 1 mm thick polyimide film that is bonded on one side facing the chamber volume to a 0.5 oz (18 µm thick) copper foil with an acrylic adhesive. The copper foil is patterned to form an oval-shaped boundary spacer and a plurality of partial spacer posts arranged in a rectangular grid inside the oval-shaped boundary. The lower structure 430 can include a dual-sided copper-clad laminated composite (such as laminate composite LF7005 manufactured by DuPont™), where an upper copper side facing the chamber volume is 0.5 oz (18 µm thick) copper foil and a lower copper side facing away from the chamber volume is 1 (36 µm thick) copper foil. The upper and lower structures of the chamber are flexible. A 12.5 µm thick polymer adhesive layer with an oval-shaped channel cutout is located outside the perimeter of the boundary spacer to bond the upper and lower structures of the chamber together. Both the upper and lower copper sides of the lower structure 430 are patterned to form a plurality of partial spacer posts, such that the facing patterned copper foil layers combine to form a plurality of spacer posts with 100 µm diameter circular vias. Solder in the vias, in combination with the polymer adhesive, anchor the upper and lower structures of the chamber together. Furthermore, the lower structure 430 may be strengthened such as with a stiffener backing. For example, a FR4 stiffener with copper foil on one side may be bonded to the underside of the lower structure 430, such as with a suitable adhesive (e.g., 1 mm thick polymer adhesive).

Figure 7A:
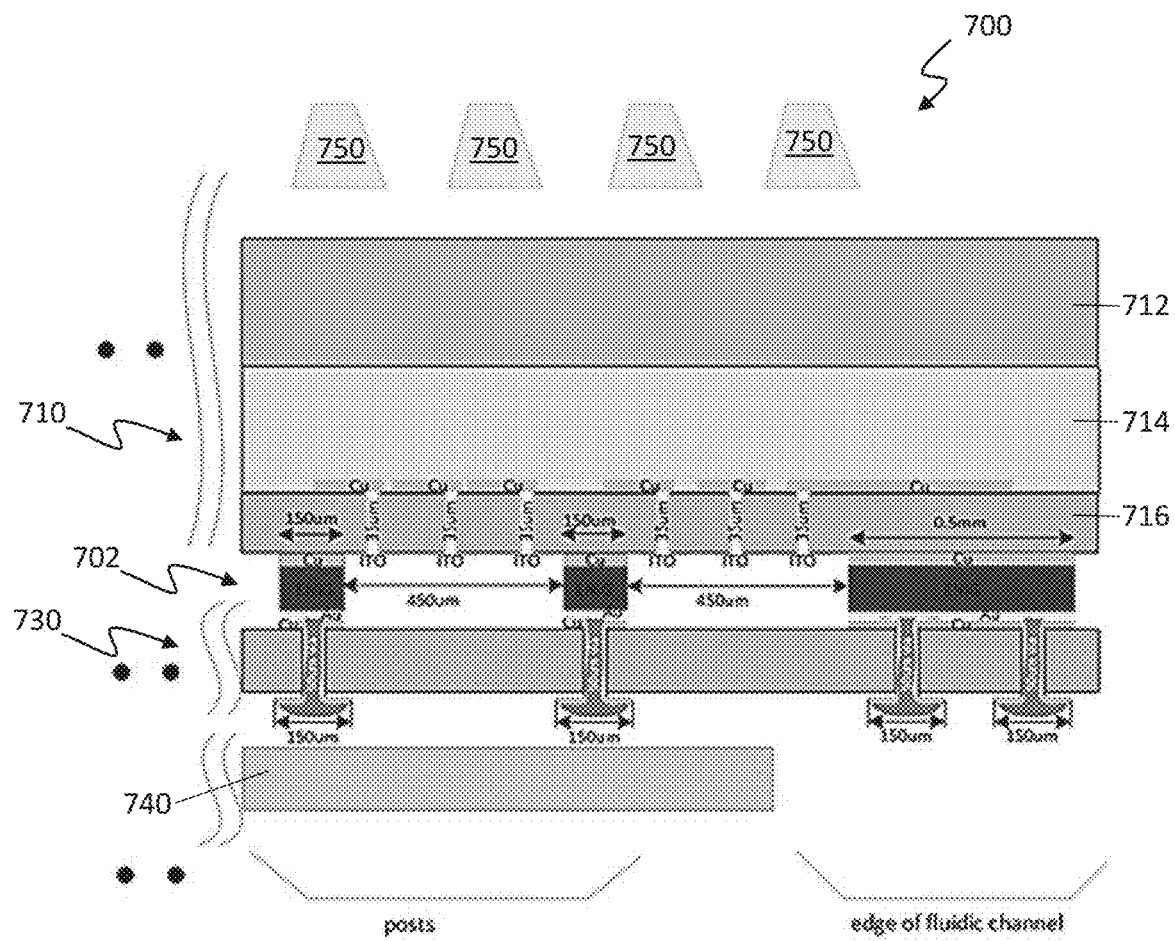
FIGS. 7A and 7B depict schematic illustrations of another exemplary variation of a chamber arrangement.
Figure 7B:
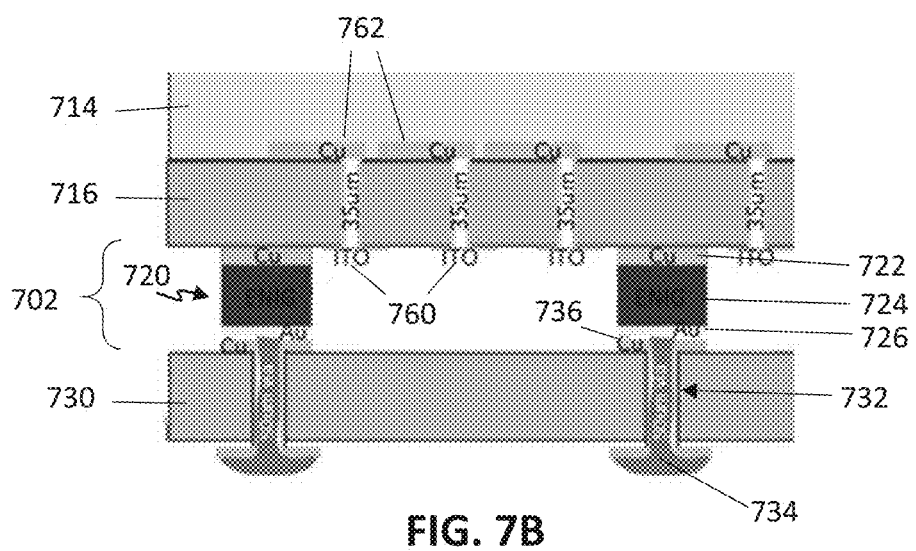

Another exemplary variation of a chamber arrangement is shown in FIGS. 7A and 7B. Similar to the chamber arrangement described above with respect to FIGS. 4A-4D, a chamber arrangement can include a chamber 700 including an upper structure 710 and a lower structure 730 offset from the upper structure 710. As shown in FIG. 7A, one or more light sources 750 may be located on one side of the chamber volume, and an imager array 740 may be located on another side of the chamber volume opposing the one or more light sources 750. For example, one or more light sources 750 may be located above the upper structure 710 and directed to emit light toward the chamber volume (e.g. gap 702). In some variations, a light source 750 may be an LED or other suitable light source embedded or placed within layers of the upper structure 710, while in other variations a light source 750 may be located external to the upper structure 710. An imager array 740 may be located below the lower structure 740 and directed to image the chamber volume. In some variations, the imagery array 740 may include one or more lensless CMOS image sensors. Furthermore, although the chamber 700 is shown and described with the structures 710 and 730 being upper and lower structures, it should be understood that the orientation of chamber, light sources, and imager array may be different (e.g., the orientation may be rotated 90 degrees or 180 degrees from that shown in FIG. 7A).

Similar to the chamber arrangements described above, the upper structure 710 and the lower structure 730 may be offset by a gap 702. The gap 702 may be supported or enforced by one or more spacers 720. Similar to the upper structure in the chamber arrangement shown in FIG. 4A, the upper structure 710 may include a multi-layer stackup. For example, the upper structure 710 may include a laminated stackup of an optically transparent material and adhesive (e.g., polyimide and an acrylic adhesive, or other suitable materials). Furthermore, the upper structure 710 may include material forming one or more spacers 720 (e.g., boundary spacers forming at least a portion of the boundary of the chamber, spacer posts located within the chamber volume). For example, a spacer 720 may include a plurality of bonded layers including copper 722, gold 726, and/or other surface plating 724 (e.g., electroless nickel immersion gold, or ENIG) that collectively form the spacer 720. Although the spacers 720 are depicted as including layers of material in the upper structure 710, it should be understood that the layers of material forming a spacer 720 may additionally or alternatively include layers of material in the lower structure 730.

As shown in FIG. 7B, the lower structure 730 may include may include an optically transparent material (e.g., polyimide) and one or more vias 732. A copper layer 736 may line vias 732. Similar to the vias in the chamber arrangement described above with reference to FIG. 4A, the vias 732 may accommodate anchor material 734 for bonding the upper structure 710 to the lower structure 730. For example, solder, adhesive, or another suitable anchor material may be deposited in one or more vias 732, and adjoin the upper structure 710 (e.g., the material forming the spacer 720) with the lower structure 730, thereby securing the upper and lower structures together.

As shown in FIG. 7B, the chamber 700 may include electrodes 760 that are exposed to the chamber volume and interact with sample flowing within the chamber. The electrodes 760 may be generally arranged as an array, for example. In some variations, at least some electrodes may be configured to measure electronic properties (e.g., impedance) of samples. Additionally or alternatively, at least some electrodes may be configured to generate an electrical field to enable dielectrophoresis. As shown in FIG. 7B, the electrodes 760 may be connected to conductive traces 762 (e.g., patterned copper). Such traces may be patterned to extend on a planar surface (e.g. into or out of the page relative to the cross-sectional view of FIG. 7B) and enable signals to pass to and from the electrodes 760. In other words, the electrodes 760 and their patterned electrical ads and traces may be directly integrated and electrically connected within the stackup, and may further be connected to electronics components (e.g., controller, processor, etc.) onboard the assay device or on one or more external computing devices.

In an exemplary embodiment of the variation shown in FIGS. 7A and 7B, a chamber arrangement may include an upper structure that includes a laminated structure of alternating polyimide and adhesive layers. The upper structure can include an upper polyimide layer 712 having a thickness of about 50 µm, an intervening adhesive layer 714 (such as acrylic adhesive LF0200 manufactured by DuPont™) having a thickness of about 50 µm, and a lower polyimide layer 716 having a thickness of about 25 µm. The chamber arrangement further includes a lower structure that includes a polyimide layer of about 25 µm. The upper and lower structures are offset from each other and separated by a set of spacers, thereby forming a chamber volume through which fluid can flow. A series of white LEDs are arranged to emit white light through the upper structure toward the chamber volume, and an imager array including lensless image sensors (e.g., one or more color CMOS sensors such as OV5640 manufactured by Omnivision Technologies Inc. with lenses removed) is arranged opposite the LEDs to image the contents of the chamber volume. The upper structure further includes a set of patterned copper, ENIG, and gold layers that form the spacers between the upper and lower structures. Lateral spacing of the spacers may be about 450 µm. Vias in the lower structure may receive solder material that extends through the lower structure to these spacers, thereby bonding the lower and upper structures together. Additionally, the solder may be manipulated to flow out laterally on the underside of the lower structure to form a flange-type feature, thereby further securing the lower and upper structures together. Furthermore, an array of exposed electrodes may be patterned into the side of the upper structure facing the chamber volume so as to interact with contents of the chamber volume. The electrodes may be made of indium tin oxide (ITO) or other suitable thin film conductor, and may be connected to copper conductive pads and traces patterned throughout the upper structure.

Figure 8A:
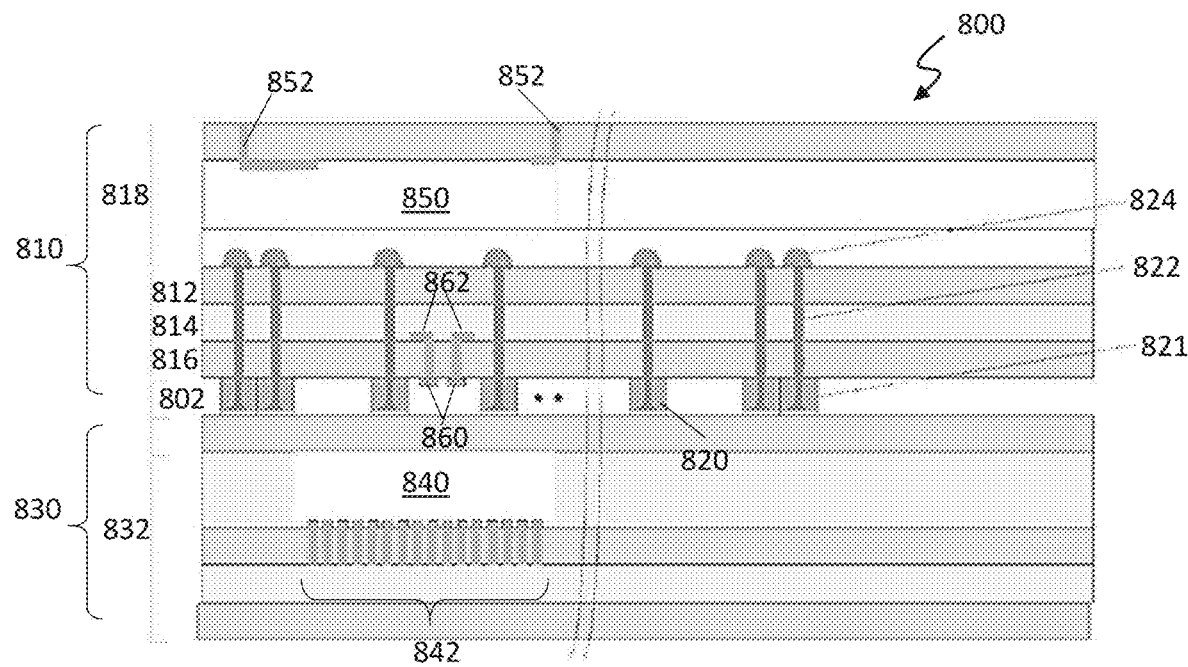
FIGS. 8A and 8B depict schematic illustrations of another exemplary variation of a chamber arrangement.
Figure 8B:
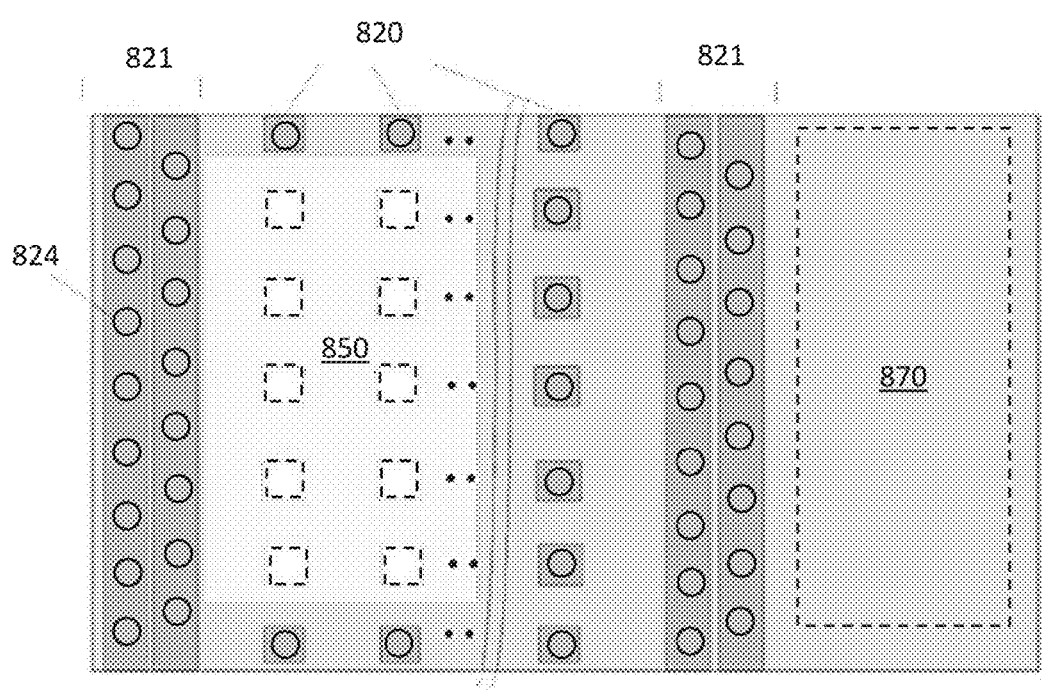

Another exemplary variation of a chamber arrangement is shown in FIGS. 8A and 8B. The chamber arrangement is similar to those described above with respect to FIGS. 4A-4D and FIGS. 7A and 7B, with additional details described below. For example, a chamber arrangement can include a chamber 800 including an upper structure 810 and a lower structure 830 offset from the upper structure 810 by a gap 802. The gap 802 may be enforced or supported by one or more spacer posts 820 and/or boundary spacers 821.

In the chamber arrangement shown in FIGS. 8A and 8B, one or more light sources 850 and the imager array 840 are embedded, or integrated, within the upper and lower structures of the chamber 800. Specifically, the upper structure 810 of the chamber 800 may include one or more layers of an optically transparent material (e.g., upper layer 812 and lower layer 816), laminated with an adhesive layer 814. The upper structure 810 may further include one or more lighting layers 818 within which at least one light source 850 and its conductive pads and/or traces 852 are located. The lighting layers may include, for example, stiffener material such as FR4 stiffener. Similarly, the lower structure 830 of the chamber 800 may include one or more layers of an optically transparent material (e.g., layer 830), and one or more imager layers 832 within which the imager array 840 and its conductive pads and/or traces 842 are located. Conductive traces 852 and 842 may pass to power source(s) and controller(s) for operating the light source 850 and passing signals to and from the imager array 840. For example, conductive traces may pass to an electronics region 870 of the assay device (e.g., disposed on an external surface of the upper structure, outside of the chamber 800) as shown in FIG. 8B, where the electronics region 870 may include electronic components relating to operation of the assay device. Suitable components include integrated circuits and passive components, power sources, controllers, processors, data transmitters, and/or memory, etc. In some variations, electronic components may process signals and communicate results to external computing devices and/or other peripheral devices.

Additionally, an electrode array including electrodes 860 may be patterned onto the upper structure 810 and/or lower structure 830 similar to that described above. Conductive pads and traces 862 may be further patterned into the structures and passed to the electronics region 870, or another suitable region with electrode control components.

Similar to the chamber arrangements described above, vias passing through parts of the stackup may receive an anchor material to couple the upper structure 810 and the lower structure 830. For example, the upper structure 810 may further include additional layers (e.g., copper) that are patterned to form spacer posts 820 and/or boundary spacers 821. The spacer posts 820 and/or boundary spacers 821 may include vias that receive a solder material extending through the layers 812-816 of the upper structure 810 and through the spacer materials, and bonding to the lower structure 830, thereby coupling the upper and lower structures.

In some variations, the chamber arrangement may comprise a substrate that includes and upper structure and a lower structure on different substrate portions, the substrate may folded such that the upper structure and the lower structure oppose each other. The folded substrate may be sealed to form a chamber between the upper structure and lower structure. Exemplary variations of such chamber arrangements are depicted by schematic illustrations in FIGS. 40A-40C, 41, and 42A-42B.

The chamber arrangement variations shown in FIGS. 40A-40E are similar to those described above, such as those described with respect to FIGS. 2A and 2B, FIGS. 7A and 7B, and FIGS. 8A and 8B, except with respect to the additional details described below. For example, a chamber arrangement can be a single piece fluid device which includes a chamber 4000 including a first structure 4010 and a second structure 4012 that are integrally formed (e.g., cut out or otherwise formed from the same substrate such as a flex film). The structures may be formed (e.g., deposited with thin film techniques, etc.) on different substrate portions connected by one or more flexible hinges 4029. The single piece fluid device may be foldable to create a sealed fluid chamber between the first and second surfaces, wherein the sealing may be accomplished after the folding by the application of small external clamping pressure by screws, spring clamps, toggle clamps, or any other suitable mechanical means (not shown). Additionally or alternatively, the first and second surfaces may be sealed by heating, adhesives, or any other suitable sealing process.

Figure 40A:
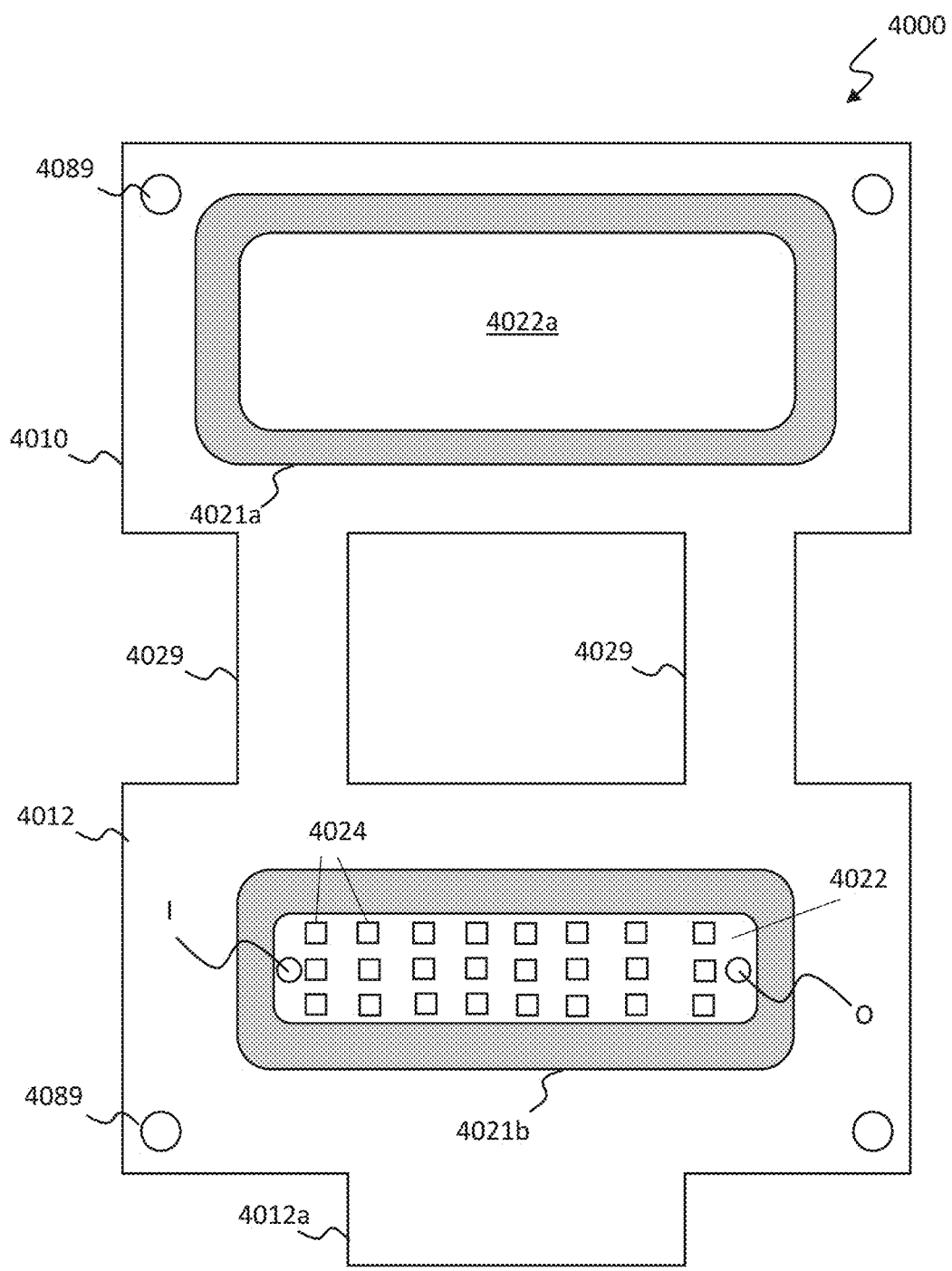
FIG. 40A depicts a top plan view of a variation of a chamber arrangement in an open state.

FIG. 40A shows a top plan view of an exemplary embodiment of the single piece fluid device in an unfolded state, showing the first structure 4010, and spacer posts 4024 provided in the channel 4022 of the second structure 4012. The first structure 4010 may act as a cover when the single piece fluid device is in a folded state (shown in FIG. 40E), and the spacer posts 4024 may be arranged in an array such as a rectangular array as shown and described when referring to FIG. 4A, for example, or in a staggered array as shown and described when referring to FIG. 23D, for example. Again, the spacer posts 4024 arranged in a staggered array may be configured to perform particle separation via deterministic lateral displacement (DLD). The single piece fluid device may be provided with alignment holes 4089, which may assist in alignment of the substrate portions upon folding (e.g., to help guide relative positions of the first and second structures), the placement of the device into any suitable device for the clamping or sealing of the first structure 4010 and the second structure 4012 together, etc. For example, the alignment holes 4089 of the second structure 4012 may be placed onto a clamping block (not shown), and the first structure 4010 may be folded onto the second structure 4012. The clamping block or any other suitable device may then be used to clamp and seal the structures together. The first structure 4010 and/or the second structure 4012 may be provided with a structure tab such as a second structure tab 4012a, which may aid in the handling of the first and second structures, for example.

Figure 40B:
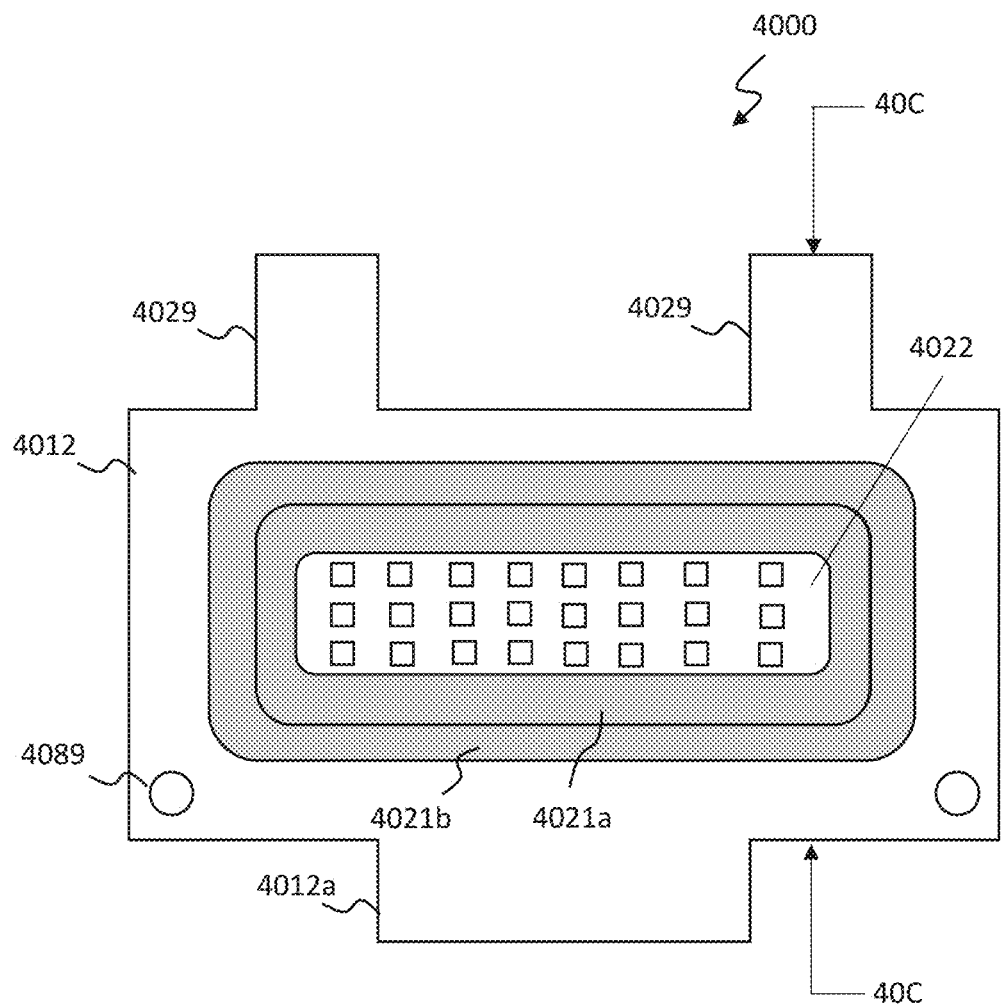
FIG. 40B depicts a top plan view of the chamber arrangement of FIG. 40A in a closed state.
Figure 40C:
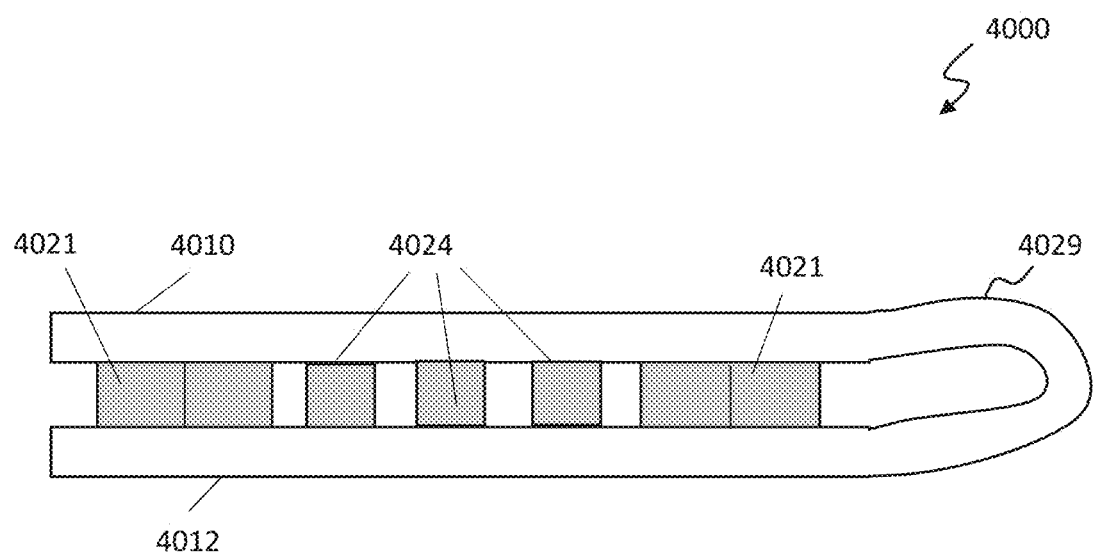
FIG. 40C depicts a cross-sectional side view of the chamber arrangement shown in FIG. 40B, taken along the line 40C:40C.
Figure 41:
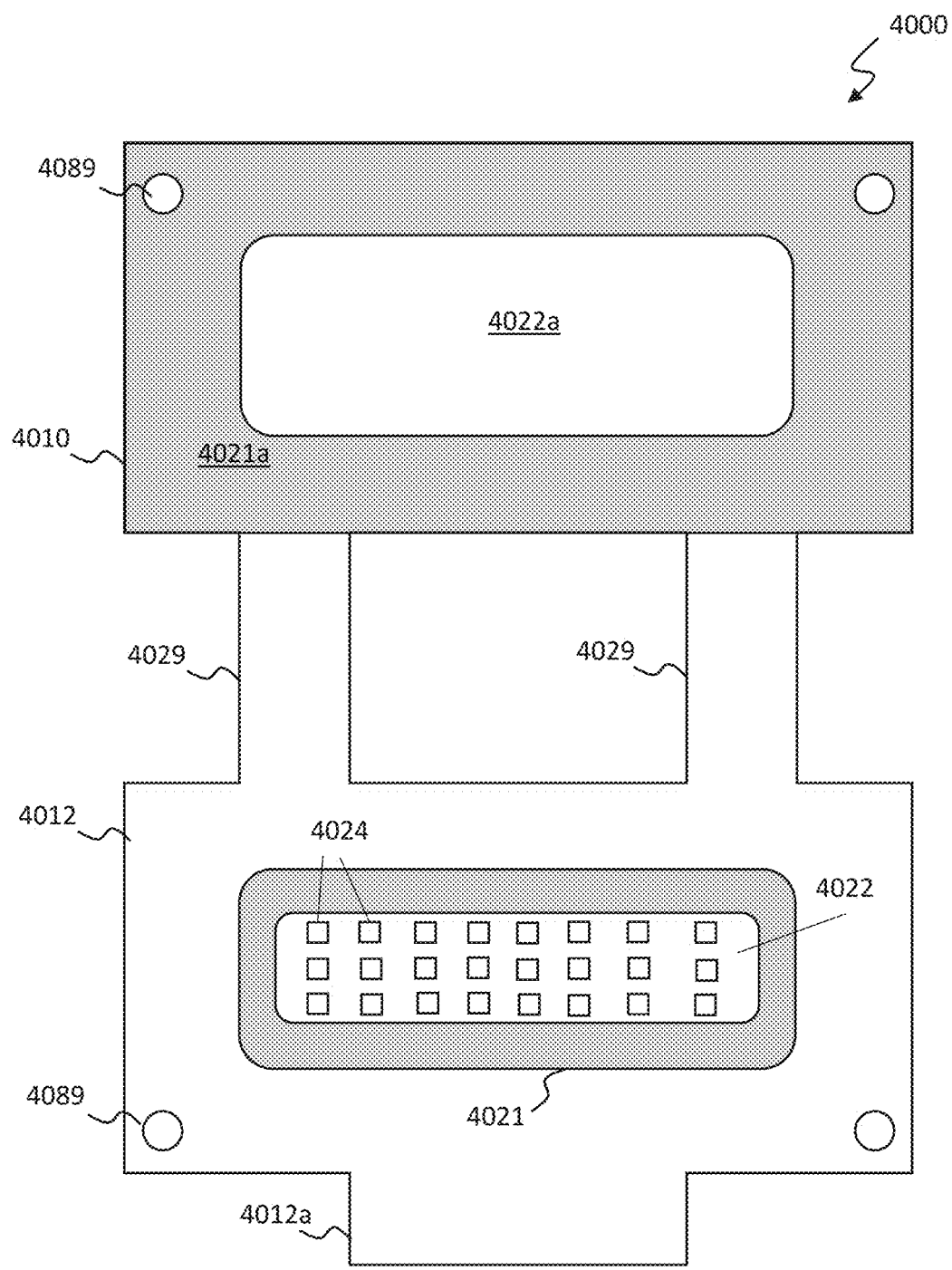
FIG. 41 depicts a top plan view of another variation of a chamber arrangement in an open state.

Boundary material (referred to herein as "boundary material" or "boundary spacers") may be provided within first structure 4010 and/or the second structure 4012. After the substrate is folded, such boundary material may form at least a portion of a perimeter of the sealed chamber. It should be understood that the boundary material may extend along a perimeter of the second structure 4012 such that the channel 4022 may be sealed from all its sides. In some variations, the boundary material may be provided within both the first structure 4010 and the second structure 4012, in any suitable pattern. In the exemplary embodiment of the chamber arrangement shown in FIG. 40A, the first structure 4010 is provided with a ring-shaped boundary material 4021a, which may receive and encircle the boundary material 4021b of the second structure 4012 when the device is in a folded state (FIG. 40B). The channel 4022 may thus be placed in the recess 4022a of the first structure 4010, within the boundary material 4021a. In the exemplary embodiment of the chamber arrangement shown in FIG. 40C, the first structure 4010 may be provided with boundary material 4021a throughout the structure, wherein the boundary material 4021a extends throughout the cover with the exception of the recess 4022a. The boundary material 4021b of the second structure 4012 and the channel 4022 may, as in the embodiment shown in FIG. 40A, be placed in the recess 4022a when the device is in the closed state. FIG. 40C shows a cross-sectional view of the single piece fluid device of FIG. 40A in a folded state. When the single piece fluid device is in a fully folded state, the fluid channel may be sealed. As shown in FIG. 40A, at least one inlet ("I") and at least one outlet ("O") for the fluid chamber 4022 may provide fluidic access to the fluid chamber 4022 from one of the first and second structures, such as the second structure 4012 of the single piece fluid device, for example.

In other words, in some variations, at least a portion of boundary material in the first structure and at least a portion of the boundary material in the second structure may be complementarily formed so as to mate when the chamber arrangement is in the closed state, and form a sealed chamber within the mated boundary material. Furthermore, it should be understood that different portions and patterns of the boundary material may be provided in the first and second structure of the chamber arrangement, in addition to the exemplary patterns shown in FIGS. 40A and 40C.

Figure 42A:
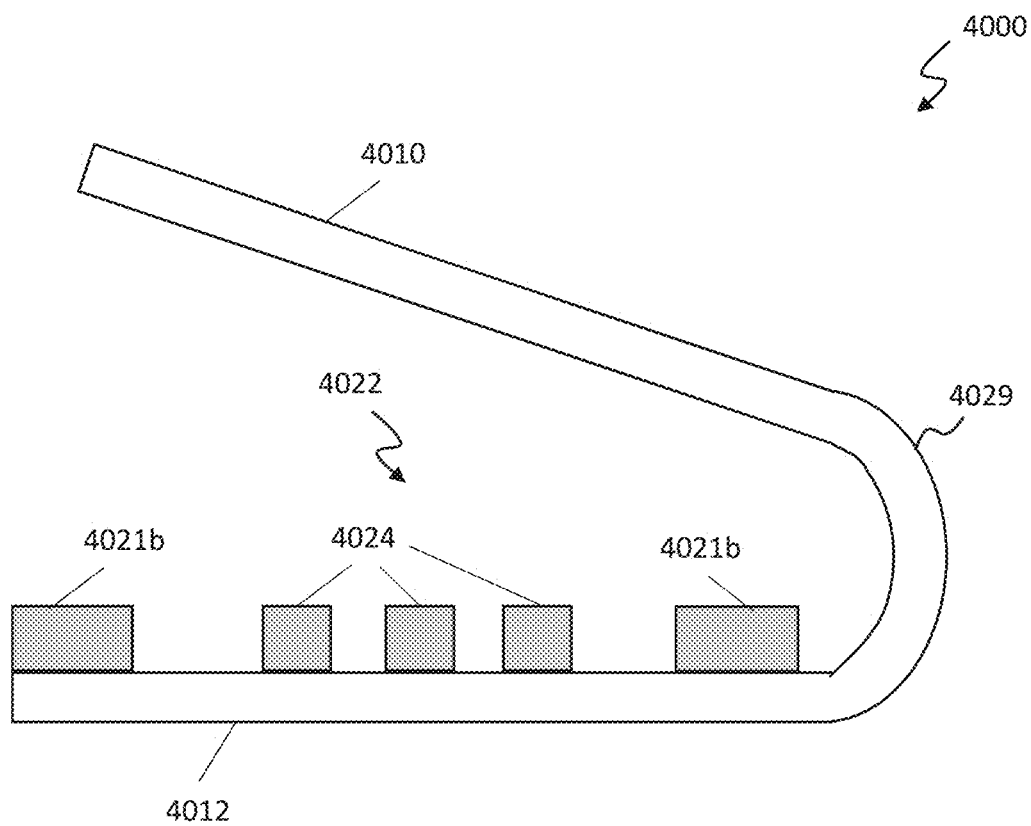
FIGS. 42A and 42B depict cross-sectional side views of another variation of a chamber arrangement in a partially closed state and a closed state, respectively.
Figure 42B:
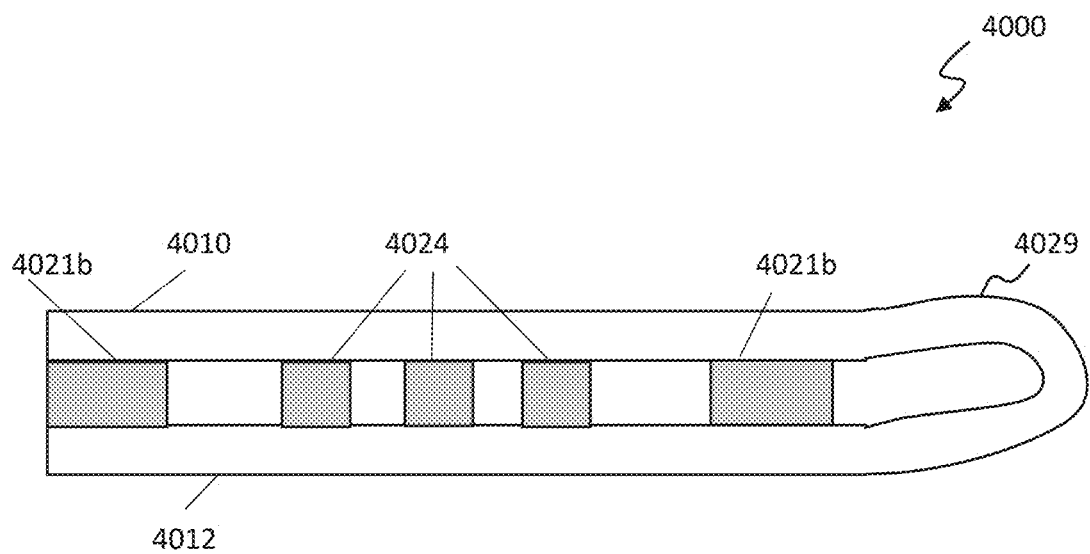

In some variations, all of the boundary material may be provided in one of the first and second structures. For example, as shown in the side cross-sectional views of a chamber arrangement depicted in FIGS. 42A and 42B (showing partially closed and closed states, respectively), the boundary material 4021b may be provided solely within the second structure 4012, while the first structure 4010 may form a cover without boundary material deposited thereon. As shown in FIG. 42B, the first structure 4010 may lie flush against the top of the boundary material 4021b (and spacers 4024) when the device is in the closed state. Again, as previously described, when the single piece fluid device is in a fully closed state, the fluid chamber 4022 may be sealed.

Although specific exemplary variations of chamber arrangements are described above with references to FIGS. 2A-8B and FIGS. 40A-40C, 41, and 42A-42B, it should be understood that various features of these chamber arrangements may be combined in any suitable manner.

Electromerging Chamber

In some variations, the chamber may be configured to alter at least a portion of the sample in the chamber, such as by merging two or more entities or particles in the sample through application of electrical energy by electrodes ("electromerging"). Such electromerging may, as described in further detail below, enable further processing such as sorting and separating particles by size in order to efficiently isolate certain particles of interest for further processing. For example, electromerging chamber arrangements may be used to identify and sort cells of interest, such as cells (e.g., hybridomas, B cells, Chinese hamster ovary (CHO) cells, etc.) that are high secretors of desired substances such as specific antibodies or insulin for development of immunotherapy treatments, etc.

Figure 23A:
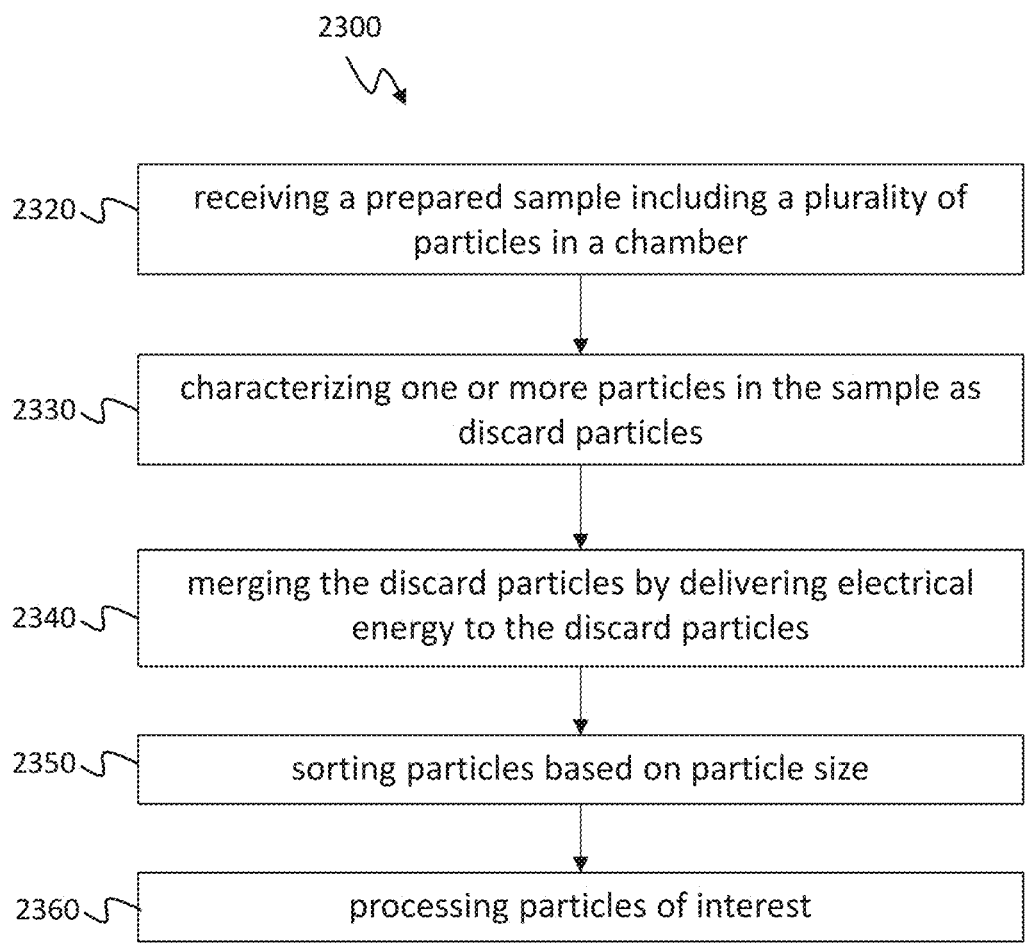
FIG. 23A depicts a flowchart of an exemplary method for processing samples with electromerging.

For example, as shown in FIG. 23A, a method 2300 of processing a sample may include receiving a prepared emulsion including a plurality of particles in a chamber 2320, characterizing one or more particles in the sample as discard particles 2330, merging at least a portion of the discard particles 2340 by delivering electrical energy to the discard particles, and sorting particles based on particle 2350. Further processing 2360 may be performed on certain particles of interest, such as collecting particles of interest into a reservoir, pipetting or otherwise depositing PODS or cells into a well plate, performing cellular PCR, DNA sequencing, ELISA, FACS, and/or other processing, etc.

Figure 23B:
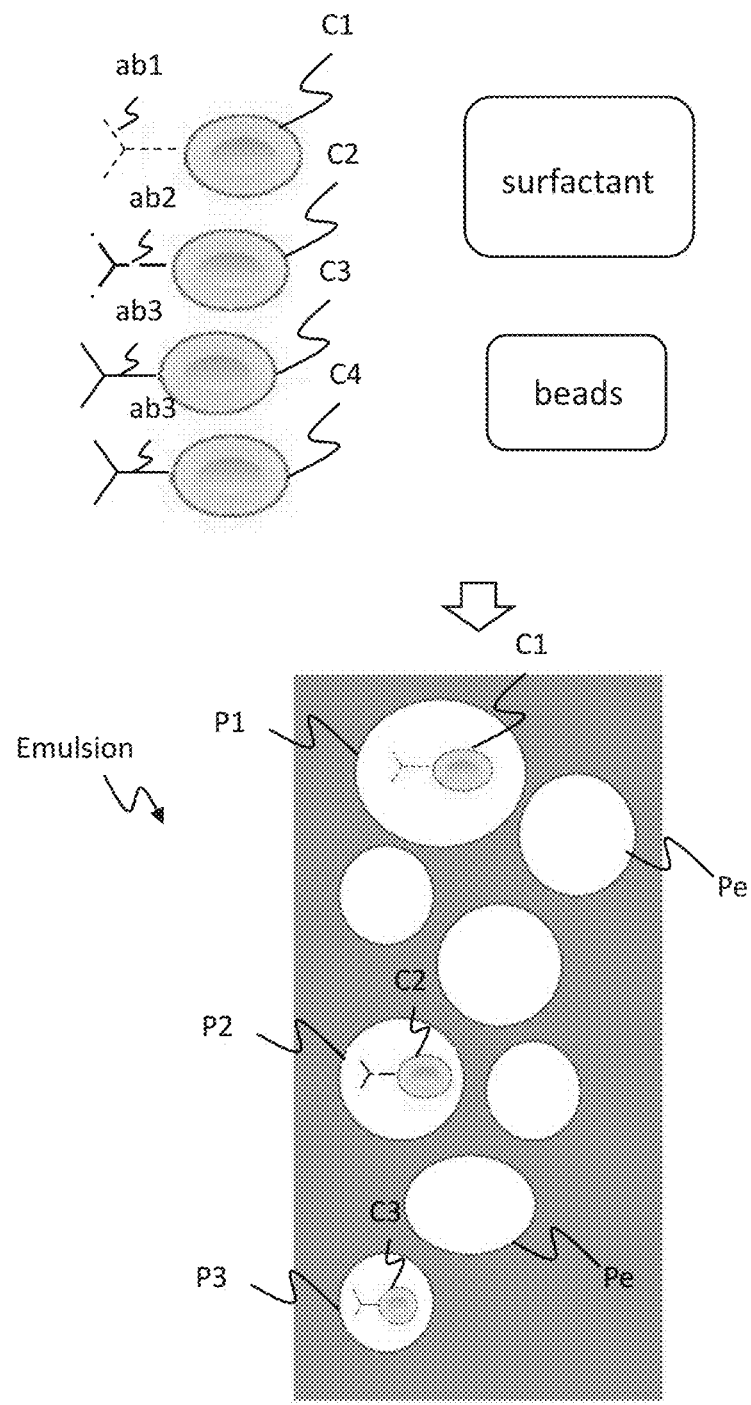
FIG. 23B depicts an illustrative schematic of an exemplary variation of preparing a sample.
Figure 31:
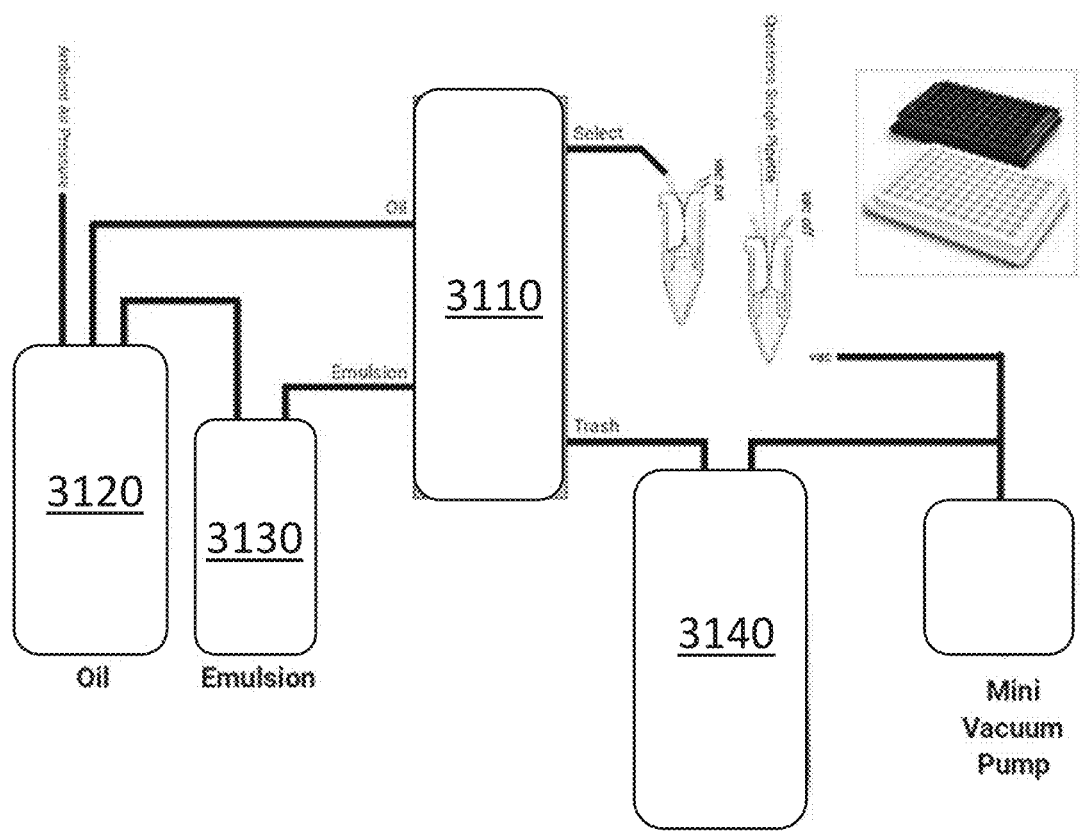
FIG. 31 depicts an illustrative schematic of an exemplary variation of a system for processing samples with electromerging.

FIG. 23B depicts an exemplary schematic of preparation of a sample including particles (e.g., PODS) of interest among a plurality of particles. Specifically, in this example, the sample includes cells mixed with a surfactant (e.g., fluoro-oil) and beads or other markers to create an emulsion with PODS, where each POD may function as a self-contained vesicle. For example, as shown in FIG. 31, fluoro-oil 3120 may be added to an emulsion 3130, and the emulsion 3130 may be introduced into an electromerging chamber 3110. Oil 3120 may additionally be introduced separately into the electromerging chamber 3110. The sample may be polydisperse with PODS of different sizes. A cell may secrete one or more antibodies. For example, as shown in FIG. 23B, cell C1 may secrete a first type of antibody (ab1), cell C2 may secrete a second type of antibody (ab2), and cells C3 and C4 may secrete a third type of antibody (ab3). These cells may be mixed with beads coated with antigens specific to an antibody type of interest (e.g., ab3) such that in the mixed sample, the beads bind to secretor cells of interest, and the resulting agglutination may be an indicator of the presence of the cells of interest and/or of the level of secretion by the cells of interest. In the resulting emulsion, each POD may include at least one cell (which may or may not be a cell of interest) or lack cells. For example, PODS P1-P3 may include cells C1-C3, respectively, while other PODS (Pe) may lack cells. In some variations, the ratio of cells to surfactant may be low so as to produce a relatively dilute concentration of PODS with cells. For example, the average number of cells per POD ($\lambda$) may be between about 0.9 and about 1.1, or about 0.1 (e.g., about 10 "empty" PODS without cells for every 1 POD with at least one cell). Furthermore, only a fraction of these cells may be cell of interest (that is, secreting an antibody of interest), and only a fraction of those cells may be desirable cells of interest (that is, secreting the antibody of interest at a sufficiently high rate) suitable for further processing such as for immunotherapy. Exemplary systems and methods for extracting the desirable cells of interest from the emulsion are further described below with respect to FIGS. 23A-24B. FIG. 31 illustrates another exemplary variation of the system.

One advantage of the electromerging chamber arrangement combined with PODS is that each POD serves as a low volume vesicle (e.g., between about 500 picoliters-1 nanoliter in volume, on average) which enables readout and identification of a low amount of antibodies (or other substance of interest). In some variations, cells of interest may require only up to a few hours to grow and secrete before they are suitable for identification and sorting with the electromerging chamber arrangement. As an illustration, FIGS. 25A-25C are images depicting hybridoma growth (with IgG clustering) over time in a cell secretion assay, as captured by an imager and chamber systems such as that described herein. At time t=0, no agglutinates are visible (FIG. 25A). At this time, the concentration of IgG is low and below a secretion range, as suggested by the visual similarities between FIG. 25A and FIG. 26A (IgG concentration 0.5 ng/ml). However, after a mere two hours at time t=2 hours, hybridoma growth is already reflected by a sufficiently high concentration of IgG within a hybridoma secretion range, as suggested by the visual similarities between FIG. 25B and FIG. 26B (IgG concentration 5 μg/ml). A few more hours of growth at time t=6 hours results in IgG clustering that is even more easily detectable using the imaging and chamber systems described herein. Accordingly, the electromerging chamber arrangement may provide a significantly faster method of producing antibodies or other substances of interest, in contrast to conventional production protocols which may require many days (e.g., 10-14 days) of careful incubation during which cells must be cloned and grown to sufficiently amplify the signal associated with agglutination.

Additionally, the sample may be introduced into the electromerging chamber arrangement as continuous flow, thereby enabling high throughput. Furthermore, the output of the electromerging chamber arrangement has less dilution of particles of interest in the outputted fluid volume. For example, in some variations, each well of a well plate may receive a single POD which is known to contain a high secretor cell drawn from the outputted fluid volume, compared to conventional production protocols which typically result in many empty wells along with a few wells containing useful cells.

Figure 23C:
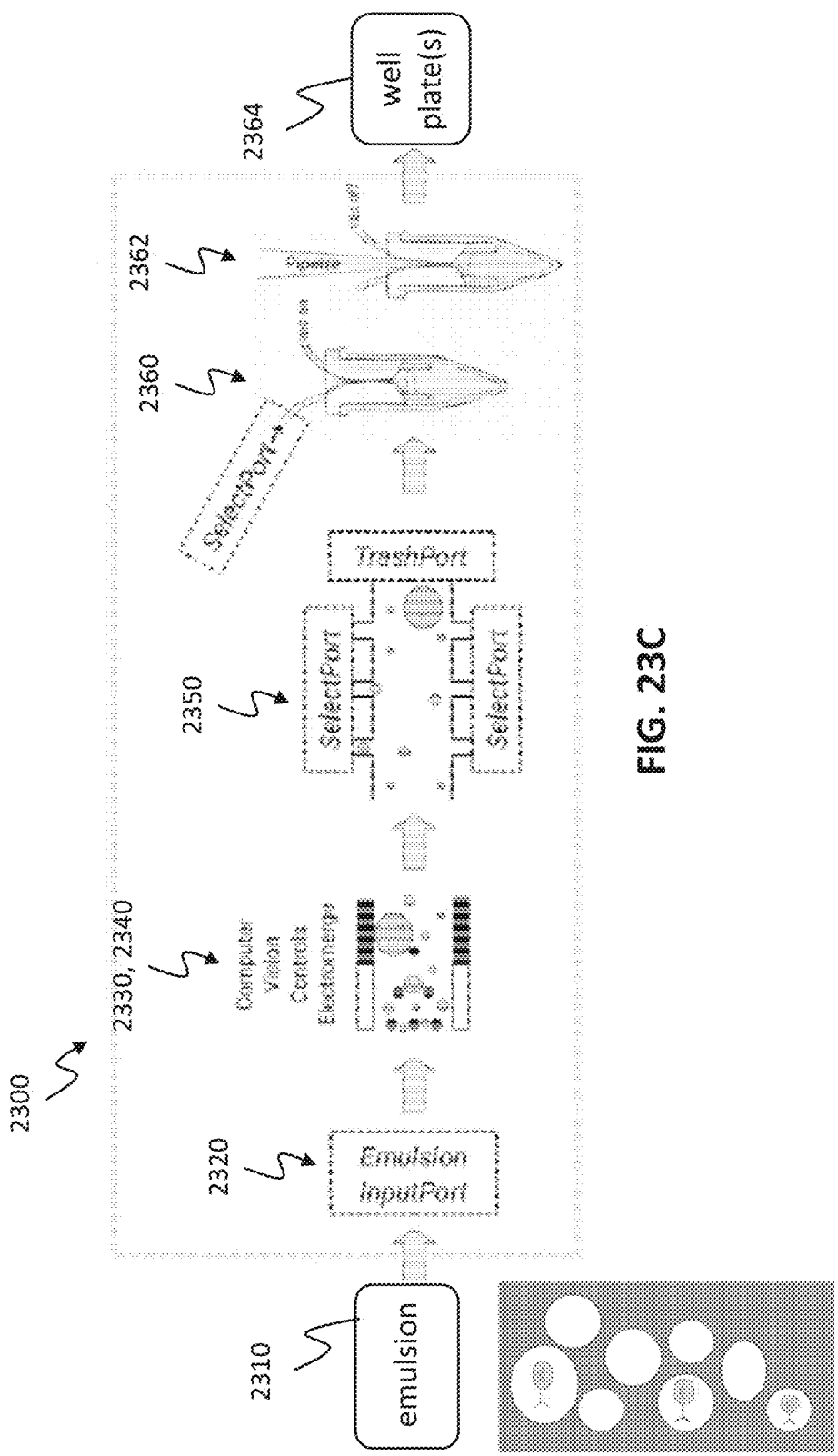
FIG. 23C depicts an illustrative schematic of an exemplary variation of a method for processing samples with electromerging.

Generally, as shown in FIGS. 23C and 31, the sample may be introduced into a chamber similar to chambers discussed above, except that the chamber includes one or more electrodes in the flow path of the sample. As described above with respect to FIG. 23A, processing in the chamber may be characterized as a multi-step process, including characterizing, merging, and sorting PODs. For characterizing PODS, an imager array may obtain one or more images of the PODS in the sample, and the images may be analyzed using computer vision and/or other computational techniques such as those described above, to characterize PODS based on their content (2330). For example, some PODS may be characterized as PODS of interest (e.g., containing cells that secrete antibodies of interest and/or that secrete the antibodies of interest at a sufficiently high rate) based on amount of agglutination present in the PODS. Other PODS may be characterized as PODS for discard.

PODS characterized as discard PODS may then be merged to form larger PODS that are also intended for discard, by delivering electrical energy from one or more electrodes in contact with the discard PODS (2340). Electrodes and discard PODS may be capacitively coupled such that variations in voltage applied by the electrodes cause mechanical disturbances or other forces on the surfactant surfaces of PODS, thereby breaking the surface and causing adjacent PODS to rupture and merge together. For example, the electrodes in contact with the PODS may be driven with an AC waveform such that the alternating modulation causes a cyclical mechanical compression and decompression of the PODS surfactant surfaces, thereby causing the PODS to rupture and merge. Suitable AC waveforms include those described in further detail below with respect to FIG. 24B. Accordingly, the merging process (2340) may produce an emulsion in which PODS of interest are generally smaller, while PODS intended for discard are generally larger.

Figure 28A:
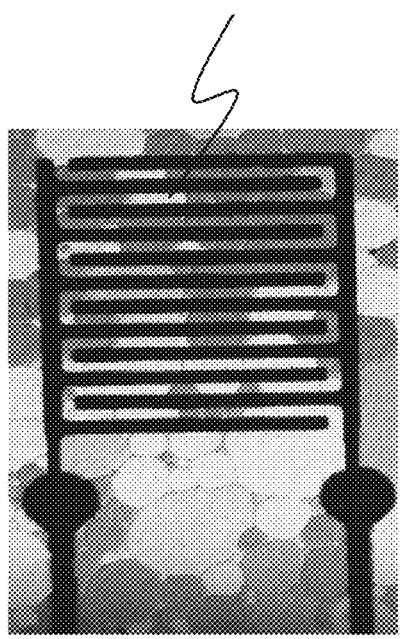
FIGS. 28A and 28B depict another variation of electrodes in an exemplary variation of an electromerging chamber arrangement.
Figure 28B:
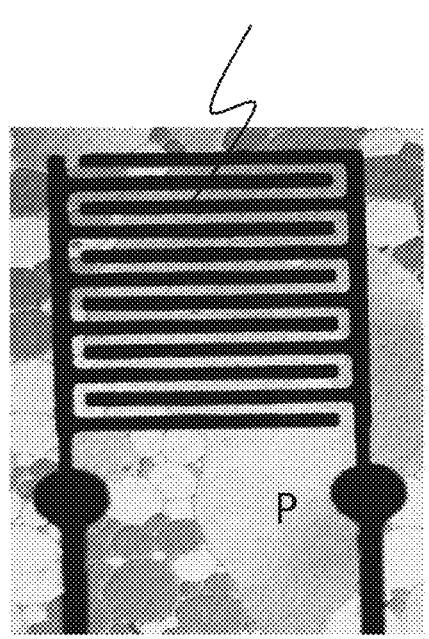

The electrodes in the chamber may have any suitable shape and/or orientation suitable for delivering electrical energy to particles in the chamber. For example, the electrodes may be spacer posts 2402 (as shown in FIGS. 24-24C, for example) extending transverse to the sample flow direction, such as extending between upper and lower surfaces of the chamber. As another example, the electrodes may be interdigitated electrodes 2810 as shown in FIGS. 28A and 28B, which are patterned on a lower and/or upper surface of the chamber. In this example, FIG. 28A depicts PODS prior to delivery of electrical energy via the interdigitated electrodes 2810, and FIG. 28B depicts PODS including a larger, merged POD (P) that was created after delivery of electrical energy via the interdigitated electrodes 2810.

Figure 23D:
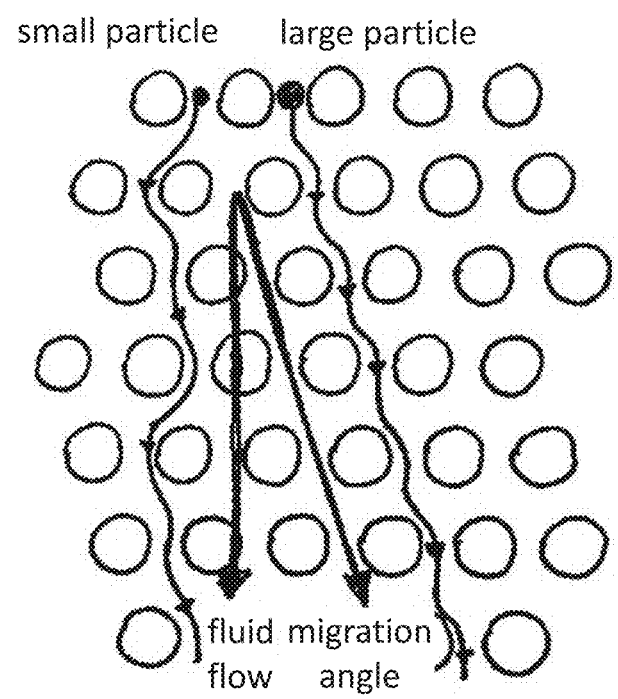
FIGS. 23D and 23E illustrate exemplary variations of sorting arrangements in a chamber for processing samples.

Following such merging, the PODS in the emulsion may be sorted (2350) based on size in order to filter and isolate the PODS of interest which are generally smaller. The sorting may be accomplished by any suitable sorting arrangement. In some variations, the sorting arrangement may include a passive sorting arrangement. For example, the sorting arrangement may include multiple spacers (e.g., similar to spacer posts 424 as in the chamber shown in FIG. 4A), which may be arranged in a staggered array and configured to perform separation via deterministic lateral displacement (DLD). In DLD, a staggered array of posts may work similar to a marble machine to separate small and large particles such as PODS. For example, as shown in FIG. 23D, as a sample including small and large particles generally move in a direction of fluid flow through the staggered array of posts, large particles (that is, particles over a critical threshold diameter) may be steered laterally relative to the fluid flow direction. Such passive migration of the larger particles may thus enable separate collection of smaller particles (e.g., at a first outlet) and larger particles (e.g., at a second outlet). The critical threshold diameter for sorting particles in this manner may be adjusted, for example, by tailoring the diameter and/or spacing of the posts. Accordingly, in some variations of a sorting arrangement, spacer posts in the chamber may be constructed and arranged so as to passively sort PODS in the sample by deterministic lateral displacement.

Figure 30:
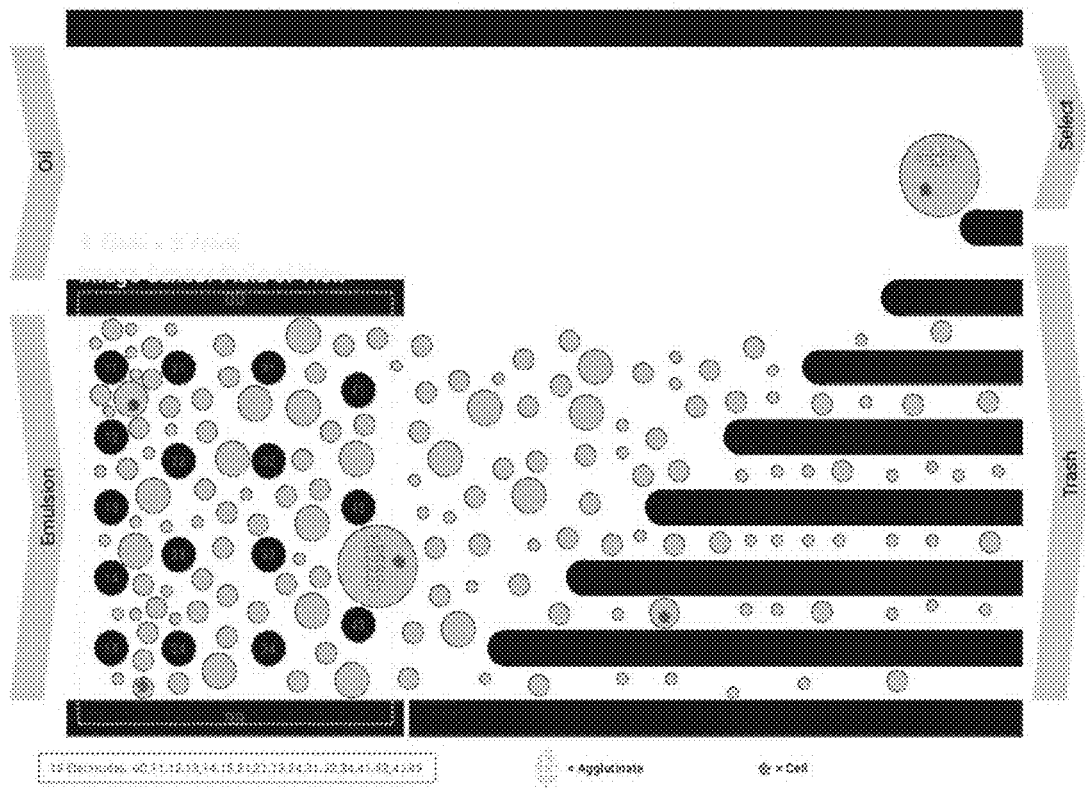
FIG. 30 depicts an illustrative schematic of another exemplary variation of an electromerging chamber arrangement.

As another example, the sorting arrangement may include one or more outlets of various sizes that selectively permit passage of differently-sized particles. For example, as shown in the schematic of FIG. 23C, the chamber may include multiple small outlets (e.g., one or more selection channels leading to capture at a "SelectPort") configured to only permit passage of particles below a predetermined threshold particle size, and reject passage of particles above the predetermined threshold particle size. One or more larger outlets ("TrashPort") leading to a waste receptacle may be configured to permit passage of larger particles that were rejected by the preceding smaller outlets. Thus, in a chamber such as that shown in FIG. 23C, smaller PODS may tend to exit the chamber through smaller outlets, before reaching the larger outlet(s) for discard with the larger PODS. As another example, as shown in the schematic of FIG. 30, multiple channels leading to one or more outlets leading to a waste receptacle ("Trash") may reject passage of larger particles, which may be guided by channels toward a capture receptacle ("Select") that accepts passage of larger particles. Accordingly, in some variations of a sorting arrangement, an array of progressively increasing chamber outlet sizes may passively sort PODS in the sample through collection according to particle size. As shown in FIGS. 23C and FIG. 31, particles not of interest may be collected for discard (e.g., a waste receptacle at "TrashPort" shown in FIG. 23C, or waste receptacle 3140 shown in FIG. 31). Furthermore, in some variations, fluidic currents (e.g., constructed through use of pumps, valves, chamber surface contouring, etc.) may, additionally urge particles toward the smaller outlets (e.g., against sidewalls of the main channel) to further encourage sufficiently small particles to pass through the smaller outlets.

Figure 23E:
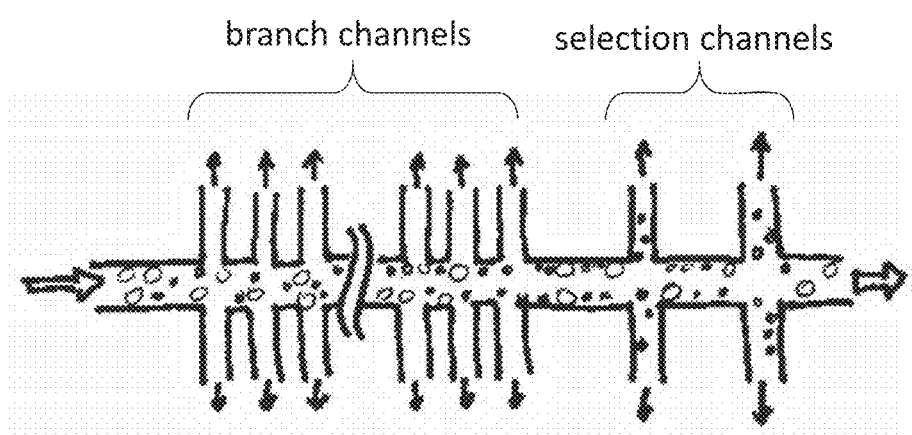

As another example, as shown in FIG. 23E, the sorting arrangement may additionally include multiple branching channels configured to perform particle separation via hydrodynamic filtration. In hydrodynamic filtration, a small amount of fluid is withdrawn repeatedly from the main channel through one or more side branching channels, which gradually concentrates and aligns particles along the sidewalls of the main channel. The concentrated and aligned particles can then be collected according to particle size through one or more selection channels, similar to that described above and shown in FIG. 23C.

Additionally or alternatively, the sorting arrangement may include an active sorting arrangement. For example, the chamber may include one or more electrode regions configured to generate electrical fields to enable dielectrophoresis, such as similar to those described in U.S. patent application Ser. No. 15/986,416 which was incorporated by reference above. Such electrode regions may, for example, be operated to capture, move, and/or otherwise actively control sorting of selected PODS.

After sorting PODS and collecting PODS of interest, the PODS of interest may be further processed. For example, the smaller PODS of interest may be directed (e.g., via vacuum or other aspects of a fluidic control system as described below) into a reservoir (2360), from which individual PODS or cells may be withdrawn (2363) with a pipette or other instrument. PODS of interest may be deposited into well plates for further processing and/or analysis (e.g., PCR, sequencing, etc.). For example, up to a single cell may be deposited in each well. A programmable robot may automatically load each well, thereby further increasing efficiency.

Figure 24B:
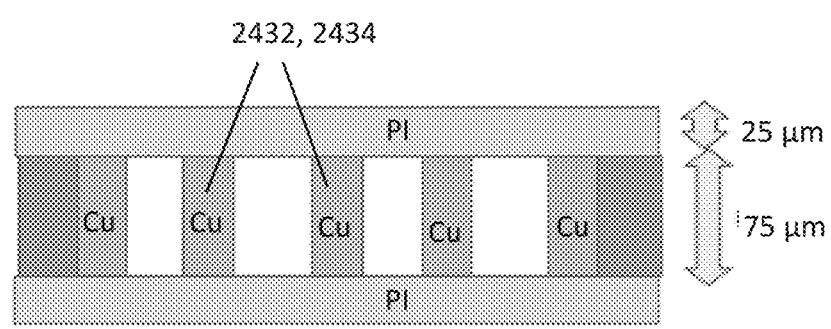
FIG. 24B depicts an illustrative schematic of a cross-sectional stack-up of the variation of the electromerging chamber arrangement depicted in FIG. 24A.
Figure 24C:
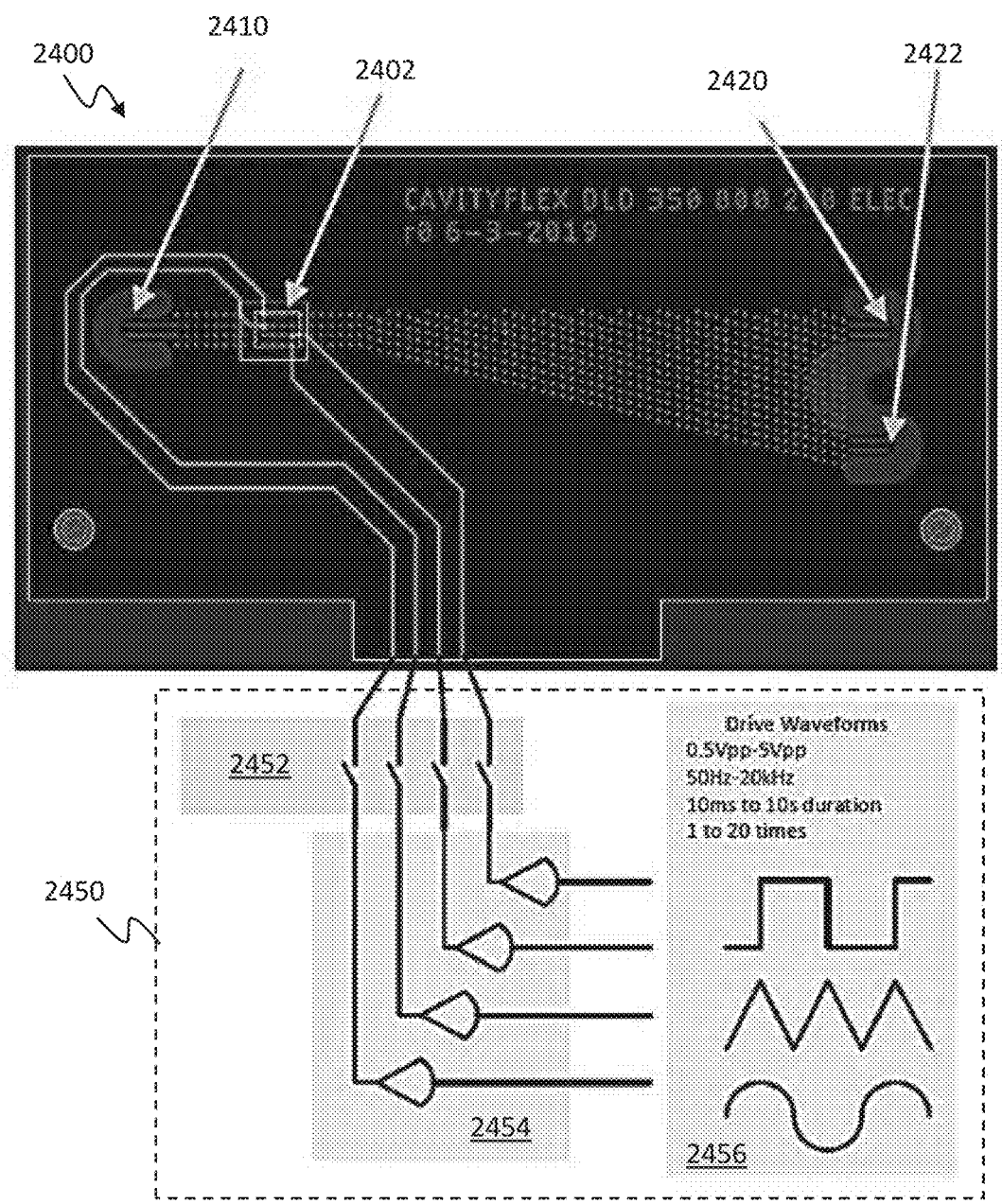
FIG. 24C depicts an illustrative schematic of an exemplary variation of an electromerging chamber arrangement and a controller.

FIGS. 24A-24C are schematic illustrations of an exemplary variation of an electromerging chamber arrangement. As shown in FIG. 24A, a system for processing a sample may include a chamber 2400 including at least one inlet 2410 for receiving a sample (e.g., through tubing and a suitable fluidic connection), and two or more outlets (e.g., 2420 and 2422) for allowing at least a portion of the sample to exit the chamber 2400. Along the flow path between the inlet 2410 and the outlets 2420, 2422, the chamber may include an imaging and merging region 2402, and a sorting region 2404 that is downstream from the imaging and merging region 2402. The chamber 2400 may include multiple spacer posts 2432 and 2434, distributed throughout regions 2402 and 2404 respectively, that support and/or maintain the gap distance between upper and lower surfaces of the chamber. For example, as shown in the cross-sectional stack-up schematic FIG. 24B, the spacer posts 2432, 2434 may extend between and support the spacing (e.g., 75 μm or other suitable gap distance) between transparent polyimide surface (having a thickness of about 25 μm, or other suitable thickness). The chamber may, in some variations, be formed with a lamination press that joins the polyimide surfaces at least in part with a suitable adhesive.

As described in further detail below, at least the spacer posts 2402 in the imaging and merging region 2402 may function as electrodes that deliver electrical energy to merge selected PODS. The spacer posts 2432, 2434 may, for example, include a conductive material such as copper. At least the spacer posts 2404 in the sorting region may function to sort PODS according to size.

Generally, the imaging and merging region 2402 may be positioned between one or more light sources and/or imager array such that the imager array may obtain shadow images of PODS or other particles that have entered the chamber. The one or more images may be analyzed using computation techniques such as those described herein with respect to FIGS. 21A-21E. Based on the analysis of such images, PODS that are not of interest (e.g., do not include cells, or include cells lacking IgG or other agglutination) may be characterized as PODS for discard. Such discard PODS may then be designated for electromerging by one or more processors in the system.

Electromerging may be accomplished with spacer posts 2402 functioning as electrodes. As shown in FIG. 24C, an electrode may be conductively coupled (e.g., through a conductive connection such as a trace or wiring) to a controller 2450 configured to control the activation of the electrodes. Although FIG. 24C illustrates four conductive connections for respectively four electrodes, it should be understood that in some variations, more than four spacer posts 2402 may function as electrodes, and each electrode may have its own respective conductive connection (or alternatively, at least some number n electrodes may be controlled by fewer than n conductive connections through a suitable multiplexing scheme).

In this example, the controller 2450 may include a signal generator 2456 configured to generate one or more suitable waveforms with which to drive the electrodes. In some variations, the signal generator 2456 may be configured to drive the electrodes with an AC waveform (e.g., square, triangle, sinusoidal, etc.), such that PODS between pairs of electrodes (e.g., adjacent pairs) are capacitively coupled to the electrodes and receive electrical energy with alternating polarity, Upon receiving such electrical energy, the PODS experience periodic compressive forces that breaks the PODS and causes adjacent affected PODS to merge into larger pod(s). Specific parameters of the AC waveform may vary depending on the application (e.g., size of PODS, size and material of electrodes, spacing between electrodes, etc.), but generally the drive waveform should have sufficient voltage to elicit the merging effect, without being so excessive so as to result in damage to the sample (e.g., result in bubbles, black spots, etc.). For example, in some variations the waveform may have a peak-to-peak voltage between about 0.5 V and about 10 V, between about 0.5 V and about 5 V, or about 2.5 V. Furthermore, in some variations the waveform may have a frequency between about 1 Hz and 1 MHz, between about 10 Hz and about 20 kHz, or between about 50 Hz and about 20 kHz. For a single instance of merging PODS, the pulses of the drive waveform may cycle any suitable number times, such as between about 1 and 20 times, and pulse width may, in some variations, vary between about 10 ms and 10 s in duration. However, the drive waveform may have any suitable pulse width, number of cycles, etc.

The signal generator 2456 may be conductively coupled to each electrode with traces, wiring, or other suitable connection. Along these conductive connections, signal processing circuitry 2454 (e.g., amplifiers) may, for each individual conductive connection or collectively for all conductive connections, may amplify or otherwise modify the driving signal as appropriate. Furthermore, a switch array 2452 including a switch for each conductive connection may be controlled to selectively turn ON and OFF the activation of each switch's corresponding electrode. Accordingly, the controller 2450 may cause at least some of the spacer posts 2402 (functioning as electrodes) to deliver suitable electrical energy for electromerging PODS that are identified for merging (e.g., PODS not of interest) and are in contact with or capacitively coupled with the spacer posts 2402.

As described above, following the passage of the sample through the imaging and merging region 2402 of the chamber, the larger PODS are generally PODS not of interest (e.g., do not include high secretor cells) while the smaller PODS are of interest and are desirable to keep. Therefore, the sorting region 2404 of the chamber functions to separate the smaller PODS from the larger PODS for collection. As shown in the variation depicted in FIGS. 24-24C, the sorting region 2404 may include spacer posts 2434 arranged in a staggered array, which may be configured to passively sort larger PODS laterally (relative to the left-to-right flow direction) toward outlet 2422. Smaller PODS may simultaneously be passively sorted toward outlet 2420. It should be understood, however, that in other variations the electromerging chamber may additionally or alternatively include any suitable passive and/or active particle sorting arrangement.

Accordingly, by directing the sample across the imaging and merging region 2402 and the sorting region 2404, the electromerging chamber arrangement 2400 may provide a concentrated output of PODS of interest (collectable at outlet 2422), and a separate, waste output of PODS not of interest (collectable of outlet 2420) that avoids dilution of the PODS of interest. Furthermore, a continuous flow of sample through the chamber 2400 may enable a high throughput of PODS, thereby further contributing to a highly efficient processing of samples, suggesting viability of the electromerging systems and methods described herein.

Fluidic Control System

As shown in the schematic of FIG. 1A and the illustration showing an exemplary variation in FIG. 1B, the system 100 may include a fluidic control system configured to manipulate PODS with a pressure differential. The fluidic pressure differential may induce one or more PODS to enter the chamber through the chamber inlet 122, include one or more PODS to traverse across the chamber, and/or induce one or more PODS to exit the chamber through the chamber outlet 124. For example, the system 100 may include at least one positive pressure pump 110 fluidically coupled to (or otherwise associated with) the chamber inlet 122 and/or at least one negative pressure pump 150 fluidically coupled to (or otherwise associated with) the chamber outlet 124. The pumps 110 and/or 150 may be configured to draw an emulsion (including PODS, for example) from a reservoir 116 (e.g., tank, Eppendorf tube, other suitable container, etc.) into the chamber 120 via tubing and the at least one chamber inlet 122. The pumps 110 and/or 150 may additionally or alternatively be configured to draw at least a portion of the emulsion from the chamber 120 through the at least one chamber outlet 124. In some variations, a waste container 156 may be coupled in-line between the chamber outlet 124 and the pump 150 for receiving and holding emulsion that has exited the chamber 120. Although the schematic of FIG. 1 illustrates one pump 110 associated with one chamber inlet 112, and one pump 150 associated with the chamber outlet 124, it should be understood that in other variations, the system may include any suitable number of chamber inlets, chamber outlets, and pumps. Furthermore, in some variations, the chamber 120 may be detachable for integration with other fluidic control systems. The chamber 120 may be a disposable component, while the rest of the fluidic control system may be reusable and/or sterilizable.

Additionally, the assay system 100 may include one or more valves that may enable further fluidic control within the assay system 100. For example, valve 112 may be located in-line with fluidic flow to one or more chamber inlets, and may be controlled to regulate sample flow into the chamber 120. Additionally or alternatively, valve 152 may be located in-line with fluidic flow from one or more chamber outlets, and may be controlled to regulate sample flow out of the chamber 120. Furthermore, the assay system 100 may include one or more pressure sensors 114, 154 (or flow sensors, or any suitable sensors) configured to monitor pressure and/or other parameters of the fluidic system.

In some variations, components of the fluidic control system, including the above-described pumps, valves, and/or sensors, can be controlled by one or more controllers. For example, the electronics system 160 may include one or more controllers configured to implement any suitable control system to operate one or more pumps and/or valves based at least in part on sensor input from the pressure sensors, to maintain a desired rate of flow into the chamber 120. Furthermore, the control system can operate these components so as to facilitate sorting of the samples in the chamber, as further described in U.S. patent application Ser. No. 15/986,416 which was incorporated by reference above.

Electronics System

As shown in FIG. 1, the system 100 may include an electronics system 160. The electronics system 160 may include, for example, a PCBA with one or more processors, etc. configured to control and/or receive signals from other components of the assay system 100, as further described herein. In some variations, the electronics system 160 may further include one or more communication components (e.g., Bluetooth, WiFi, etc.) configured to communicate data (e.g., image data) to a network 170 for analysis by one or more remote processors 180. For example, the network 170 may include any suitable wired or wireless connection with one or more computing devices. Additionally or alternatively, at least some of the data may be analyzed by one or more processors located in the electronics system 160.

Generally, the computing devices may include a controller including a processor (e.g., CPU) and memory (which can include one or more computer-readable storage mediums). The processor may incorporate data received from memory and user input. The memory may include store instructions to cause the processor to execute modules, processes, and/or functions associated with the methods described herein. In some variations, the memory and processor may be implemented on a single chip, while in other variations they can be implanted on separate chips.

The processor may be any suitable processing device configured to run and/or execute a set of instructions or code, and may include one or more data processors, image processors, graphics processing units, physics processing units, digital signal processors, and/or central processing units. The processor may be, for example, a general purpose processor, a Field Programmable Gate Array (FPGA), an Application Specific Integrated Circuit (ASIC), and/or the like. The processor may be configured to run and/or execute application processes and/or other modules, processes and/or functions associated with the system and/or a network associated therewith. The underlying device technologies may be provided in a variety of component types (e.g., MOSFET technologies like complementary metal-oxide semiconductor (CMOS), bipolar technologies like emitter-coupled logic (ECL), polymer technologies (e.g., silicon-conjugated polymer and metal-conjugated polymer-metal structures), mixed analog and digital, and/or the like.

One or more processors may, for example, provide a computer vision system configured to analyze images (e.g., shadow images acquired as described herein) to assess an imaged sample using suitable image processing and/or computer vision techniques. For example, with reference to FIGS. 21A-21E, in some variations, one or more processors may process an original (raw) shadow image (FIG. 21A) to reduce noise (e.g., through a filter process) and remove background content (FIG. 21B) (e.g., obtained through a control image of the chamber when empty or without a sample under the same or similar lighting conditions, or with a software algorithm). The sample image may be subtracted from the background image to obtain a subtracted image (FIG. 21C). After subtraction, any dark objects in the original image may appear brighter in the subtracted image. The subtracted image may be thresholded on pixel intensities to obtain a binary, black and white image of one or more PODS (FIG. 21D). For example, any objects in the POD may appear white in the binary image, while other regions may appear black (or vice-versa). Finally, suitable computer vision techniques (e.g., contour searching algorithm) may be applied to find the boundaries of object (e.g., POD, POD content such as cells or particles), thereby enabling identification of the object. In some variations, such contour searching algorithms may incorporate one or more trained machine learning models. One or more characteristics of POD and/or POD content based on suitable computer vision techniques may be identified in the processed image (e.g., as highlighted in FIG. 21E). For example, many properties such as area, particle size, particle shape, greyscale (e.g., intensity), rate of movement, current flow within the POD, ratios and/or dynamic changes thereof, and/or any combination thereof may be analyzed.

In some variations, the memory may include a database and may be, for example, a random access memory (RAM), a memory buffer, a hard drive, an erasable programmable read-only memory (EPROM), an electrically erasable read-only memory (EEPROM), a read-only memory (ROM), Flash memory, and the like. The memory may store instructions to cause the processor to execute modules, processes, and/or functions such as measurement data processing, measurement device control, communication, and/or device settings. Some variations described herein relate to a computer storage product with a non-transitory computer-readable medium (also may be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also may be referred to as code or algorithm) may be those designed and constructed for the specific purpose or purposes.

Examples of non-transitory computer-readable media include, but are not limited to, magnetic storage media such as hard disks, floppy disks, and magnetic tape; optical storage media such as Compact Disc/Digital Video Discs (CD/DVDs); Compact Disc-Read Only Memories (CDROMs), and holographic devices; magneto-optical storage media such as optical disks; solid state storage devices such as a solid state drive (SSD) and a solid state hybrid drive (SSHD); carrier wave signal processing modules; and hardware devices that are specially configured to store and execute program code, such as Application-Specific Integrated Circuits (ASICs), Programmable Logic Devices (PLDs), Read-Only Memory (ROM), and Random-Access Memory (RAM) devices. Other variations described herein relate to a computer program product, which may include, for example, the instructions and/or computer code disclosed herein.

The systems, devices, and/or methods described herein may be performed by software (executed on hardware), hardware, or a combination thereof. Hardware modules may include, for example, a general-purpose processor (or microprocessor or microcontroller), a field programmable gate array (FPGA), and/or an application specific integrated circuit (ASIC). Software modules (executed on hardware) may be expressed in a variety of software languages (e.g., computer code), including C, C++, Java®, Python, Ruby, Visual Basic®, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. Additional examples of computer code include, but are not limited to, control signals, encrypted code, and compressed code.

In some variations, a computing device may further include a communication interface configured to permit a patient and/or other used to control the computing device. The communication interface may include a network interface configured to connect the computing device to another system (e.g., Internet, remote server, database) by wired or wireless connection. In some variations, the computing device may be in communication with other devices via one or more wired or wireless networks. In some variations, the communication interface may include a radiofrequency receiver, transmitter, and/or optical (e.g., infrared) receiver and transmitter configured to communicate with one or more device and/or networks.

Wireless communication may use any of a plurality of communication standards, protocols, and technologies, including but not limited to, Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Wireless Fidelity (WiFi) (e.g., IEEE 802.11a, IEEE 802.11b, IEEE 802.11g, IEEE 802.11n, and the like), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol. In some variations, the devices herein may directly communicate with each other without transmitting data through a network (e.g., through NFC, Bluetooth, WiFi, RFID, and the like).

Clustering Assays

As discussed above, systems and methods such as those described herein may, for example, be used for processing cell samples. A clustering assay may be used for identification of cells that are high secretors or producers of antibodies for specific targets, for example. In a population of cells, certain cells within the population may, relative to the other cells of the population, be high secretors of a target of interest, such as a protein of interest. Exemplary variations of systems and methods for clustering assays are described in further detail below.

"One-Bead" Assay

A clustering assay using a one-bead system ("one-bead assay," or "one-bead clustering assay") may be used to identify the high secretor cells within the population of cells. Although the "one-bead assay" is primarily described below as including one or more beads as marker particles, it should be understood that other particles may be used (e.g., cells, as described in further detail below). The one-bead clustering assay may be used to identify a secreting cell encapsulated within a POD as a high secretor of a target protein (or peptide, etc.). For example, the assay may utilize one or more particles of a first type that provides a signal indicating a cell's secretion level of the antibody of interest.

Figure 32A:
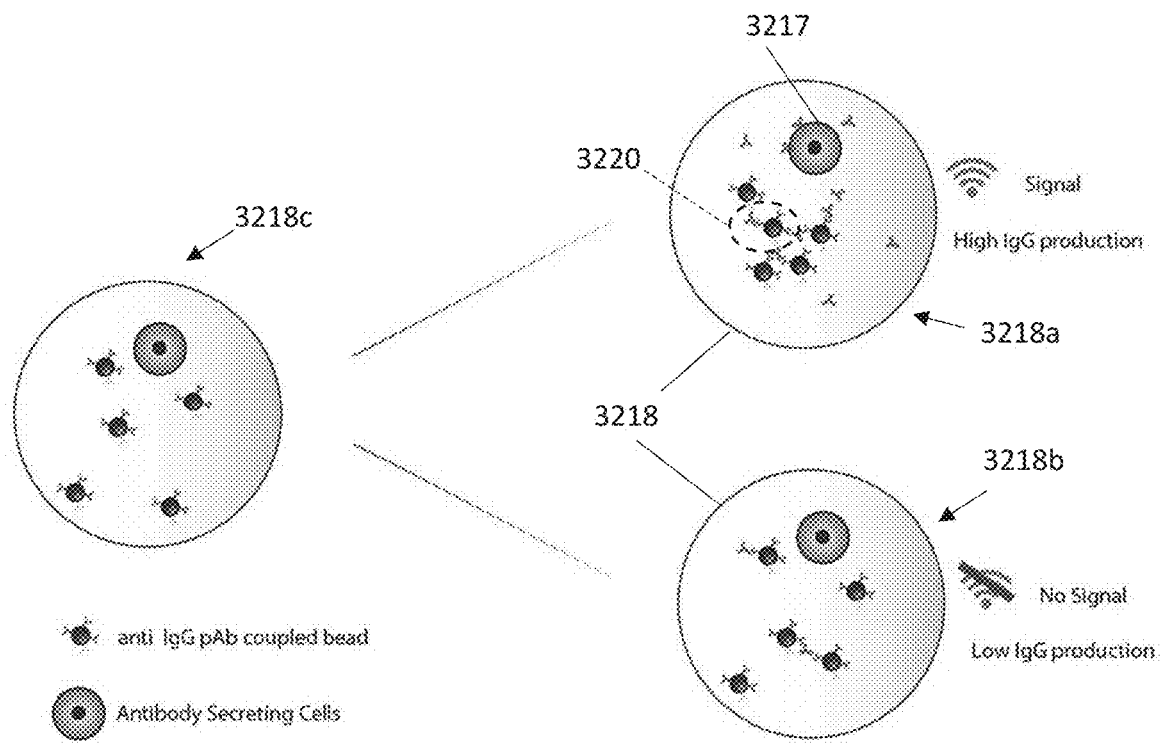
FIG. 32A depicts a schematic diagram of the binding interactions that may occur inside of a POD when using a one-bead assay.
Figure 32B:
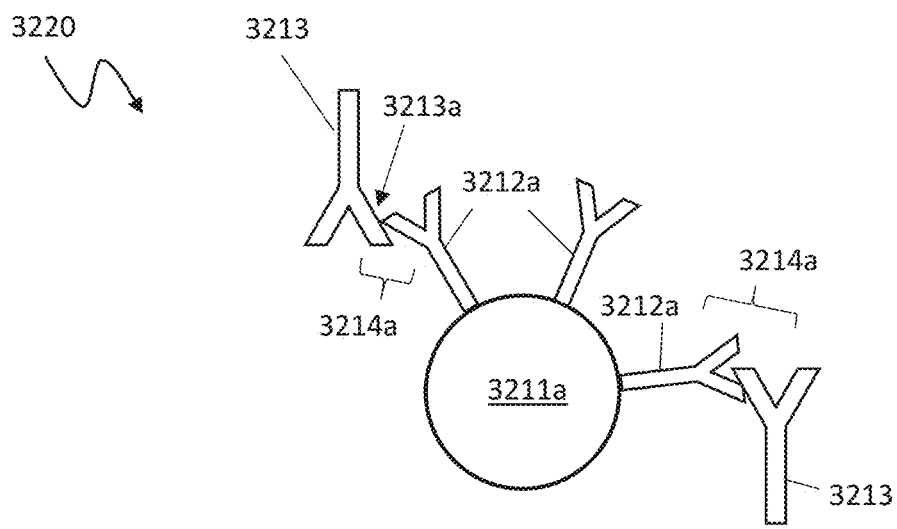
FIG. 32B shows a detailed enlargement of a region of FIG. 32A, showing a single particle.

FIG. 32A depicts a schematic diagram of the binding interactions that may occur inside of a sample entity such as a POD 3218 when using a one-bead assay. The POD 328 may include one or more particles with a binding partner that may be specific to a second binding partner that is secreted by a cell 3217. FIG. 32B depicts a detailed enlargement of region 3220 of FIG. 32A, showing a single particle 3211a. As shown as an example, the one-bead clustering assay may be used to identify an antibody secreting cell 3217 encapsulated within a POD 3218 as a high secretor of the antibody of interest 3213. The one-bead clustering assay may utilize an encapsulation reagent, and a first plurality of particles suspended in aqueous media. The encapsulation reagent may comprise a density greater than about 1.0 which may, for example, help form discrete sample entities such as PODs including aqueous media. Each particle of the first plurality of particles may comprise a first binding partner that is specific to a second binding partner secreted by the cell of interest.

Again, as was previously described when referring to FIG. 23B, a sample for use in a one-bead assay may include cells mixed with a surfactant such as a fluoro-oil and beads or other markers to create an emulsion with sample entities, where each sample entity may function as a self-contained vesicle. The encapsulation reagent may include the surfactant, which may at least in part enable the encapsulation of portions of the sample into the sample entities. Examples of formulations wherein the encapsulation reagent comprises a surfactant are shown in Tables 1-3. The PODS may be polydisperse within a sample used for analysis. The particles of the first plurality of particles may be beads, such as an antibody coupled bead 3211a as shown as an example in FIG. 32B, having a polyclonal antibody 3212a coupled to its surface. The particles of the first plurality of particles may be cells, such that antigens or any other suitable markers expressed on the cell may bind with the antibody secreted by a cell of interest. The markers or antigens on a cell or the polyclonal antibody 3212a on a bead may thus act as the first binding partner that is specific to a second binding partner, which may be a binding domain or any suitable component 3213a of the antibody 3213 secreted by the cell 3217. In some variations, the first binding partner may comprise a first protein, and the second binding partner may comprise a second protein. In some variations, the first binding partner or the second binding partner may be an antigen or antibody. In some variations, the first binding partner may comprise a first peptide, and the second binding partner may comprise a second peptide.

When the first binding partner 3212a and the second binding partner 3213a are bound, the site of the binding may be referred to as a cluster site, or a first cluster site 3214a as shown in FIG. 32B. These cluster sites formed by a binding of the first and second binding partners may be detected by the systems and methods such as those described herein. Furthermore, in some variations, certain cells may be selected as being a cell of interest by being a high secretor of the antibody 3213, and high secretor cells may generate larger clusters. The clusters formed by the first binding partner 3212a and the second binding partner 3213a may be observable using a lensless imager system as described above, for example, and thus may enable the selection of a high secretor cell. High secretor cells may also be measured or detected using any of the imaging methods described herein.

Thus, the clustering assay may enable identification of PODs including cells of interest (e.g., cells that secrete a sufficiently high amount of a substance of interest). For example, a larger amount of the antibody of interest being secreted from a cell may lead to a larger cluster due to a larger amount of cluster sites being formed, such as the first cluster sites shown by 3213a of FIG. 32B. A larger amount of interactions between the polyclonal antibody 3212a coupled to the bead 3211a and the binding region 3213a of the antibody 3213 secreted by the cell may thus result in a larger number of clusters being formed, which may then be detectable as one or more large clusters. The formed clusters may then be visually detected, or measurable by any of the imaging methods described herein, and may be interpreted as a signal that the POD from which the cluster is detected is a POD containing a cell of interest.

Generally, a larger cluster will result in a POD having a higher-secreting cell of the antibody of interest. The larger size of these clusters may allow for the clusters to be visualized using a 4× microscope objective, for example. As another example, the clusters may be observed in shadow images such as those taken by the systems described above with reference to FIGS. 2A, 9, 10, and 14A-14C. An example of a cell secreting or producing a sufficient amount of an antibody of interest to generate a detectable or measurable signal is shown in a first POD 3218a of FIG. 32A.

In some variations, a POD comprising one or more cluster sites may be assigned a particle size score (PSS). For example, PSS may be determined for and assigned to a POD as described below in the Examples. PODs with higher PSS, for example, may be identified as including a cell of interest (e.g., high secretor cell) and may be sorted (e.g., as described above through electromerging and sorting processes, etc.) so as to separate cells of interest from the population of cells. At least some of the sorted cells may undergo further processing, such as ELISA, FACS, DNA sequencing, PCR, other suitable analysis, and so on. In some variations, the cell of interest may be removed from the POD 3218 for such further processing.

The clustering assay also enables identification of PODs not including cells of interest (e.g., cells that secrete no or low amounts of a substance of interest). For example, when a cell within a POD is not secreting the antibody of interest, no clusters may be formed due to no interactions occurring between the polyclonal antibody 3212a coupled to the bead 3211a and the antibody of interest. Additionally, when a cell within a POD is secreting a low amount of the antibody of interest, interactions may occur between the secreted antibody and the polyclonal antibody 3212a coupled to the bead 3211a, but the amount or number of binding interactions may be too low to generate a detectable or measurable signal. In some variations, a "low" signal may indicate less than about 1 pg of secreted amount of the antibody of interest over about 3 hours, for a sample including PODS having an average volume of about 0.5 nL. For example, any formed clusters in a POD with a low-secreting cell may be below a threshold size, and/or may be too small to be visualized using a 4× microscope objective, or in shadow images such as those described above with reference to FIGS. 2A, 9, 10, and 14A-14C. An example of a cell secreting or producing an insufficient amount of an antibody of interest to generate a detectable or measurable signal is shown in a second POD 3218b of FIG. 32A.

Examples of binding partners that may act as a first binding partner, as shown by 3212a in FIG. 32B, may include a polyclonal antibody among one or more classes of antibodies such as IgA, IgD, IgE, IgG, and IgM.

Examples of cells of interest that may be selected for using the one-bead assay may include any one or more of CHO cells, B cells, hybridoma cells, plasma cells, HEK293 cells, myeloma cells, and T-cells, etc.

Examples of antibodies of interest that may be selected for using the one-bead assay may include an antibody among one or more classes of antibodies such as IgA, IgD, IgE, IgE, and IgM, etc.

Examples of proteins and peptides of interest includes any suitable standard biomarkers such as insulin, NT-pro-BNP, Pro-GRP, β-CTX, PINP, pancreatic polypeptide, osteocalcin, $β_2$-microglobulin, calcitonin, cystatin C, C-peptide, VIP, ANF, NTX, β-amyloid (1-42), PSA, K-RAS, CA125, CA 15-3, MUC-1, HER-2/neu, estrogen receptor, progesterone receptor, etc.

"Two-Bead" Assay

In some variations, it may also be valuable to identify and collect cells that are not only high secretors of a target of interest (again, such as a protein of interest) but also wherein the target of interest shows a high affinity and/or specificity of binding to a partner antigen. A clustering assay using a two-bead system ("two-bead assay," or "two-bead clustering assay") may be used to assess the level of antibody secretion from a target cell as well as the antigen binding affinity of the secreted antibody. Thus, the two-bead assay may be used to select a cell of interest secreting a high amount of an antibody of interest, wherein the secreted antibody also displays a high antigen binding affinity. For example, the assay may utilize one or more particles of a first type that provides a signal indicating a cell's secretion level of the antibody of interest, and one or more particles of a second type that provides a signal indicating level of antigen binding affinity for any such secreted antibody. Although the "two-bead assay" is primarily described below as including one or more beads as marker particles, it should be understood that other particles may be used (e.g., cells, as described in further detail below).

Similar to the one-bead assay described above, the two-bead assay may be used for analysis of a sample, which may include cells mixed with a surfactant such as a fluoro-oil and beads or other markers to create an emulsion with sample entities, where each sample entity may function as a self-contained vesicle. The two-bead assay may also utilize an encapsulation reagent, and a first plurality of particles suspended in aqueous media, and a second plurality of particles also suspended in aqueous media. The encapsulation reagent may comprise a density greater than about 1.0. The encapsulation reagent may include a surfactant, which may at least in part enable the encapsulation of portions of the sample into the sample entities. The sample entities may be PODS.

Like with the one-bead assay described above, each particle of the first plurality of particles may comprise a first binding partner that is specific to a second binding partner secreted by the cell of interest. However, the two-bead assay may also utilize a second plurality of particles, wherein each particle of the second plurality of particles comprises a third binding partner that is specific to a fourth binding partner secreted by the cell of interest.

Figure 33A:
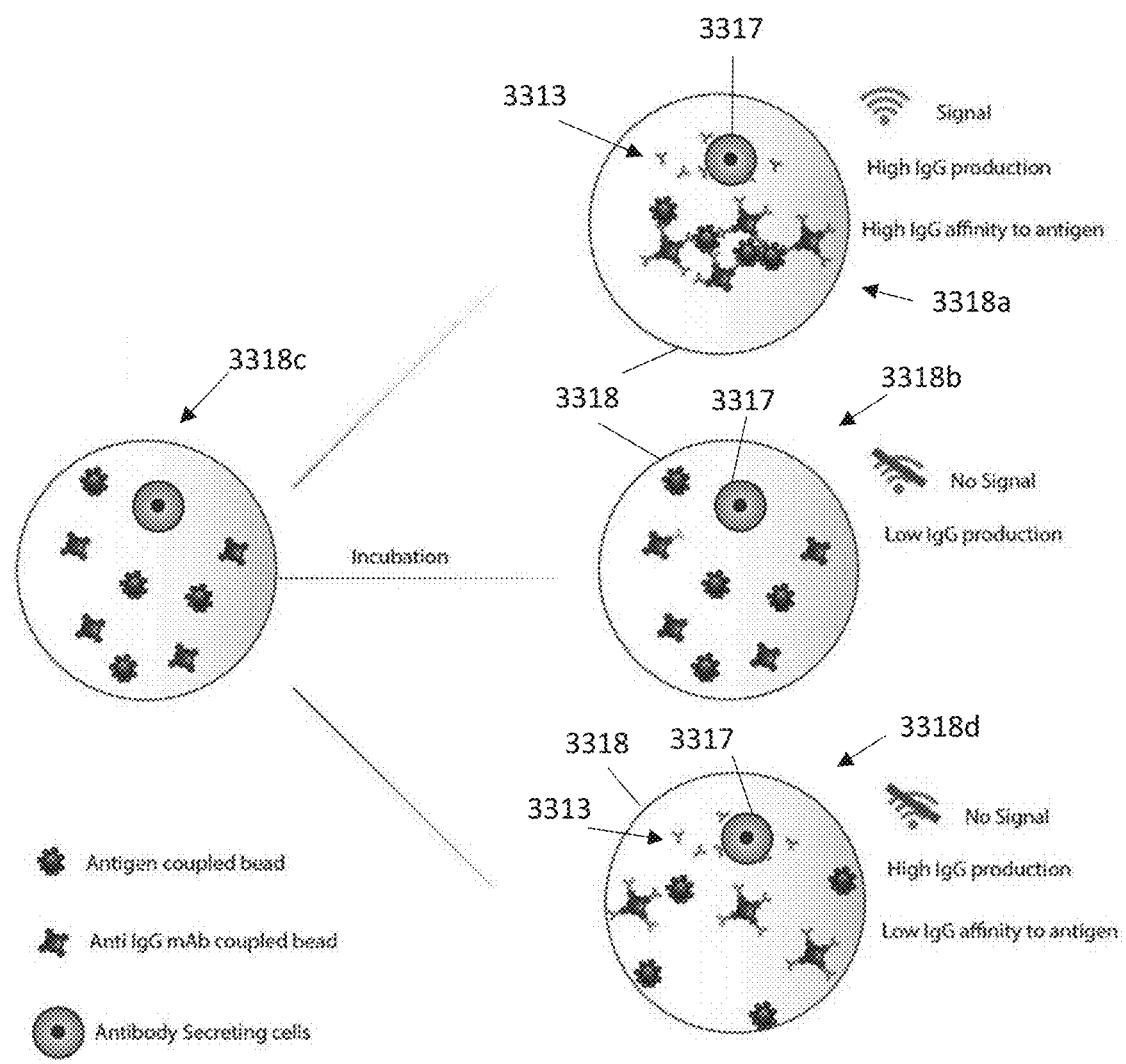
FIG. 33A depicts a schematic diagram of the binding interactions that may occur inside of a POD when using a two-bead assay.

FIG. 33A depicts a schematic diagram of the binding interactions that may occur inside of a POD 3318 when using a two-bead assay. Shown as examples are PODS 3318a, 3318b, and 3318d, as will be described in further detail herein. POD 3318a is an example of a detectable or measurable signal being generated, due to a cell 3317 identified as a cell of interest, being a high secretor of an antibody of interest 3313, wherein the antibody 3313 has a high antigen binding affinity. POD 3318b is an example of no detectable or measurable signal being generated, due to a cell 3317 being a low producer of the antibody of interest. POD 3318d is an example of no detectable or measurable signal being generated, due to a cell 3317 being a high secretor of the antibody of interest, but wherein the antibody 3313 has a low antigen binding affinity.

Figure 33B:
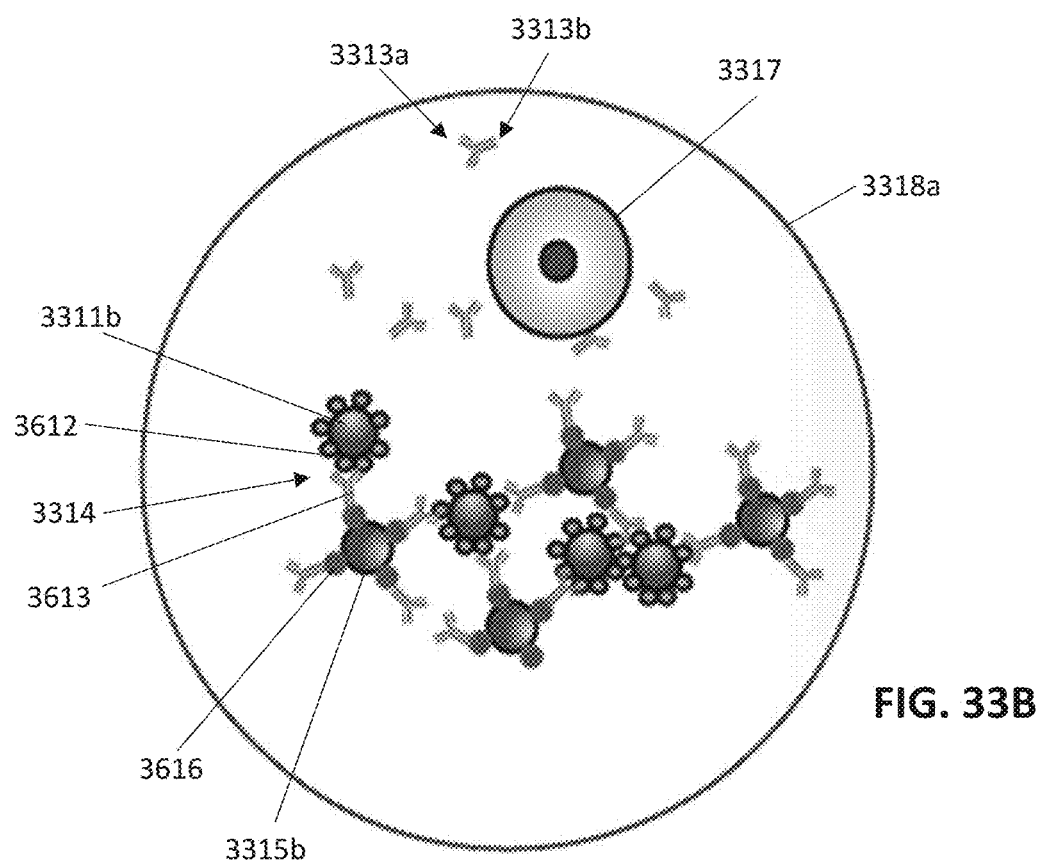
FIG. 33B shows a detailed enlargement of a POD of FIG. 33A.
Figure 33C:
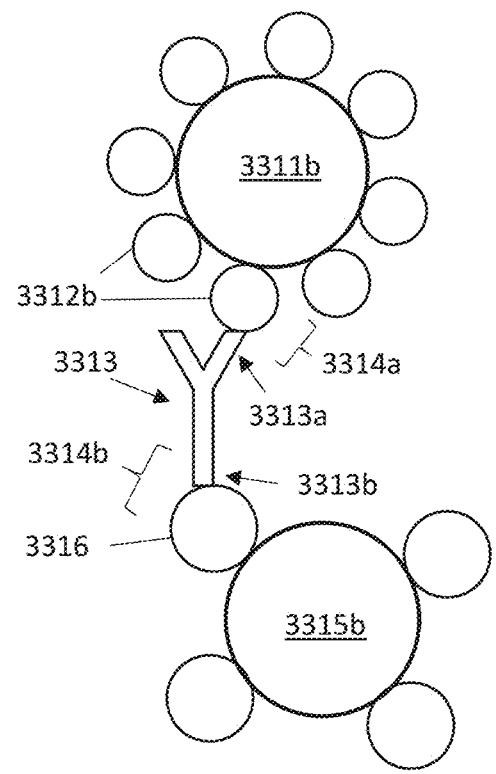
FIG. 33C shows a detailed enlargement of a binding interaction within the POD of FIGS. 33A-33B.

FIG. 33B depicts a detailed enlargement of POD 3318a of FIG. 33A, and FIG. 33C shows a detailed enlargement of a binding interaction within the POD 3318a of FIGS. 33A-33B.

In the two-bead assay, the particles of the first plurality of particles may be beads, such as an antigen coupled bead 3311b having an antigen 3312b coupled to its surface. The antigen 3312b may thus act as the first binding partner that is specific to a second binding partner, which may be a binding domain or any suitable first component 3313a of the antibody 3313 secreted by the cell 3317. The first component 3313a may be an antigen binding domain. The particles of the second plurality of particles may also be beads, such as an antibody coupled bead 3315b having an antibody coupled to its surface. The antibody 3316 may be a monoclonal antibody, and may act as the third binding partner that is specific to a fourth binding partner, which may be a binding domain or any suitable component 3313b of the antibody 3313 secreted by the cell 3317. As shown in detail in FIG. 33C, when the antibody 3313 displays a high antigen binding affinity for the antigen 3312b, coupled to the beads making up the first plurality of particles 3311b, a binding interaction may occur. When the antigen (acting as the first binding partner) 3312b and a binding domain of the antibody (acting as the second binding partner) 3313a are bound, the site of the binding may be referred to as a cluster site, or a first cluster site 3314a. A high amount of the antibody of interest 3313 being secreted by the cell 3317 may cause a larger size of cluster formed by the interactions between the antibody 3313 and the antigen 3312b.

Additionally, a second binding domain 3313b of the antibody 3313 may bind to a monoclonal antibody 3316 coupled to the beads making up the second plurality of particles 3315b. A second cluster site 3314b may be formed by the binding of the binding domain of the antibody (acting as the third binding partner) 3316 and the monoclonal antibody (acting as the fourth binding partner) 3313b.

Accordingly, the two-bead clustering assay may enable identification of PODs including cells of interest (e.g., cells that are high secretors of a substance of interest that also has a high specific level of binding affinity for another substance of interest). A POD having a cell that secretes a high level of the antibody of interest and wherein the secreted antibody of interest has a high antigen binding affinity may result in a large cluster. A large cluster may be formed when both the first cluster site and the second cluster site are present throughout a POD, such as the POD 3318a shown as an example in FIG. 33A.

The two-bead clustering assay also may enable identification of PODs not including cells of interest (e.g., cells that secrete no or low amounts of a substance of interest and/or cells that secrete a substance of interest but the secreted substance of interest has a low binding affinity for another substance of interest). A POD having a cell that does not secrete the antibody of interest, or a cell that secretes a low amount of the antibody of interest, may result in a cluster below a threshold size and/or no measurable or detectable clustering, such as POD 3318b shown in FIG. 33A. Furthermore, a POD containing a cell that is a high secretor of an antibody of interest, but wherein the antibody of interest has a low antigen binding affinity, also may result in a cluster below a threshold size and/or no measurable or detectable clustering, such as POD 3318d shown in FIG. 33A. When using the two-bead assay to analyze a sample, the clusters formed by the binding of the antibody to the monoclonal antibody coupled beads alone may result in clusters that are below a threshold size (e.g., measured by a particle size score such as that described herein) or too small to be detectable. The two-bead assay allows for an amplified signal caused by grouping of several binding interactions together, such as in the example POD 3318a, wherein the antibody of interest is able to group several beads together by its high affinity to the antigen 3312b. Thus, the two-bead assay may be a useful tool for detection of a cell that is a high-secretor of an antibody of interest that has a high antigen binding affinity and/or specificity.

In some variations, the first binding partner may comprise a first protein, and the second binding partner may comprise a second protein. In some variations, the first binding partner or the second binding partner may be an antigen or antibody. In some variations, the first binding partner may comprise a first peptide, and the second binding partner may comprise a second peptide. Furthermore, as described in further detail below, in some variations the particles of the first plurality of particles and/or second plurality of particles may be cells, such as cells comprising one or more antigens or antibodies.

Certain cells may be selected as being a cell of interest by being a high secretor of the antibody 3313, wherein the antibody 3313 has a high antigen binding affinity and/or specificity, and thus may be selected by the generation of a signal that is detectable using the imaging methods described herein. The detection or measuring of the signal may be performed by specific detection of the monoclonal antibody 3316. The cluster sites may also be detected or measured by the computer vision systems and methods described herein.

In some variations, a POD comprising one or more cluster sites may be assigned a particle size score (PSS). For example, PSS may be determined for and assigned to a POD as described below in the Examples. PODs with higher PSS, for example, may be identified as including a cell of interest (e.g., high secretor cell) and may be sorted (e.g., as described above through electromerging and sorting processes, etc.) so as to separate cells of interest from the population of cells. At least some of the sorted cells, and/or their contents therein may undergo further processing, such as ELISA, FACS, DNA sequencing, PCR, other suitable analysis, and so on. In some variations, the cell of interest may be removed from the POD 3318 for such further processing.

Examples of binding partners that may act as a first binding partner, as shown by 3312b in FIG. 33C, may include an antigen.

Examples of cells of interest that may be selected for using the two-bead assay may include Chinese hamster ovary (CHO) cells, B cells, hybridoma cells, plasma cells, HEK293 cells, myeloma cells, and T cells, etc.

Examples of antibodies of interest that may be selected for using the two-bead assay may include an antibody among one or more classes of antibodies such as IgA, IgD, IgE, IgE, and IgM, etc.

Examples of proteins and peptides of interest that may be selected for using the two-bead assay may include insulin, NT-pro-BNP, Pro-GRP, β-CTX, PINP, pancreatic polypeptide, osteocalcin, $β_2$-microglobulin, calcitonin, cystatin C, C-peptide, VIP, ANF, NTX, β-amyloid (1-42), PSA, K-RAS, CA125, CA 15-3, MUC-1, HER-2/neu, estrogen receptor, progesterone receptor, etc.

Preparation of Samples for Clustering Assay

Figure 34A:
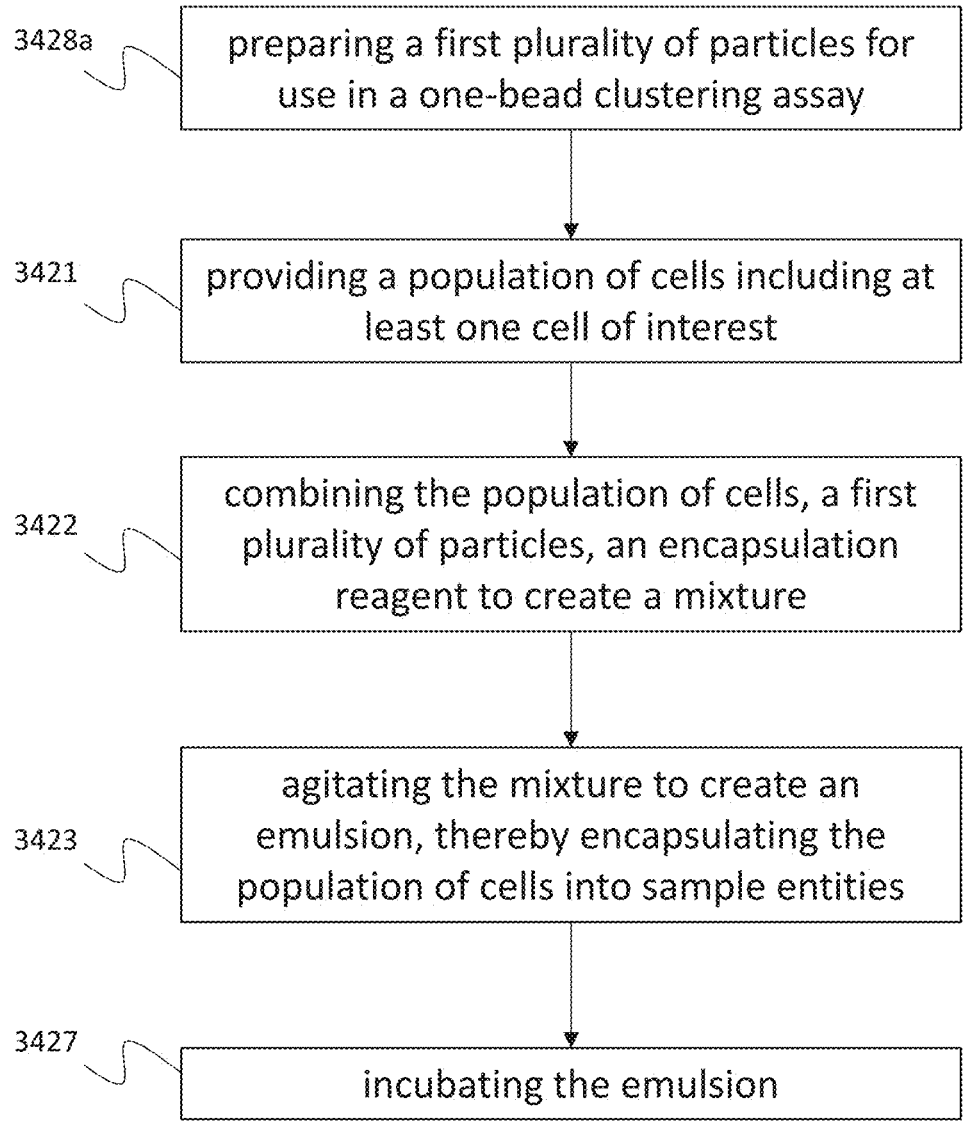
FIG. 34A depicts a flow chart showing an exemplary method of preparing a sample for a one-bead clustering assay system.
Figure 34B:
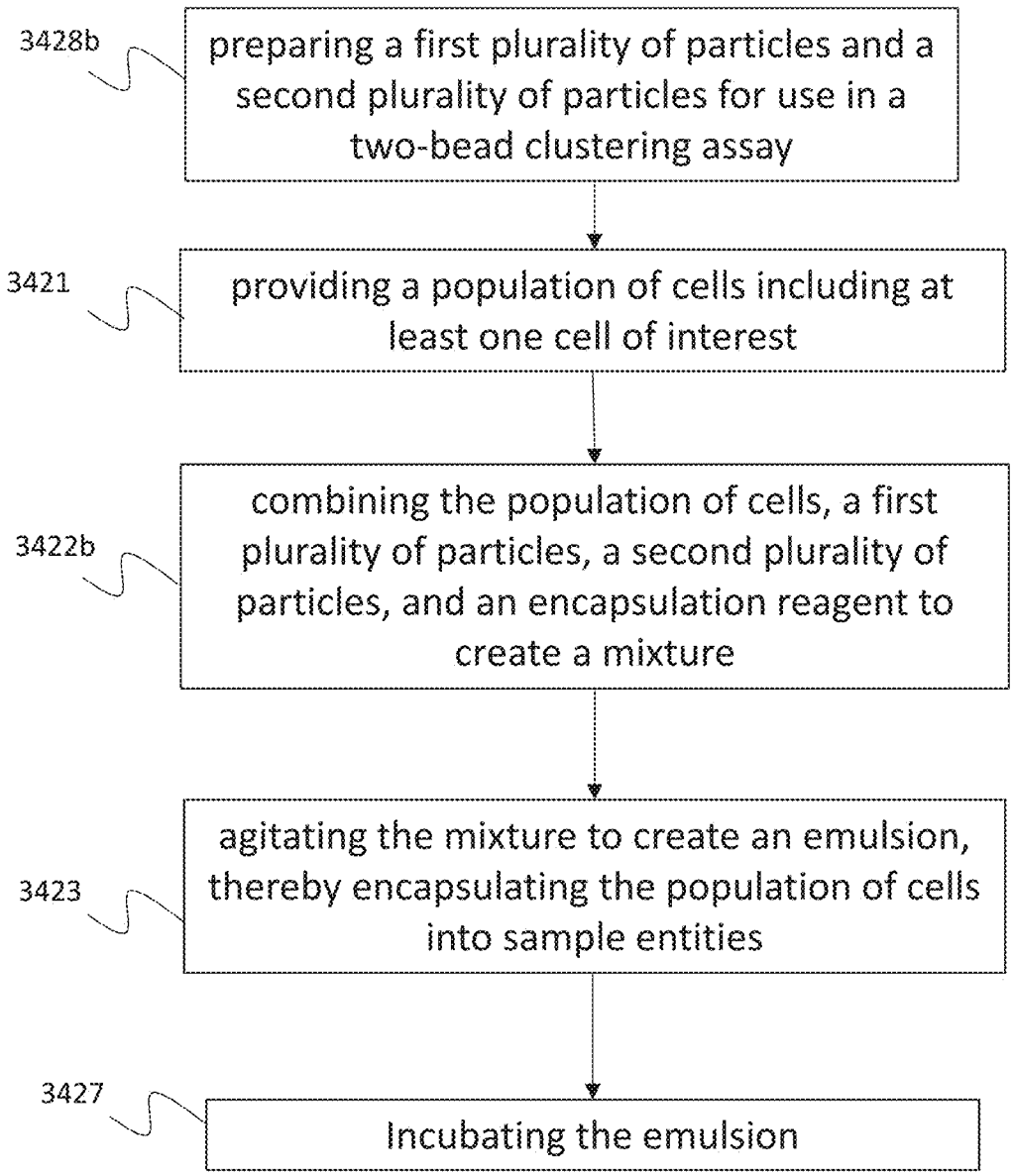
FIG. 34B depicts a flow chart showing an exemplary method of preparing a sample for a two-bead clustering assay system.

FIGS. 34A and 34B depict exemplary variations of methods of preparing a sample for a clustering assay. For example, FIG. 34A depicts a flow chart showing an exemplary method of preparing a sample for a one-bead clustering assay system. The method may include preparing a first plurality of particles for use in the one-bead assay (3428a), which may include coupling the beads with polyclonal antibodies, and normalizing the beads to a desired working concentration. The method may also include providing a population of cells, which may include at least one cell of interest (3421). The population of cells may be prepared by washing in media and diluting to a desired cell concentration to create a cell dilution. Next, the method may include combining the population of cells, the first plurality of particles, and an encapsulation reagent to create a mixture (3422), such as with a vortexer, stirrer (e.g., magnetic stirrer), repeated pipetting, agitation, etc. Each particle of the first plurality of particles may comprise a first binding partner that is specific to a second binding partner secreted by the at least one cell of interest, as further described above. The method may include agitating the mixture to create an emulsion, thereby encapsulating the population of cells into sample entities (3423). The sample entities may be polydisperse (e.g., PODS, such as the POD 3218c shown as an example in FIG. 32B). The method may include incubating the emulsion (3427). Incubating the emulsion may, for example, allow sufficient time for cells of interest to secrete the substance of interest, if any, that may interact with the marker particles (e.g., first plurality of particles). Once incubated, the cells, encapsulated into the sample entities, may be further analyzed such as by introducing the sample entities into the processing chamber as described in detail above, for visualization, assessment, merging, and/or sorting, etc.

FIG. 34B depicts a flow chart showing an exemplary method of preparing a sample for a two-bead clustering assay system. The method may include preparing a first plurality of particles and a second plurality of particles for use in the two-bead assay (3428b), which may include coupling the first plurality of beads with an antigen, and coupling the second plurality of beads with an antibody, and normalizing both batches of beads to a desired working concentration. In some variations, the bead concentration is adjusted so that clustering is observed typically >1 ng/mL or up to 100 ug/mL produced in 1 hour in a sample including PODS having an average volume of 0.5 nL. The method may include providing a population of cells, which may include at least one cell of interest (3421). The population of cells may be prepared by washing in media and diluting to a desired cell concentration to create a cell dilution. The method may include combining the population of cells, the first plurality of particles, the second plurality of particles, and an encapsulation reagent to create a mixture (3422b). Similar to that described above, mixing may be performed with a vortexer or stirrer (e.g., magnetic stirrer, repeated pipetting, etc.). Each particle of the first plurality of particles may comprise a first binding partner that is specific to a second binding partner secreted by the at least one cell of interest, and each particle of the second plurality of particles may comprise a third binding partner that is specific to a fourth binding partner secreted by the at least one cell of interest. The method may include agitating the mixture to create an emulsion, thereby encapsulating the population of cells into polydisperse sample entities (3423). Again, the polydisperse sample entities may be PODS. The agitating step (3423) may result in PODS such as the POD 3318c shown as an example in FIG. 33A. The method may include incubating the emulsion (3427), similar to that described above with respect to the one-bead assay. Once incubated, the cells, encapsulated into the sample entities, may be further analyzed such as by introducing the sample entities into the processing chamber as described in detail above, for visualization, assessment, merging, and/or sorting, etc.

In some variations, the encapsulation reagent for use in preparation of the sample for the one-bead and two-bead assays may comprise a surfactant. In some variations, the surfactant may comprise at least one of fluorine and polyethylene glycol (PEG). In some variations, the encapsulation reagent may be between about 60% and 90% of the mixture. In some variations, the mixture may comprise one or more first particles suspended in aqueous media, each first particle comprising a first binding partner. In some variations, the one or more first particles may be between about 5% and 20% of the mixture by volume. In some variations, the population of cells may be between about 5% and 20% of the mixture by volume. In some variations, the sample entities may comprise polydisperse sample entities. In some variations, the polydisperse sample entities may be PODS. In some variations, the first binding partner may comprise a first protein, and the second binding partner may comprise a second protein. In some variations, the first binding partner or the second binding partner may be an antigen or antibody. In some variations, the first binding partner may comprise a first peptide, and the second binding partner may comprise a second peptide. In some variations, the population of cells may be CHO cells, B cells, hybridoma cells, plasma cells, HEK293 cells, myeloma cells, or T cells.

Table 1 shows an exemplary formulation of an emulsion sample that may be used in the method according to FIG. 34, or in any of the systems or methods described herein, using a 1.5 ml Eppendorf to perform an analysis run. Table 2 shows an exemplary formulation of a 250 ml sample of PODS that may be used in the method according to FIGS. 34-35, or in any of the systems of methods described herein. Tables 1 and 2 do not account for any carrier fluid that may be present in the sample. Table 3 shows an exemplary formulation for a complete sample test run, which may be used in any of the systems and methods described here. In some variations, the formulation summarized in Table 3 may be used for performing an assay using a darkening substrate, as described herein.

TABLE 1

Exemplary emulsion sample formulation

| | 1.5 ml Eppendorf run | % by Volume | % by Weight | Volume Range |
|---|---|---|---|---|
| Encapsulation reagents | % Fluorosurfactant | 75 (180 μl) | 82.0 | 60-180 μl |
| Detection reagents | % Bead | 12.5 (30 μl) | 9.0 | 10-30 μl |
| Sample media | % water (cell) | 12.5 (30 μl) | 9.0 | 10-30 μl |

TABLE 2

Exemplary 250 ml PODS sample

| | % in 1 L run | % by Volume | % by Weight | Volume Range |
|---|---|---|---|---|
| Encapsulation reagents | % Fluorosurfactant | 75 (750 ml) | 82.0 | 250 ml-750 ml |
| Detection reagents | % Bead | 12.5 (125 ml) | 9.0 | 41.67-125 ml |
| Sample media | % water (cell) | 12.5 (125 ml) | 9.0 | 41.67-125 ml |

TABLE 3

Exemplary sample formulation

| | 1.5 ml Eppendorf run | % by Volume | % by Weight | Volume Range |
|---|---|---|---|---|
| Encapsulation reagents | % Fluorosurfactant | 12.68 (180 μl) | 12.88 | 180-360 μl |
| Detection reagents | % Bead | 2.11 (30 μl) | 1.34 | 30-60 μl |
| Sample media | % water (cell) | 2.11 (30 μl) | 1.34 | 30-60 μl |
| Carrier | % carrier | 70.42 (1 ml) | 71.56 | 800-1000 μl |
| Carrier | % carrier, post run rinse | 12.68 (180 μl) | 12.88 | 180 μl |

As described hereinbefore, the particles of the first or second plurality of particles used in the one-bead or two-bead assays may be beads. Such beads may be polystyrene, gold, cellulose, latex, agarose, polyethylene glycol (PEG), glass, or magnetic beads. The beads may be suspended in aqueous media before and while being combined with the population of cells in step 3422. The beads that act as the first and second plurality of particles may be polystyrene, gold, cellulose, latex, agarose, polyethylene glycol (PEG), glass, or magnetic beads, and may be 10 nm to about 50 μm in size.

In some variations, a bead may comprise carboxylate, and may have a diameter between about 0.3 μm to about 6 μm, between about 0.05 μm and about 20 μm, or between about 0.1 μm and 0.3 μm. In some variations, a bead may comprise europium carboxylate, and may have a diameter between about 0.10 μm to about 0.30 μm. In some variations, a bead may comprise carboxyl-polystyrene, and may have a diameter between about 0.05 μm to about 8 μm, or between about 1 to about 1.4 μm. In some variations, a bead may comprise carboxylic acid groups, and may have a diameter between about 0.2 μm to about 5 μm, or may have a diameter of about 0.85 μm, or about 0.4 μm.

In some variations, a cell may act as a particle of the first and second plurality of particles. A cell may naturally express antigens, proteins, or other such markers on its cell surface, and these cell surface markers may act as a first binding partner as in the interactions depicted in FIGS. 32B and 33C, or as a third binding partner as in the interactions depicted in FIG. 33C. A cell expressing a marker on its surface may therefore take the place of a bead in the one-bead or two-bead assays described herein.

Figure 43A:
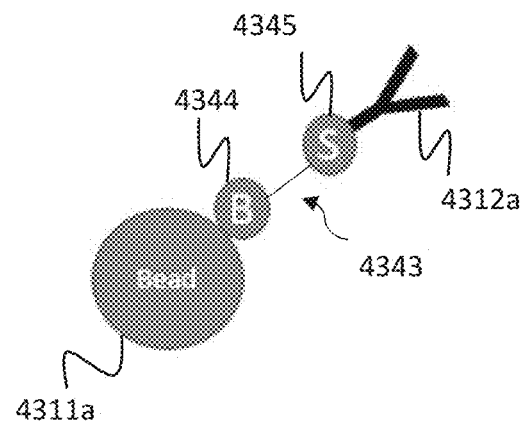
FIG. 43A depicts a schematic illustration of a first binding partner complex for use in a one-bead or two-bead assay, using biotin coated beads and streptavidin conjugated antibodies.
Figure 43B:
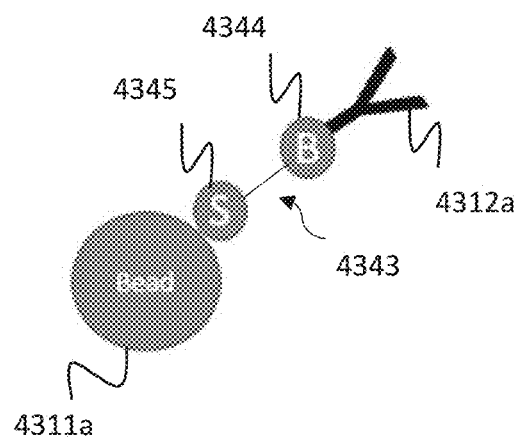
FIG. 43B depicts a schematic illustration of a first binding partner complex for use in a one-bead or two-bead assay, using streptavidin coated beads and biotin conjugated antibodies.

In some variations, proteins having known binding partners or known interactions with other proteins may be utilized in the one-bead or two-bead assays. In these variations, an antibody may act as the first binding partner, such as in the exemplary embodiment shown in FIG. 32B, and may be coupled to a bead 4311a by use of a bond (indicated at 4343) between known binding partners. Similar to the embodiment shown in FIG. 32B, an antibody 4312a, may be bound by a protein of interest secreted by a cell, for example, which may generate a measurable or detectable signal for the assay. Again, this may indicate that the cell secreting the protein of interest may be a high-secreting cell, and thus a cell of interest. In these variations, the antibody acting as the first binding partner 4312a may be conjugated to a protein having a known binding partner. As shown in FIG. 43A as an example, the bead 4311a may be coupled to biotin 4344. Streptavidin 4345, a known binding partner for biotin 4344, may be conjugated to the antibody acting as the first binding partner 4312a. The biotinylated bead may be provided separately from the antibody acting as the first binding partner. For example, a plurality of biotinylated beads may be provided as part of a kit, where the biotinylated beads may be mixed with streptavidin conjugated antibodies acting as a first binding partner. Alternatively, the biotinylated bead and the antibody may be provided together, such that the first binding partner is provided in a complex, including the bead 4311a, the biotin 4344, the streptavidin 4345, and the antibody 4312a, wherein the biotin 4344 and the streptavidin 4345 are bound (indicated at arrow 4343). As shown in FIG. 43B as another example, the streptavidin 4345 may be coupled to the bead 4311a, and the biotin 4344 may be conjugated to the antibody 4312a. Similar to the example shown in FIG. 43A, a plurality of beads 4311a with streptavidin may be provided as part of a kit, wherein the beads 4311a may be mixed with biotin conjugated antibodies acting as a first binding partner. Alternatively, the beads 4311a coupled to streptavidin, and the antibody may be provided together, such that the first binding partner is provided in a complex including the bead 4311a, the streptavidin 4345, the biotin 4344, and the antibody 4312a, wherein the streptavidin and the biotin are bound (indicated at 4343). In these examples, the plurality of beads may be used in a one-bead or two-bead assay, wherein each bead 4311a of the plurality of beads is associated with a protein such as biotin or streptavidin, and wherein the protein such as biotin or streptavidin is bound to a known binding partner (such as the examples shown in FIG. 43A-43B), and thus associated with the antibody acting as the first binding partner 4312a for the one-bead or two-bead assay.

In some variations, the antibody of interest secreted by a cell may be an IgG or other immunoglobulin (e.g., IgA, IgD, IgE, IgM, etc.).

In some variations, the reagents used in the one-bead and two-bead assays may include MES sodium salt, Tris, NaCl, Tween-20, and BSA, and various combinations thereof.

Exemplary Sample Preparations

An exemplary method of preparing a sample for use in a one-bead clustering assay system may be carried out as follows. As an example, and as previously described, the first plurality of particles may comprise beads. Preparation of the beads as the first plurality of particles may include coupling the beads with an antibody and normalizing the bead concentration. First, the process may include aliquoting the beads into a low-bind tube, pelleting the beads and removing the supernatant. Next, the beads may be washed with a buffer, such as MES hemisodium salt, and the beads may next be resuspended in fresh buffer. Several bead resuspensions may be prepared in this manner. EDAC (a water-soluble carbodiimide derivative) may be used at room temperature to make a 20× MES buffer with EDAC solution. The resulting EDAC solution may be added to each bead resuspension, which may then be gently mixed and incubated at room temperature with rotation. Next, the beads may be pelleted by centrifugation, washed with MES buffer, resuspended in fresh buffer and the antibody, and incubated. After incubation for approximately one and a half hours, blocking buffer may be added. Next, repeated washing and incubation steps may be carried out to complete the antibody-coupling process. Finally, the beads may be washed and resuspended in a storage buffer, at which stage the antibody-coupled beads may be stored at 4° C. for future use.

Next, to obtain beads having an appropriate, normalized concentration for use in the one-bead clustering assay, the beads may be normalized by measuring their absorbance as a representation of the concentration. For example, Nanodrop's OD600 function may be used to obtain the absorbance. A concentration standard such as a commercially available mouse IgG beads standard, may be used for obtaining the beads concentration. The beads may be mixed by vortexing, measured using the Nanodrop for example, and spun down, and next diluted or concentrated to a desired concentration.

The step of providing a population of cells, including at least one cell of interest (3421), may include preparation of a cell sample and creating a cell dilution. This process may include counting the cells suspension in the sample and checking for cell viability, and next washing the cells with ice cold media twice and resuspending the cells with fresh ice cold media to a working concentration. The working concentration may be, for example, $4.4 \times 10^6$ cells per ml. A working cell concentration may then be made from this final cell concentration. For example, a 20-fold dilution may be performed to obtain the cell dilution, having a working cell concentration of $2.2 \times 10^5$ cells per ml.

Combining the population of cells, the first plurality of particles and the encapsulation reagent may be performed by first mixing together the population of cells (which may be provided as a cell dilution, prepared as described above) and the first plurality of particles (which may be provided as antibody-coupled beads, prepared as described as above), for example. A volume of the beads suspended in aqueous media such as a buffer as described above may be mixed with an equal volume of the cell dilution. For example 30 µl of beads coupled with the polyclonal antibody (such as IgG) may be combined with 30 µl of the cell dilution. The mixing of the cell dilution and the beads may be performed by repeated gentle pipetting, with a stirrer (e.g., magnetic stirrer), or the like.

Next, the encapsulation reagent may be added to the mixed cell dilution and antibody-coupled beads, to obtain the mixture for use in creating an emulsion. The encapsulation reagent may include a surfactant, which may be a fluorosurfactant, for example. Examples of components of the surfactant may include fluorine and polyethylene glycol (PEG), and further exemplary formulations are presented in Tables 1-3 below. The emulsion may be obtained by agitating the mixture, which may be performed by vortexing. The resulting emulsion may comprise sample entities within which the cells and beads are contained. The sample entities may be polydisperse sample entities, such as PODS, as described herein. Thus, the agitating step (3423) may result in PODS such as the POD 3218c shown as an example in FIG. 32A.

The emulsion may be incubated in a fresh tube (for example, a 15 ml conical tube) with the encapsulation reagent, loosely capped in a cell incubator at 37° C. with 5% $CO_2$ for a predetermined length of time. The predetermined length of time may be between about 1 hour to about 6 hours. After incubation, the emulsion may then be analyzed, such that a cell of interest can be selected from the population of cells. For example, the emulsion may be loaded into a chamber as described herein to read and analyze the PODS. The emulsion may also be visually observed using, for example, a suitable objective system or the lenless imager system as described above.

An exemplary method of preparing a sample for use in a two-bead clustering assay may be similar to that described above with respect to the method of preparing a sample for a one-bead clustering assay system, shown in FIG. 34A, except as described below.

The first plurality of particles and the second plurality of particles may comprise batches of beads. The first plurality of particles may be incubated with the antigen, and the second plurality of particles may be incubated with monoclonal antibodies, as in the method described above. Each batch of beads for the two-bead assay may next be normalized to a desired concentration as described, and a cell dilution may also be prepared as previously described. As an example, when creating the mixture, about 15 µl of the antibody-coupled beads may be mixed with about 15 µl of the antigen-coupled beads, to obtain a 30 µl bead volume. The 30 µl of beads, comprising the first and second pluralities of particles, may then be combined with an equal volume of the cell dilution.

Performing a Clustering Assay

Figure 35A:
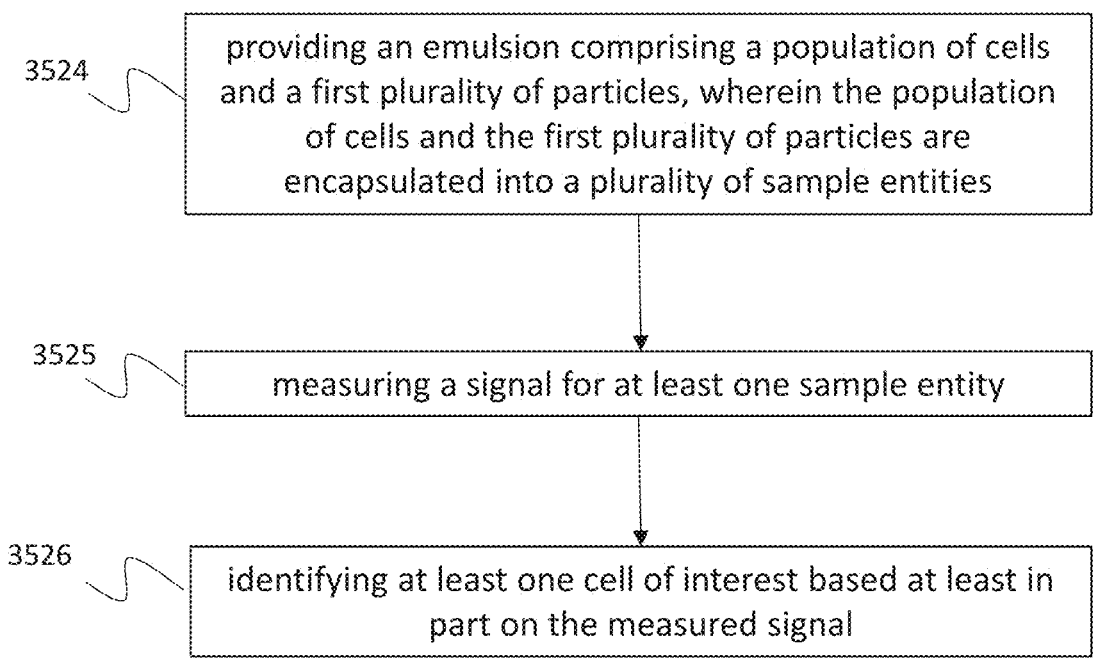
FIG. 35A depicts an exemplary method of selecting at least one cell of interest from a population of cells for use in a one-bead assay.
Figure 35B:
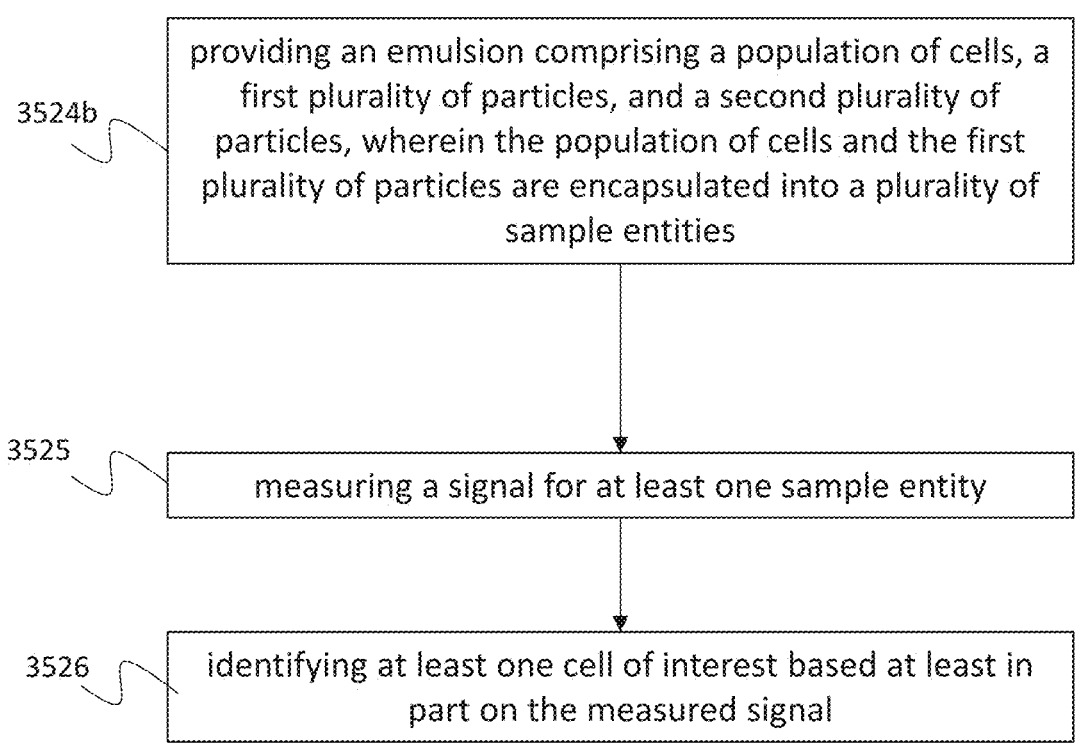
FIG. 35B depicts an exemplary method of selecting at least one cell of interest from a population of cells for use in a two-bead assay.

FIGS. 35A and 35B depict exemplary variations of methods of performing a clustering assay. FIG. 35A depicts an exemplary method of selecting at least one cell of interest from a population of cells for use in a one-bead assay. As an example, at least one cell of interest may be selected from a population of cells using the following exemplary method. The method may include providing an emulsion comprising a population of cells and a first plurality of particles (3524), which may be an emulsion prepared according to the method described when referencing FIG. 34A. Next, the method may include measuring a signal for at least one sample entity wherein the signal is at least partially associated with binding of the first and second binding partners (3525), and identifying the at least one cell of interest based at least in part on the measured signal (3526), to perform a one-bead assay.

The first plurality of particles may be provided suspended in aqueous media, and each particle of the first plurality of particles may comprise a first binding partner that is specific to a second binding partner secreted by the at least one cell of interest. The first binding partner may, for example, be a polyclonal antibody (as described with reference to FIG. 32B). The second binding partner may be a binding domain of the antibody secreted by the cell of interest (as described with reference to FIG. 32B). The particles, cell sample, and encapsulation reagent may be provided in an emulsion, which may be incubated in order to analyze for a signal. A signal may then be measured (3525) based on a binding interaction that occurs between the first and second binding partners, which may result in a detectable cluster. The cluster may be visualized using a lensless imager such as that described herein, or a microscope objective, for example. The cluster may allow for the identification of the at least one cell of interest (3526), and may allow for the selection of a POD containing the at least one cell of interest. For example, one or more PODs containing the at least one cell of interest may be sorted using the systems and methods (e.g., electromerging, sorting) such as those described above. The assay may thus enable the selection of a POD containing the at least one cell of interest for further processing of the cell of interest.

FIG. 35B depicts an exemplary method of selecting at least one cell of interest from a population of cells for use in a two-bead assay. The method may include providing an emulsion comprising a population of cells, a first plurality of particles, and a second plurality of particles (3524b), which may be an emulsion prepared according to the method described when referencing FIG. 34B. Next, the method may include measuring a signal for at least one sample entity wherein the signal is at least partially associated with binding of the first and second binding partners and binding of the third and fourth binding partners (3525), and identifying the at least one cell of interest based at least in part on the measured signal (3526), to perform a two-bead assay.

The first plurality of particles and the second plurality of particles may be provided suspended in aqueous media, and each particle of the first plurality of particles may comprise a first binding partner that is specific to a second binding partner secreted by the at least one cell of interest. The first binding partner may, for example, be an antigen (as described with reference to FIG. 33C). The second binding partner may be a binding domain of the antibody secreted by the cell of interest (as described with reference to FIG. 33C). Each particle of the second plurality of particles may comprise a third binding partner that is specific to a fourth binding partner secreted by the cell of interest. The third binding partner may, for example, be a monoclonal antibody (as described with reference to FIG. 33C). The fourth binding partner may, for example, be a binding domain of the antibody secreted by the cell of interest (as described with reference to FIG. 33C). The particles, cell sample, and encapsulation reagent may be provided in an emulsion, which may be incubated in order to analyze for a signal. A signal may then be measured (3525) based on a binding interaction that occurs between the first and second binding partners, which may result in a detectable cluster. The cluster may be visualized using a lensless imager such as that described herein, or a microscope objective, for example. The cluster may allow for the identification of the at least one cell of interest (3526), and may allow for the selection of a POD containing the at least one cell of interest. For example, one or more PODs containing the at least one cell of interest may be sorted using the systems and methods (e.g., electromerging, sorting) such as those described above. The assay may thus enable the selection of a POD containing the at least one c ell of interest for further processing of the cell of interest.

In some variations, the population of cells and the first plurality of particles are encapsulated into a plurality of polydisperse sample entities, and each particle of the first plurality of particles is suspended in aqueous media and comprises a first binding partner that is specific to a second binding partner secreted by the at least one cell of interest.

In some variations, the method may further include providing a second plurality of particles. The second plurality of particles may also be encapsulated into the polydisperse sample entities with the first plurality of particles. Each particle of the second plurality of particles may comprise a third binding partner that is specific to a fourth binding partner secreted by the at least one cell of interest (3527).

Exemplary Applications

FIG. 12 shows examples of various research and/or diagnostic applications for the systems and methods described herein. In some variations, the assay system may perform protein-based assays to detect various proteins. For example, the system may be used to detect markers such as Immunoglobulin G (IgG), alpha-fetoprotein (AFP), cancer antigens (e.g., CA125, CA 15-3), carbohydrate antigen (e.g., CA 19-9), carcinoembryonic gonadotropin (e.g., hCG or beta-hCG), prostate-specific antigen (PSA), and the like (e.g., for immunology-related research), Lactate Dehydrogenase (LDH) (e.g., to assess tissue damage such as cardiac stress and/or assess cancer, etc.), Beta 2 Microglobulin (B2M) (e.g., to help detect cancer), cytokines such as TNFα, IL-1, IL-2, IL-10, IL-12, type I interferons (e.g., IFN-α, IFN-β), IFN-γ, chemokines, and the like (e.g., to assess inflammation), and streptavidin (e.g., to assess biotinylation etc), and the. The systems described herein may also perform cell-based detection assays. For example, the assay system may be used to detect white blood cells (e.g., using anti-CD45 markers, such as for assessing leukemia and/or cancer metastasis), red blood cells (e.g., for hemotology), and yeast cells (e.g., for characterizing expression vectors), etc. The assay system may also be used to perform expression-based assays. For example, the assay system may be used to detect expression of hybridomas, B-cells, and phage display, etc., such as for drug target identification.

Example 1

Figure 13A:
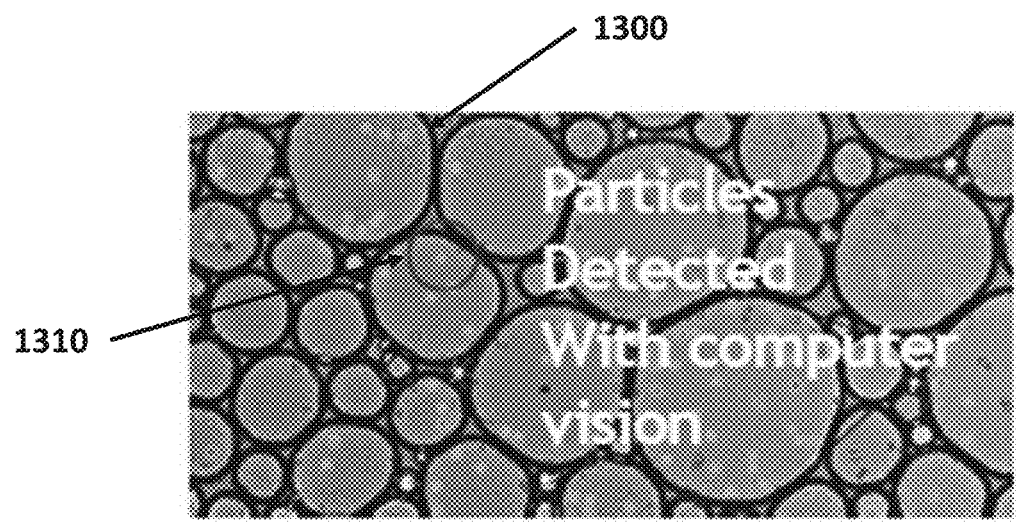
FIG. 13A provides an exemplary image of computer vision techniques to detect PODS and beads in PODS.
Figure 13B:
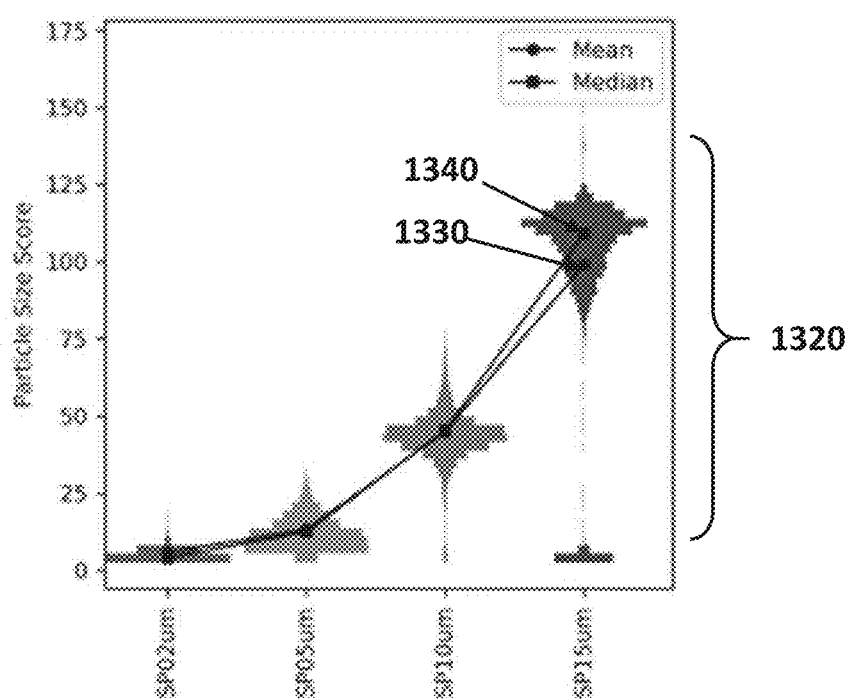
FIG. 13B is an illustrative graph of distributions of detected particle size scores from samples including various-sized beads.

The system described herein was used to detect and differentiate between microspheres of multiple sizes. For example, FIG. 13A is an annotated image of micron bead particles (1310) encapsulated in PODS (1300) detected using computer vision. Samples containing 2 μm, 5 μm, 10 μm, and 15 μm glass beads were combined with an encapsulation reagent to encapsulate the sample into PODS. Each sample, containing PODS with micron beads of a specific size, was introduced into the imaging chamber of the assay system. The lensless image sensors generated shadow images of the sample as it flowed through the chamber. The images were analyzed in order to detect the boundaries of the PODS (1300), and the micron beads (1310). In addition to identifying the PODS and micron beads, the computer vision system measured the relative sizes of the micron beads within the PODS to generate a particle size score (PSS) (e.g., as described below with respect to Examples 2-5). FIG. 13B is a graph of the distribution, the mean, and the median particle size scores generated for each sample containing micron beads of a known size. FIG. 13B shows, for example, the distribution of the particle size scores (1320) measured by the system in the sample containing 15 μm beads, and denotes the mean (1330), and median (1340) of the particle score size. The distribution, the mean, and the median particle size scores measured by the system are plotted for each of the 2 μm, 5 μm, 10 μm and 15 μm bead samples. Accordingly, the system may differentiate between 2 μm, 5 μm, 10 μm, and 15 μm beads. The ability to differentiate within the 2-15 μm size range may give the system the ability to perform various assays, such as those based on detection of protein and/or cell masses within a POD.

Example 2

Figure 14A:
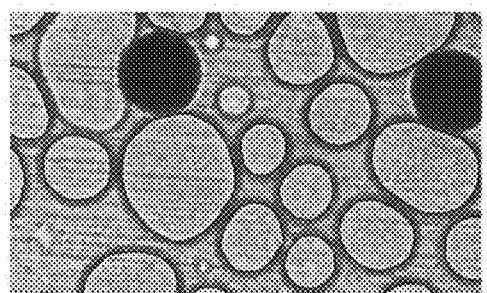
FIGS. 14A-14C provide exemplary images of computer vision techniques for detecting PODS and protein agglutinates in samples containing three different protein concentrations.
Figure 14B:
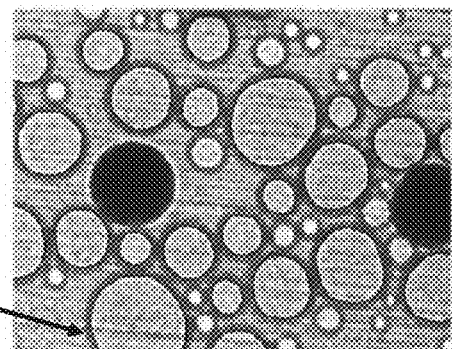
Figure 14C:
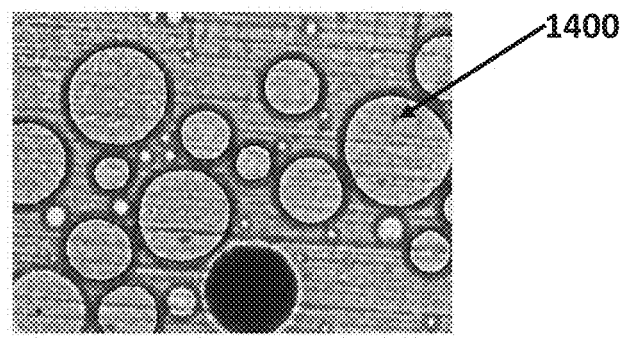

The system described herein were applied to perform quantitative protein assays, for example, to quantify the concentration of IgG in a sample. For example, FIGS. 14A-14C are images showing computer vision detection of IgG proteins (1400) in PODS (1410) at various concentrations. To perform a quantitative protein assay of IgG, multiple samples, each including a particular concentration of Rabbit IgG, were combined with antigen-conjugated to 1-2 micron latex beads specific to Rabbit IgG. As shown in FIG. 15D, approximately 1 million PODS were generated from each of seven samples, wherein each sample contained a different IgG concentration ranging from 0 ng/mL to 480 ng/mL. Each IgG and antibody-conjugated bead mixture sample was vortexed with fluorocarbon oil to encapsulate the proteins into PODS. The binding of the antibodies to the IgG proteins resulted in agglutination of IgG, and the formation of IgG protein masses ("agglutinates") in the PODS. The PODS were then introduced into the imaging chamber of the assay system. As the PODS passed through the chamber, the lensless image sensors generated shadow images of the sample. Approximately 1 million PODS were analyzed in less than 10 minutes at each concentration. The images were analyzed to detect the protein masses within the PODS, and various parameters of the PODS and agglutinates were measured from the images, such as the size and shape of the PODS, and the grayscale values of the agglutinates. The agglutinates present as darker on the shadow images, allowing detection of agglutinates in the PODS.

Figure 15A:
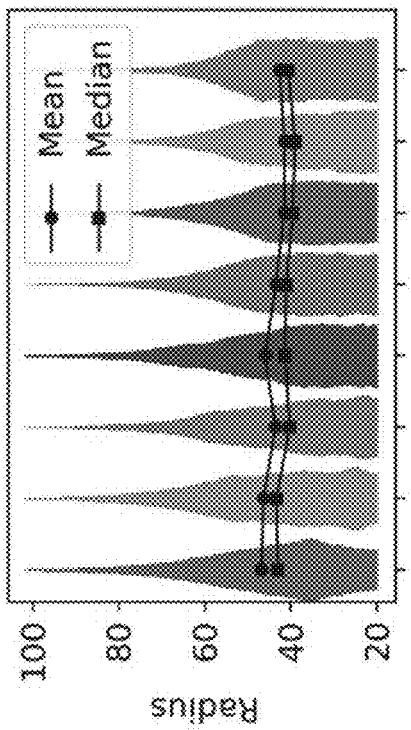
FIGS. 15A-15C are illustrative graphs of the distribution of multiple parameters of PODS at various protein concentrations detected using computer vision techniques.
Figure 15B:
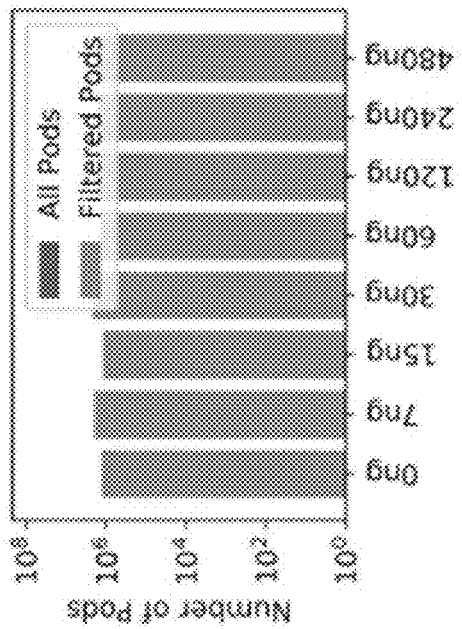
Figure 15C:
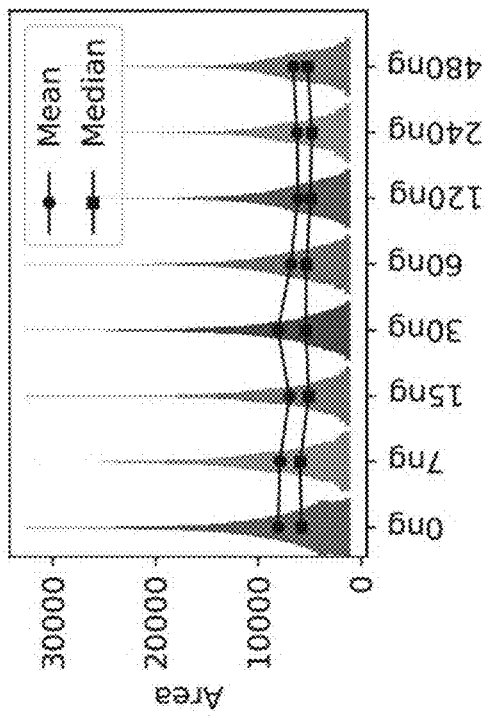
Figure 15D:
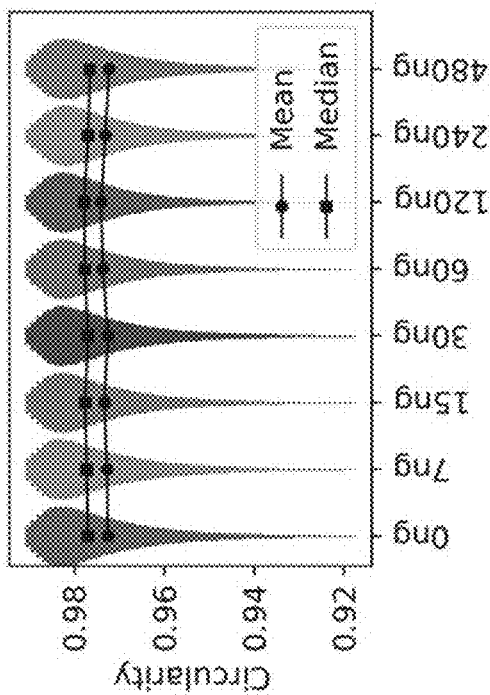
FIG. 15D is an illustrative bar graph showing the number of POD detected at each protein concentration.

For example, FIGS. 15A-15C depict POD parameters of POD area, POD radius, and POD circularity that were detected using computer vision techniques for multiple tested concentrations of IgG. FIG. 15A shows the distribution, the mean, and the median area of the PODS for each of the tested concentrations of IgG. FIG. 15B shows the distribution, mean, and median radius of the detected PODS in each tested concentration. FIG. 15C shows the distribution, mean, and median of the circularity values of the detected PODS in each tested concentration.

Figure 15E:
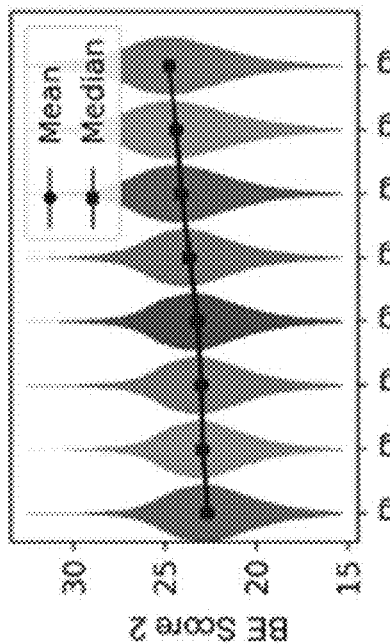
FIGS. 15E-15H are illustrative graphs of the distribution of BE scores, which are calculated using one or more parameters of agglutinates within the PODS and/or POD characteristics, at various protein concentrations.
Figure 15F:
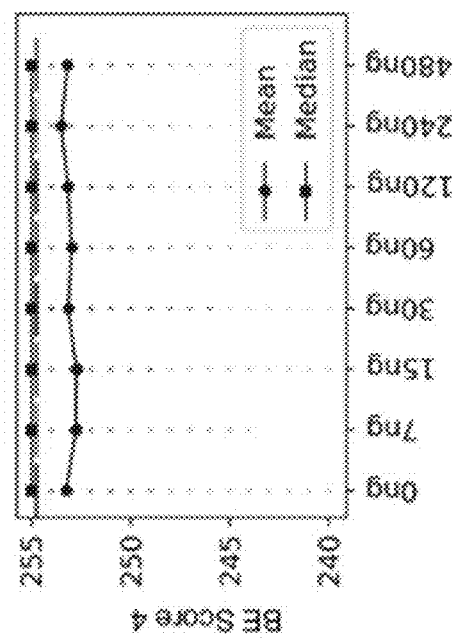
Figure 15G:
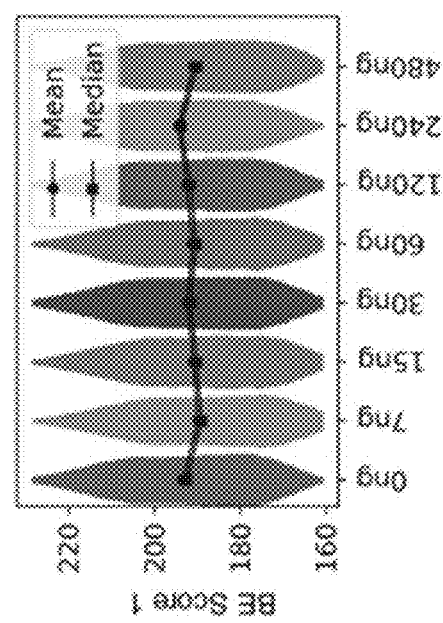
Figure 15H:
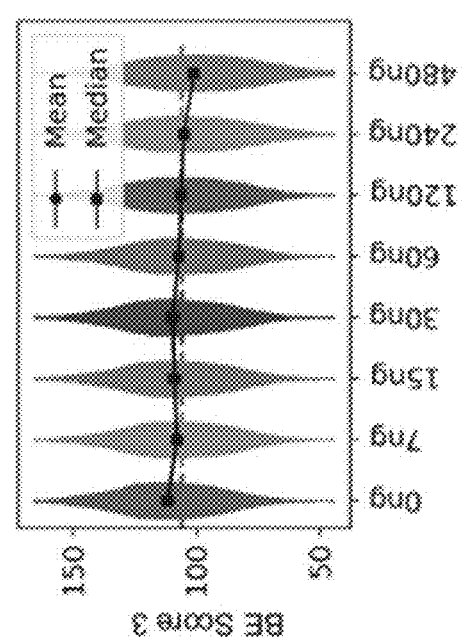
Figures 16A, 16B:
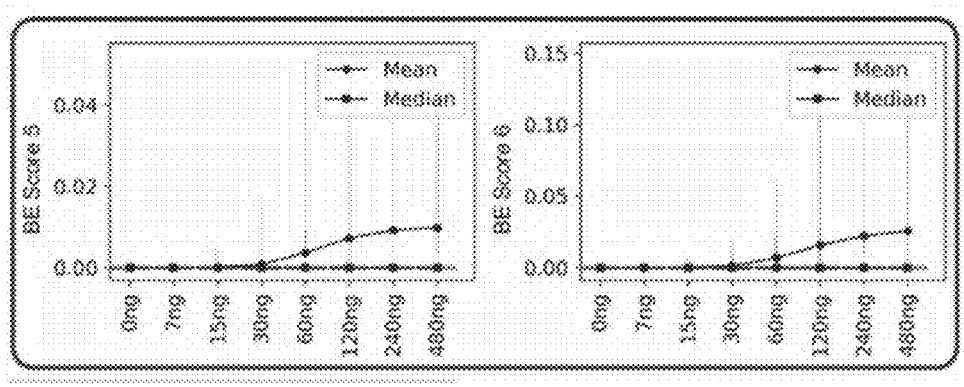
FIGS. 16A-16D are illustrative graphs of mean and median of various BE scores that have been correlated with protein concentration.
Figures 16C, 16D:
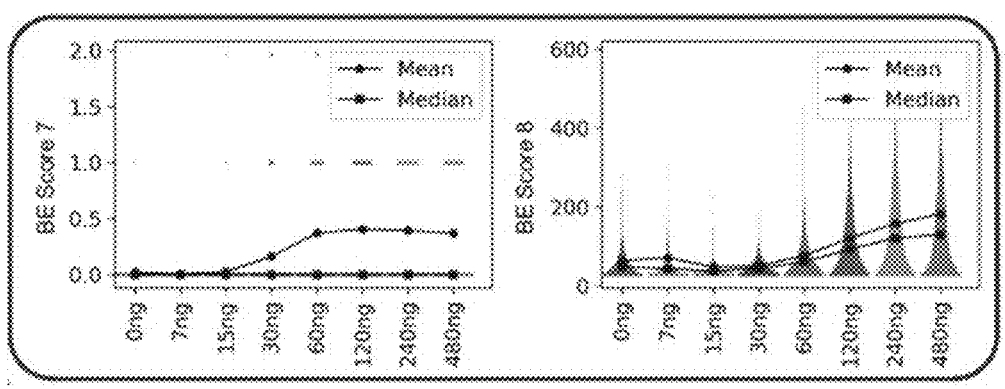

Various POD parameter scores ("BE scores") were derived from one or more measured parameters of the PODS and/or the features of interest in the PODS, such as sizes of aggregates, cells, particles, and/or changes in those aggregates, cells, and/or particles within the PODS. For example, FIGS. 15E-15H illustrate examples of BE scores derived from a singular POD parameter that can be detected from the images of the samples generated by the lensless image sensors. FIG. 15E shows the distribution, mean and median of BE Score 1, a measurement of the mean grayscale value of the detected aggregates within each POD at each concentration. FIG. 15F shows the distribution, mean and median of BE Score 2, a measurement of the grayscale standard deviation of the detected aggregates within the PODS at each tested concentration. FIG. 15G shows the distribution, mean, and median BE Score 3, a measurement of the grayscale minimum of the detected aggregates within the PODS at each tested concentration. FIG. 15H shows the distribution, mean and median BE Score 4, a measurement of the grayscale maximum of the detected aggregates within the PODS, at each tested concentration.

Furthermore, various POD parameter scores were derived as composite scores from multiple measured parameters of the PODS and/or the features of interest (e.g., aggregates, cells, other particles, etc.) within the PODS. Composite POD parameter scores may provide information (e.g., trends in correlation with IgG concentration) that are not otherwise available from POD parameter scores that are derived on a single measured parameter. For example, FIGS. 16A-16D illustrate examples of BE scores calculated from a combination of multiple measured POD characteristics and/or BE scores that are derived from a singular POD parameter. A total of 11 BE scores were calculated from the images of the tested IgG samples described above, four of which were used to correlate image characteristics to IgG concentration, as depicted in FIGS. 16A-16D. BE Score 5 (shown in FIG. 16A) is generally a measure of agglutination, based on a binary black and white image (e.g., objects in the POD depicted as white, and background pixels are black, or vice versa). For example, BE Score 5 was based on a ratio of object pixels to background pixels, scaled to (e.g., divided by) POD area. BE Score 6 (shown in FIG. 16B) is generally another measure of agglutination, based on a distance transform of a binary black and white image such as that described above, where BE Score 6 was based on the pixel values of the resulting grayscale image, scaled to POD area. BE Score 7 (shown in FIG. 16C) is generally a particle count score based on the number of detected separate objects in the POD. BE Score 8 (shown in FIG. 16D) is generally a particle size score, which relates to the average area of all the objects identified in an imaged POD. Generally, BE Scores 5-8 were found to increase with increased IgG concentration within a detection range for the experiment. As depicted in FIGS. 16A-16D, the detection range for IgG based on the BE scores was between about 30 and about 480 ng/mL. The graphs in FIGS. 16A-16D demonstrate that, within the IgG detection range, each of BE Scores 5-8 may be correlated with IgG concentration. Mathematical algorithms applied to BE Scores 5-8 were used to assess the concentration of the IgG in each sample. Thus, because the size of the protein masses within the PODS generally increases with protein concentration, the ability of the platform to measure the size of the protein masses at the 2-15 µm level from the images of the PODS may allow the platform to quantitate the protein concentration using characteristics derived from images generated by lensless image sensors (e.g., based on empirical and/or calculated models correlating one or more BE Scores to concentration, comparing one or more BE Scores to one or more predetermined thresholds, etc.)

These results demonstrate that the parameters of PODS and agglutinates measured from the shadow images of a sample may be used to quantitate protein concentration in the samples based on a combination of one or more BE scores such as those described above. Thus, the assay system described herein may be used to perform protein-based assays to quantify the concentration of protein in a sample using antibody-conjugated beads quickly and without the use of fluorescent labels.

Example 3

Figure 17A:
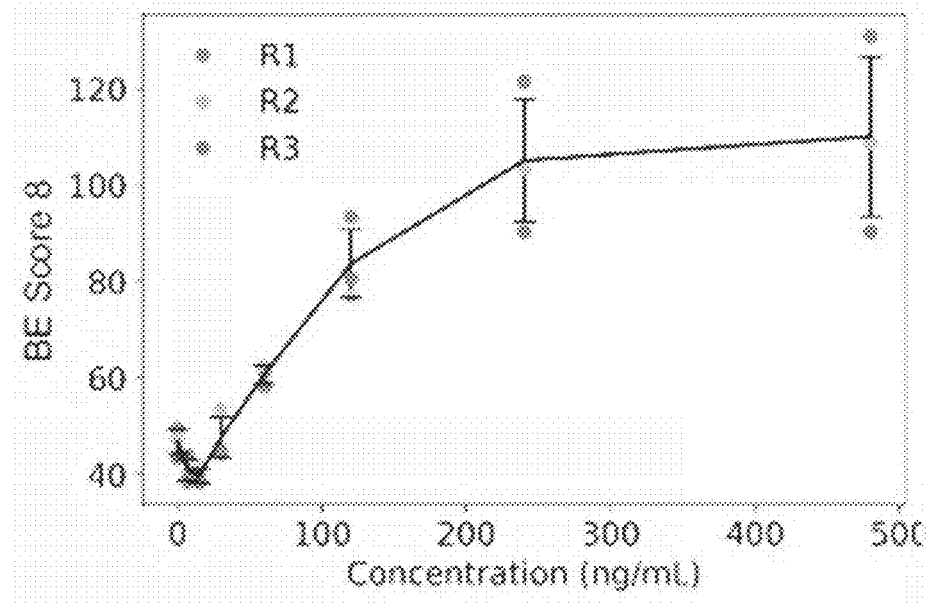
FIGS. 17A and 17B are illustrative graphs of BE scores related to the precision of protein-based assays at various protein concentrations.
Figure 17B:
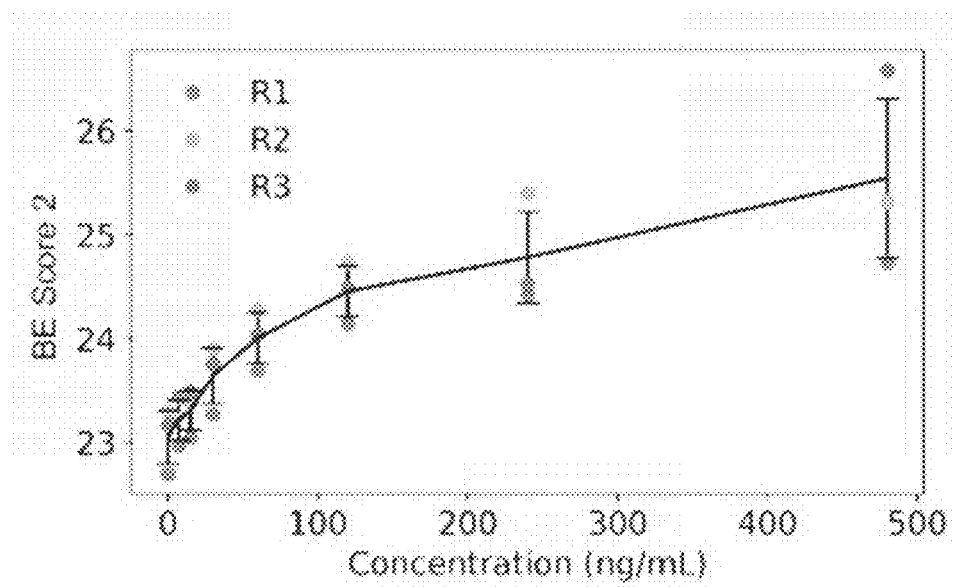

An inter-assay precision analysis was performed in a bead-mediated IgG assay using the system described herein. The inter-assay precision analysis enabled assessment of reproducibility and consistency of the assay systems described herein, as well as evaluation of sensitivity of the assay over different IgG concentrations. This information was used to calculate margin of error at different protein concentrations. For example, an inter-assay precision analysis was performed by testing three replicates (R1, R2, R3) of each IgG concentration used in the above-described IgG assay. FIG. 17A depicts the ranges of BE Score 8, a measurement of median particle size scores, in each of the three replicates at each tested concentration. FIG. 17B depicts the ranges of BE Score 2, a measurement of median grayscale standard deviation of the detected aggregates within the PODS, in each of three replicates at each tested concentration. As demonstrated by FIGS. 17A and 17B, different levels of the IgG concentration exhibited different levels of precision by which these two parameters may be measured. For example, FIGS. 17A and 17B demonstrate that for at least some BE Scores, sensitivity of the assay system varies with concentration of the detected analyte, at different segments of the detected range. For example, FIGS. 17A and 17B suggest that the precision of the particle size score median and grayscale standard division median measurements generally decreases as IgG concentration increases (the range of the values increases with increased concentration).

Example 4

Figure 18A:
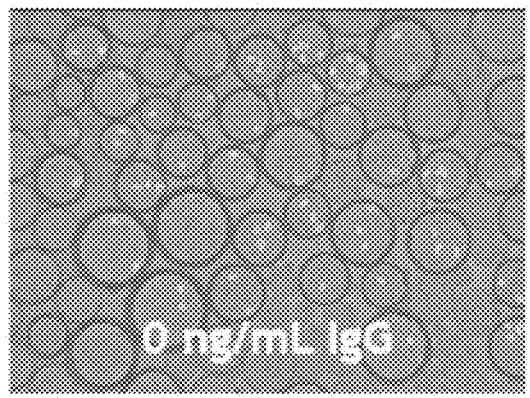
FIG. 18A provides an exemplary image of computer vision detection of PODS containing a control sample.
Figure 18B:
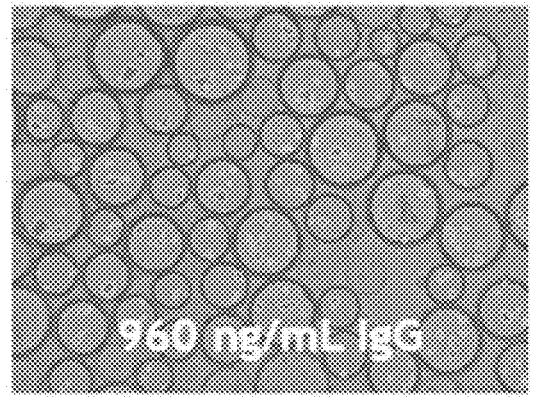
FIG. 18B provides an exemplary image of computer vision detection of PODS containing bovine serum and a sample of 960 ng/mL rabbit IgG.

The system described herein was used to test a rabbit IgG assay to determine if bovine serum interfered with the specificity of the assay. A control sample and an experimental sample were separately analyzed with the assay system. The control sample included 500-fold diluted bovine serum. The control sample was then introduced into the imaging chamber of the system, and the lensless image sensors generated shadow images of PODS including the control sample (FIG. 18A). The experimental sample was prepared by mixing 960 ng/mL rabbit IgG serum with 500-fold diluted bovine serum and antibody-conjugated beads specific to IgG, and combined with encapsulation reagent (e.g., surfactant) to encapsulate the IgG proteins into PODS. The experimental rabbit IgG sample was introduced into the imaging chamber of the system, and the lensless image sensors generated shadow images of PODS including the experimental sample (FIG. 18B).

Figure 18C:
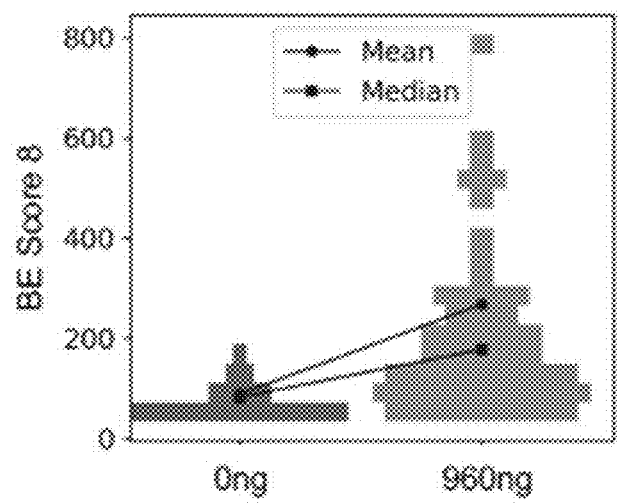
FIG. 18C is an illustrative graph comparing the distribution of a POD parameter score in the control and the 960 ng/mL samples.

FIG. 18C depicts the distribution, mean, and median of BE Score 8 (particle size score, as described above with respect to FIG. 16D), for the control and experimental samples. The difference in the distribution, mean and median of BE Score 8 between the control sample and the experimental sample demonstrated that rabbit IgG does not show significant cross-species reactivity with bovine serum. In other words, this example suggests that bovine serum may not interfere with the specificity of the assay.

Example 5

Figure 19A:
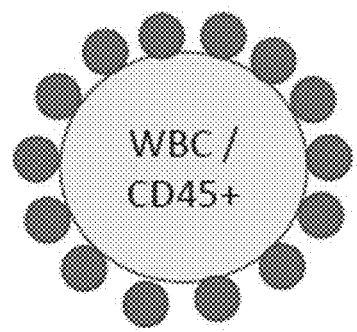
FIG. 19A depicts an illustrative schematic of a CD-45+ cell tagged with anti-CD45 nanoparticles.
Figure 19B:
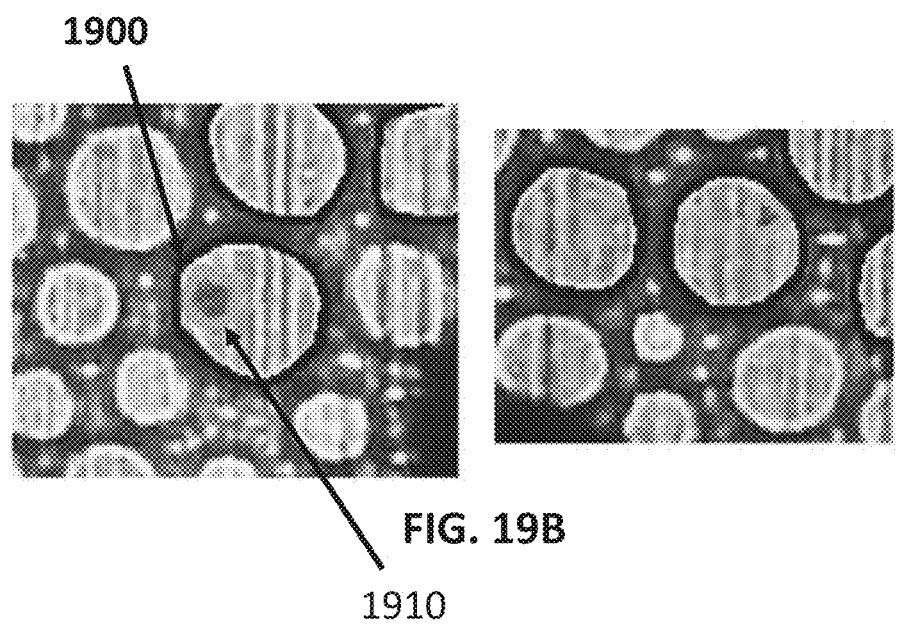
FIG. 19B provides two exemplary images of computer vision detection of PODS containing CD-45+ cells tagged as shown in FIG. 19A.

The system described herein was successfully used in cell-based detection assays (e.g., cell type and cell count assays). For example, the assay system described herein was used to detect the presence of leukocytes in a sample, as illustrative of other cell-based detection assays. As shown in the schematic illustration of FIG. 19A, a CD-45+ leukocyte (white blood cell) was tagged or "decorated" with anti-CD45 nanoparticles (e.g., glass beads). To identify the presence of CD-45+ leukocytes in a sample, the sample containing CD-45 cells was mixed with anti-CD45 nanoparticles. The nanoparticles selectively bound to the unique surface markers on the CD-45 cells, which provided the means to differentiate the CD-45 cells from other cells. The sample including the CD-45 cells bound to nanoparticles was mixed with an encapsulation reagent and vortexed to encapsulate the CD-45 cells into PODS. The binding of the anti-CD45 nanoparticles to the CD-45 cells resulted in agglutination of the CD-45 cells, and the formation of CD-45 agglutinates in the PODS. The PODS were then introduced into the imaging chamber of the device, and the lensless image sensors generated shadow images of the PODS as they passed through the chamber. The computer vision system analyzed the images of the PODS (FIG. 19B) to detect the presence of the CD-45 cells based on the increased greyscale values of the CD-45 agglutinates. The CD-45 cell agglutinates (1910) in the PODS (1900) present as darker in the shadow image compared to other cells, which allows for detection and enumeration of the CD-45 cells by the computer vision system. The use of the assay system to identify nanoparticle-tagged CD-45 cells demonstrates that the system may perform cell detection and enumeration based on selective binding of nanoparticles to cell surface markers. It may be inferred that the system may also be used to perform detection and enumeration of various cells that exhibit surface markers.

Example 6

Figure 20A:
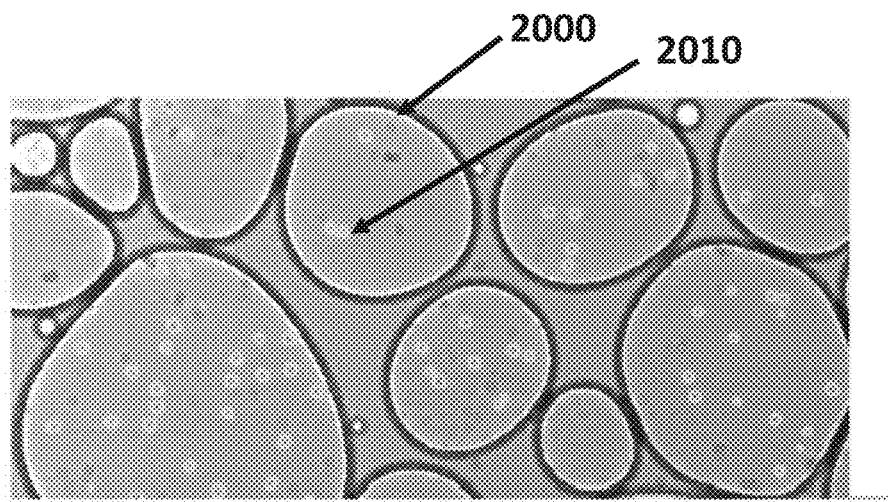
FIG. 20A provides an exemplary image of computer vision detection of PODS containing yeast cells stained with trypan blue.
Figure 20B:
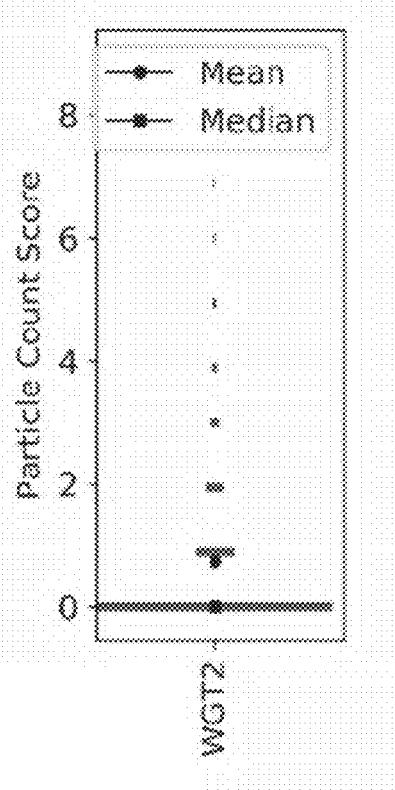
FIG. 20B is an illustrative graph of the particle count scores of yeast cells detected by computer vision.
Figure 20C:
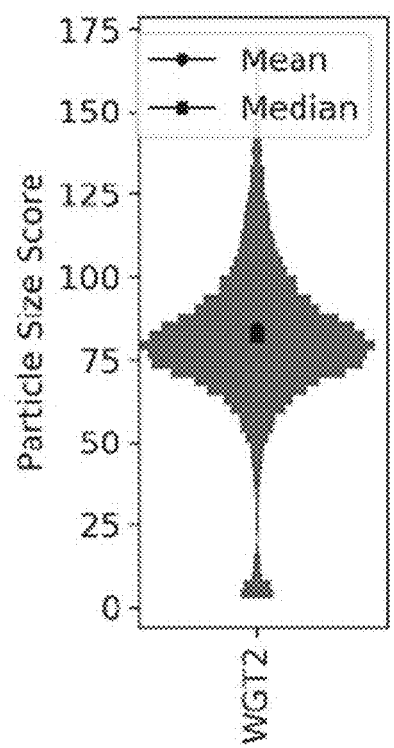
FIG. 20C is an illustrative graph of the distribution of the particle size scores of the yeast cells detected by computer vision.

The system described herein can also be used to quickly and efficiently distinguish between dead and live cells in a sample. For example, the assay system described herein was used to detect and/or enumerate dead yeast cells. FIG. 20A depicts computer vision detection of PODS (2000) containing dead yeast cells (2010). To perform a dead-cell count assay, yeast cells were stained with trypan blue, and encapsulated with a reagent into PODS. The sample of PODS containing the stained yeast cells was introduced into the imaging chamber of the assay system, and the imaging system generated shadow images of the PODS as they passed through the chamber. The computer vision system identified the dead yeast cells in the shadow images, based on the fact that the dead yeast cells absorbed more of the blue dye due to their increased porosity compared to live cells. The stained yeast cells present as darker in the shadow image, allowing the computer vision system to identify the color-saturated dead yeast cells based on a decreased grayscale value. The computer vision system analyzed the images to provide a dead cell particle count score as shown in FIG. 20B, and a particle size score, as shown in FIG. 20C. The ability of the assay system to provide a dead cell count and size score of dead yeast cells demonstrates that the system may detect, enumerate, and/or measure dead cells based on the use of cell staining techniques. This ability may be extrapolated to perform enumeration of various cells types using differentiation of cells based on staining. Furthermore, after distinguishing between live and dead cells, live and dead cells may be sorted using fluidic systems as described herein (e.g., to dispense cells of interest into a suitable vessel such as a wellplate for further analysis and/or culturing).

Example 7

Figure 22:
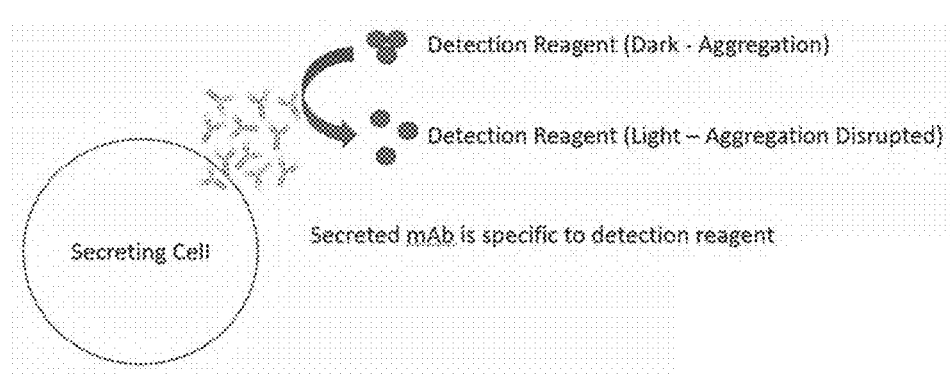
FIG. 22 depicts an illustrative schematic of another method for processing samples in a cell secretion assay.

Additionally or alternatively, a method for processing a sample may include detecting one or more cell secretions in a sample (or the cells themselves). For example, generally, in a cell secretion assay, one or multiple analytes (e.g., a protein of interest such as a cytokine or a monoclonal antibody (mAb)) may be secreted by one or more cells, and it may be desirable to determine which analyte(s) are secreted. With reference to FIG. 22, a sample including secreting cells and at least one detection reagent may be dispersed into PODS and passed through an assay system as described above to produce shadow images of the PODS. The one or more analytes of interest that are secreted from the cells may be specific to a detection reagent, such that the resulting aggregation results in a darkened, shadowed mass that is detectable in the shadow image. Thus, identification of an aggregated mass in a POD may indicate that one or more analytes of interest has been secreted from the cells. Multiple analytes (e.g., specific to different reagents mixed with the sample) may furthermore be identifiable in parallel using the assay system.

Example 8

Hybridoma cells may be produced by injecting a specific antigen into a mouse, collecting antibody-producing B-cells from the mouse, and fusing the B-cells with tumor cells to make them "immortal." It is valuable to identify and collect hybridoma cells that produce a significant amount of the desired antibody. For example, hybridoma cells that produce a significant amount of IgG antibodies (Ab), where the IgG Ab are specific and have high affinity and/or specificity to certain antigens, are valuable cells to identify and collect for therapeutic purposes. However, conventional protocols for screening such high secretor hybridoma cells are costly and time-consuming, as the hybridoma cells must be replicated and multiplied over a number of days under a carefully controlled environment.

Figure 27:
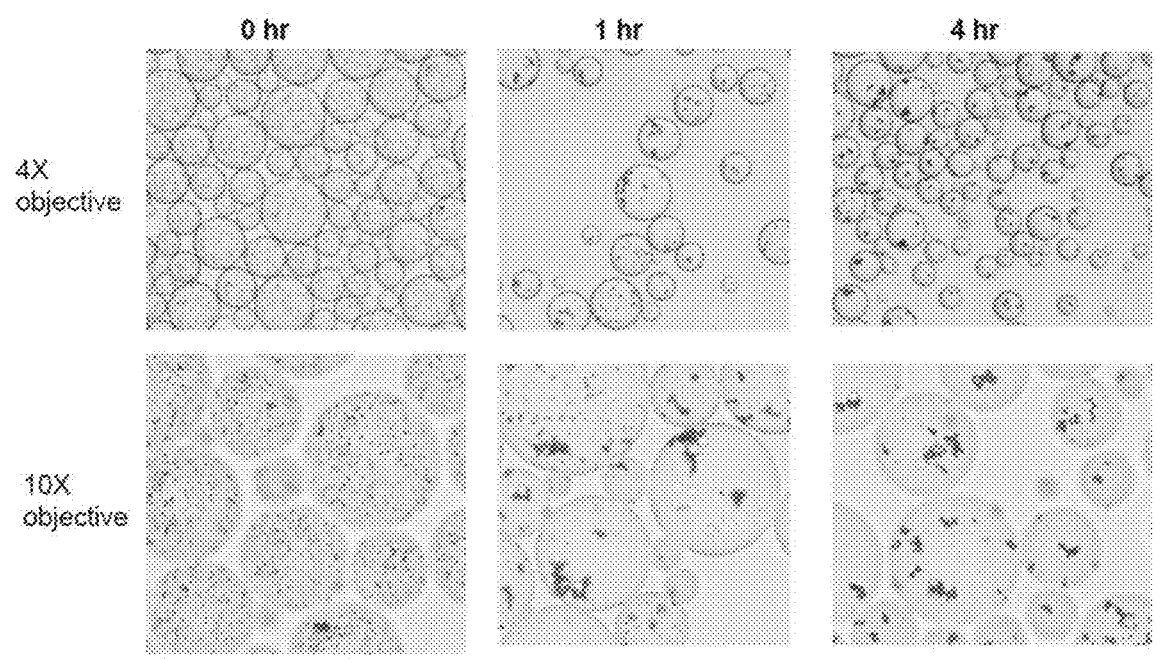
FIG. 27 depicts images illustrating detection of agglutination in an exemplary experiment to assess hybridoma secretion ranges after various incubation periods.

In one example, a method for processing a sample using a chamber and imager array system, such as that described herein, may be used to identify hybridoma cells that are high secretors or producers of antibodies for specific targets. A sample was prepared by vortexing hybridoma cells (mouse cells) with anti-mouse IgG pAb coupled 1 µm polystyrene beads, along with a carrier oil with surfactant, to form an emulsion including PODS, where each of the PODS were loaded with more than one cell (such that average number of cells per POD $\lambda$>1). The sample was imaged using a chamber and imager array system described above at t=0, t=1 hour (after 1 hour incubation), and t=4 hours (after 4 hours incubation). As shown in these images (FIG. 27, at both 4× objective and 10× objective magnification), large clusters in the PODS were observable after only 1 hour, and further observable after 4 hours. Thus, the images of FIG. 27 suggest that hybridoma cells secrete IgG in a detectable range within PODS even after a brief incubation period of only 1 hour, such that hybridoma cells with a sufficiently strong biosignal (e.g., manifested as identifiable clumping in images) may be identified in PODS. In some variations, such high secretor hybridoma cells may further be sorted and collected as an output with a high concentration of high secretor hybridoma cells.

Example 9

FIG. 29A is a table of exemplary system parameters for an exemplary variation of an electromerging chamber arrangement and exemplary sample with PODS. The exemplary sample included a mixture of (i) the indicated volume of aqueous cell media with approximately 10 million B cells and (ii) the indicated volume of carrier oil with surfactant, leading to the composition outlined in FIG. 29A, including approximately 154 million total PODS having the indicated POD characteristics. Some of the PODS in the sample were smaller than the 35 µm chamber gap spacing, and were be spherical (not flattened into an oblate shape) when in the chamber. Due to the shape of these PODS, it would be more difficult to detect the cells contained in them, and may cause cells of interest to be inadvertently lost or discarded.

Figure 29B:
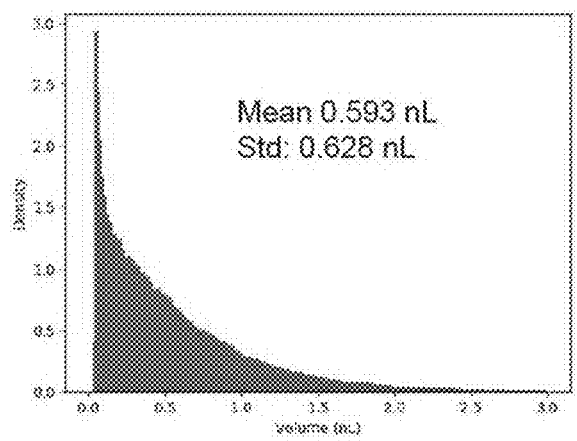
FIGS. 29B and 29C are an actual distribution and a modeled distribution, respectively, of POD sizes in the sample described in FIG. 29A.
Figure 29C:
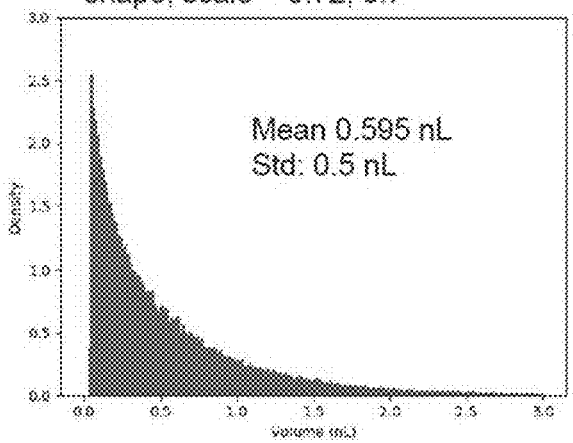

Probabilistic modeling was performed to estimate the number of cells that are not detected by an electromerging chamber arrangement. The distribution of actual POD diameters for the sample is shown in FIG. 29B, and may be modeled closely as a Gamma distribution (FIG. 29C). Using probabilistic modeling in view of the average POD characteristics indicated in FIG. 29A, the expected percentage of "small" PODS (that is, smaller than 35 µm and having a volume of less than 22 pL) that would be overlooked, but are not actually empty, is about 0.017%. In other words, assuming 1 cell maximum per overlooked POD, processing the sample in the chamber would result in potentially failing to detect approximately 170 cells per million PODS, or about 2615 cells total. Given a total B cell population in the original sample of 15.4 million, this means potentially failing to detect about 0.017% of the cells in the sample. Thus, the analysis with respect to the sample and system associated with FIGS. 29A-29C suggests that only a negligible proportion of cells may be inadvertently undetected using the chamber described herein.

Example 10

As described above, a one-bead and/or two-bead clustering assay as described herein may be performed to identify a particular cell of interest within a population of cells. The cell of interest may be a high secretor of a target analyte, such as an antibody, or may be a high secretor of a target analyte having a high affinity for an antigen. Experimental tests were performed to demonstrate that B cells and CHO cells can generate a measurable and detectable signal in PODS within a specified time frame using the one-bead or two-bead assays described herein.

Figure 36A:
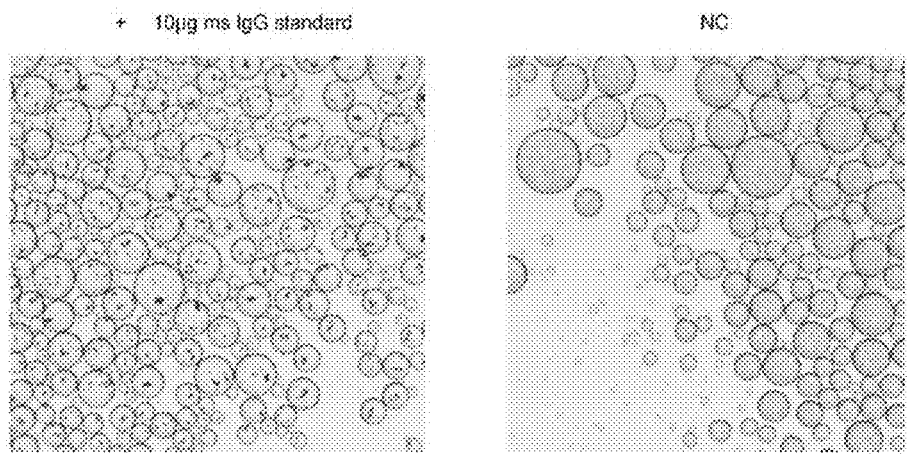
FIGS. 36A-36C depict 4× objective microscope cell images from tests of a one-bead assay. To demonstrate the one-bead assay, one batch of anti-mouse IgG polyclonal (pAb) beads (FIG. 36A) and two batches of anti-human IgG pAb beads (FIGS. 36B-36C) were prepared for performing a one-bead assay.
Figure 36B:
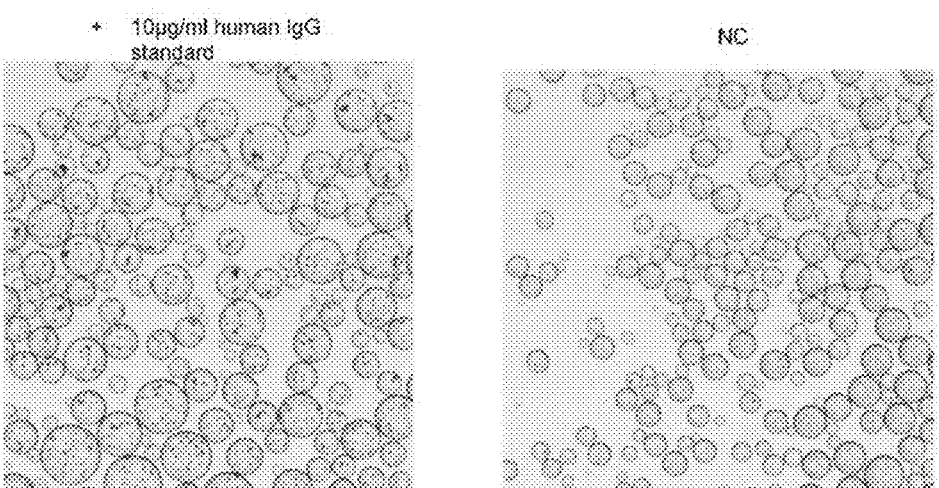
Figure 36C:
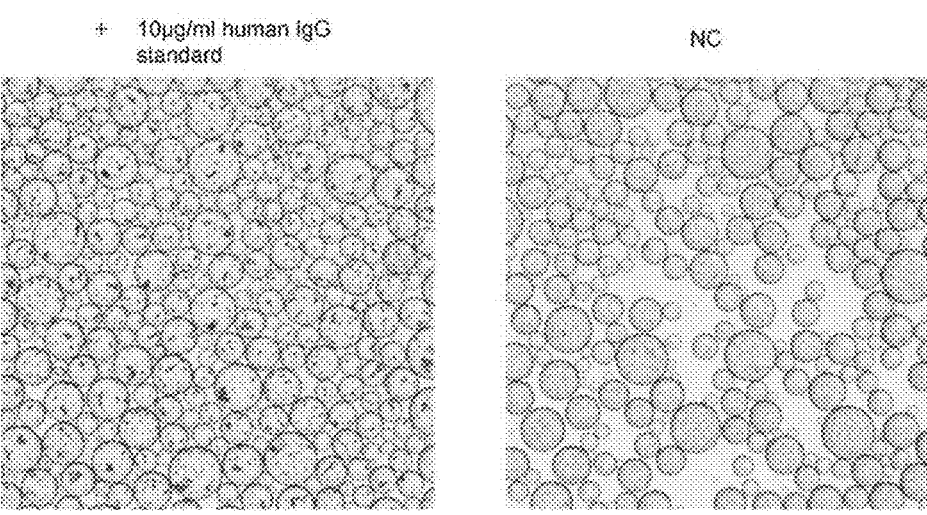

FIGS. 36A-36C depict 4× objective microscope cell images from tests of a one-bead assay. To demonstrate the one-bead assay, one batch of anti-mouse IgG polyclonal (pAb) beads (FIG. 36A) and two batches of anti-human IgG pAb beads (FIGS. 36B-36C) were prepared for performing a one-bead assay. FIGS. 36A-36C show that all batches of beads showed clustering when 10 µg/ml of mouse or human IgG were present. Each batch is shown against a no cell (NC) control.

Figure 37:
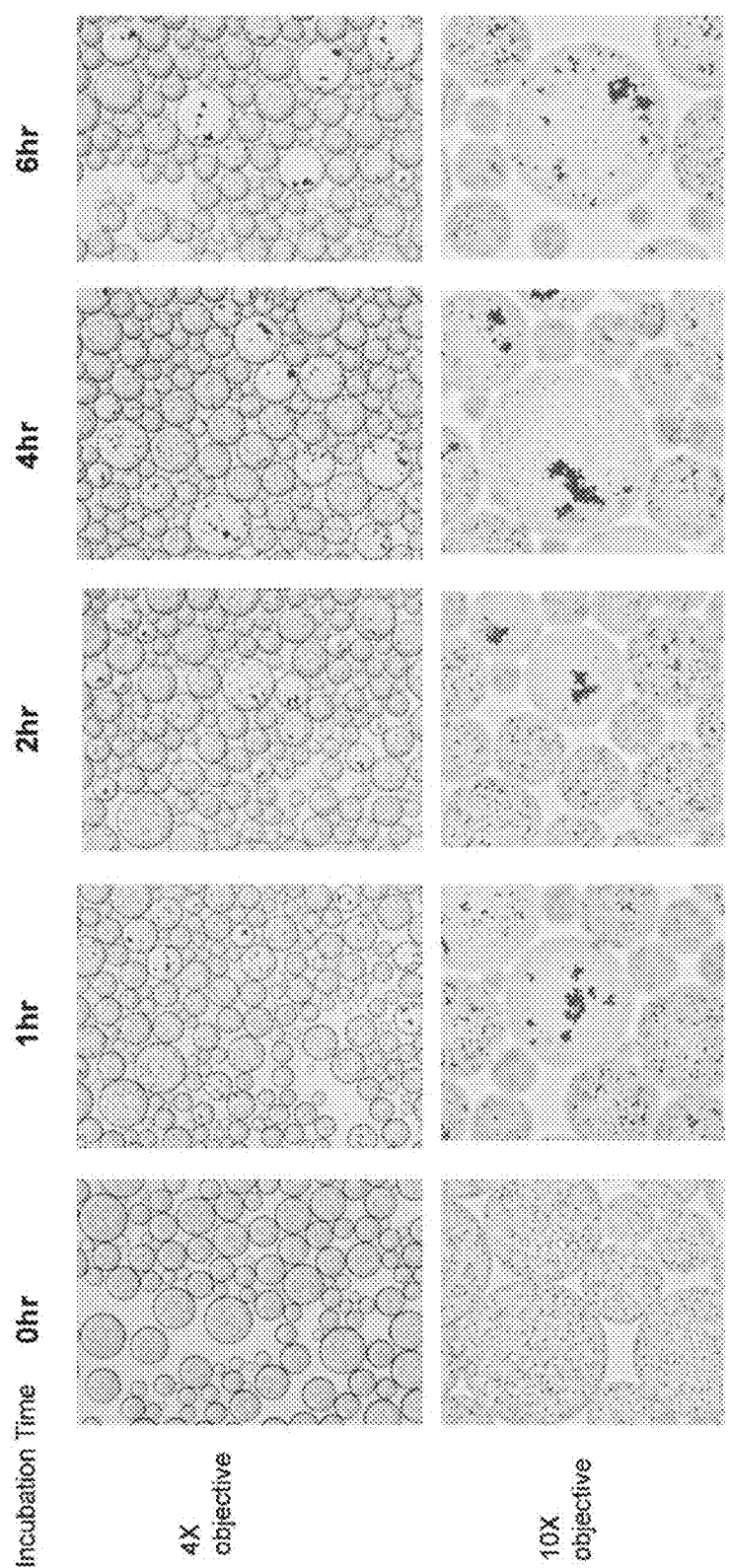
FIG. 37 depicts images from tests performed using a one-bead assay as described herein, used to assess mouse IgG secreting single hybridoma cells in PODS.

FIG. 37 depicts images from tests performed using a one-bead assay as described herein, used to assess mouse IgG secreting single hybridoma cells in PODS. Microscope images at both 4× and 10× objectives are shown at time=0, t=1 hour, t=2 hours, t=4 hours, and t=6 hours after incubation. The images show clustering at all time points beginning from t=1 hour.

Figure 38:
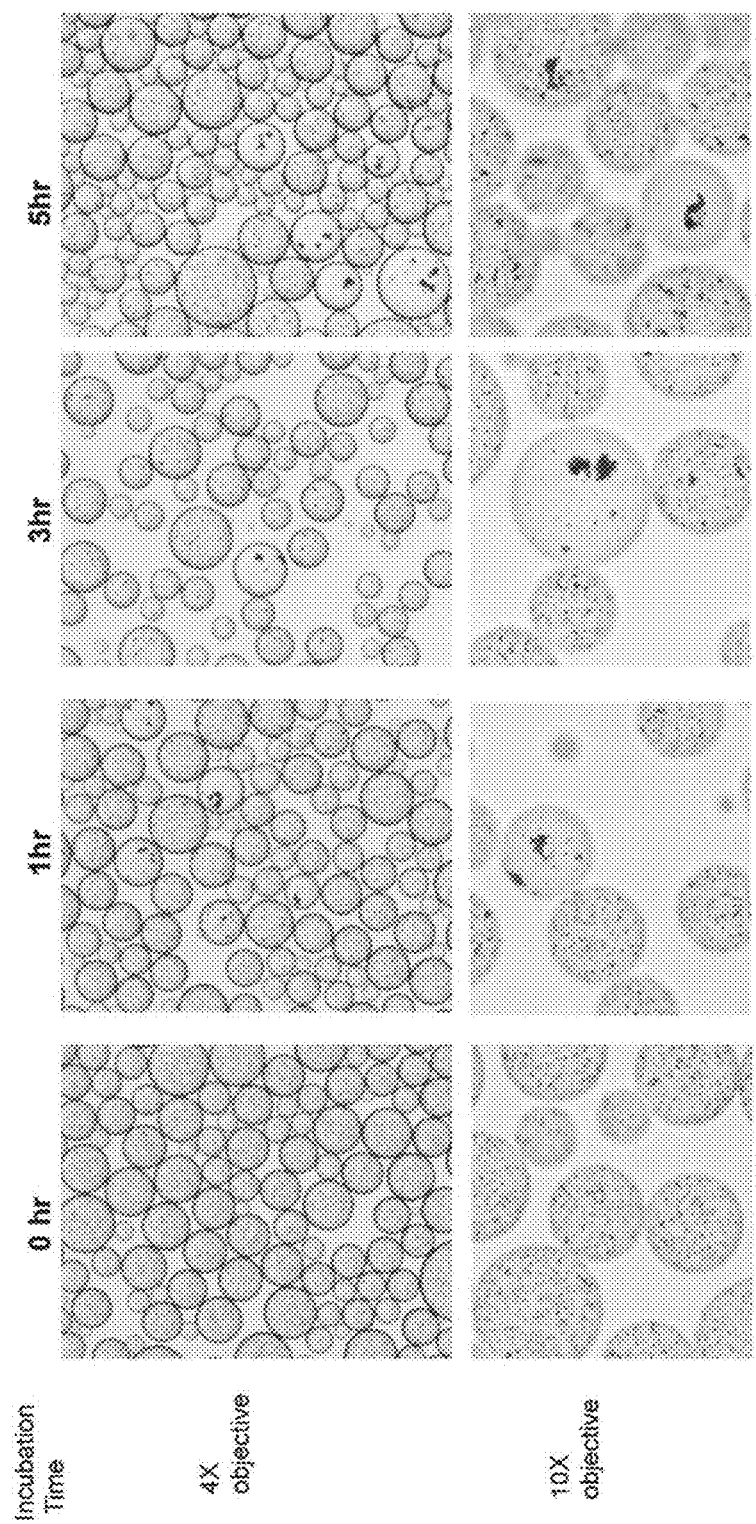
FIG. 38 depicts images from tests performed using a two-bead assay as described herein, used to assess antigen-specific antibody secreting single hybridoma cells in PODS.

FIG. 38 depicts images from tests performed using a two-bead assay as described herein, used to assess antigen-specific antibody secreting single hybridoma cells in PODS. Bovine IgM antigen specific antibodies were analyzed in the tests. Microscope images at both 4× and 10× objectives are shown at time=0, t=1 hour, t=3 hours, and t=5 hours after incubation. The images show clustering at all time points beginning from t=1 hour.

Tests were performed to check for non-specific background clustering using a cell line that secretes antibodies that are not against the specific antigen. Hybridoma cells that secrete anti-bovine insulin (HB-123 cell line) were used as a control in a bovine IgM antigen two-bead assay. Bovine IgM antigen beads were used. The CRL-1894 cell line was also used to test for specific clustering, with the CRL-1894 cells being known to secrete the anti-bovine IgM monoclonal antibody). 0.005% trypan blue was added to monitor cell viability throughout the tests.

Figure 39A:
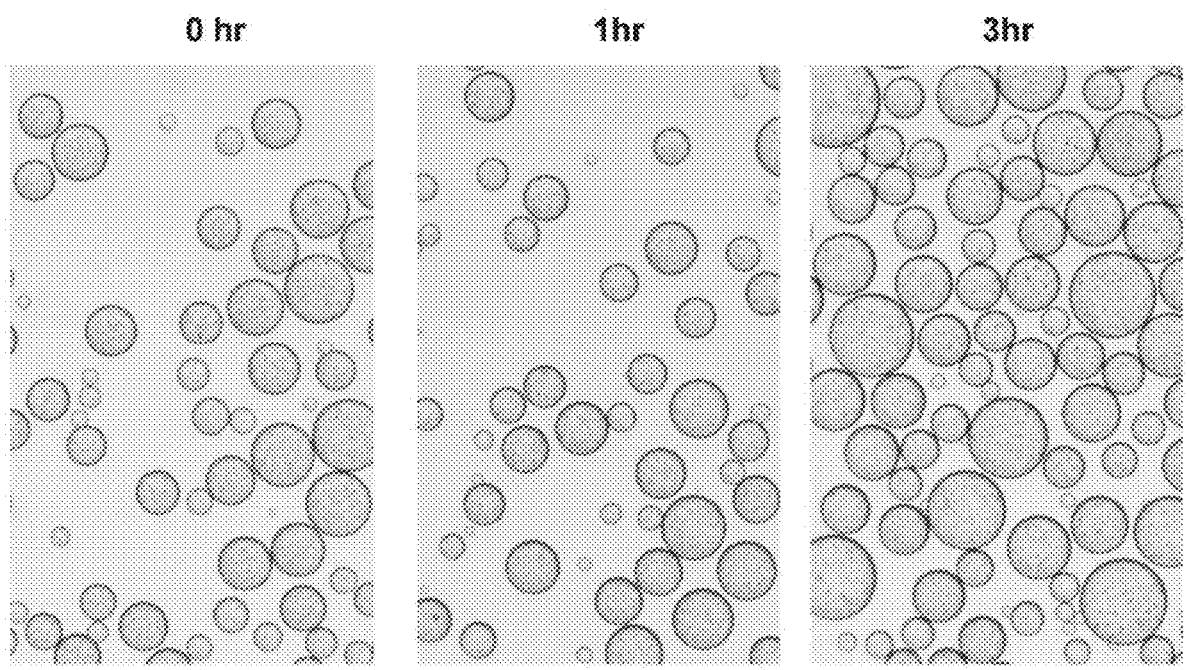
FIG. 39A depicts 4× objective microscope images from the tests conducted using the HB-123 cell line, wherein no clustering was expected.

FIG. 39A depicts 4× objective microscope images from the tests conducted using the HB-123 cell line, wherein no clustering was expected. The images show that at time=0, t=1 hour, and t=3 hours, no background clustering occurred. In contrast, FIGS. 39B-39D show 10× objective microscope images at time=0, t=1 hour, and t=3 hours, showing that clustering occurred starting from t=1 hour. The cell viability was measured to be about 84%.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to explain the principles of the invention and its practical applications, they thereby enable others skilled in the art to utilize the invention and various embodiments with various modifications as are suited to the particular use contemplated. It is intended that the following claims and their equivalents define the scope of the invention.

The invention claimed is:

1. A mixture comprising:
   an encapsulation reagent;
   one or more first particles suspended in aqueous media, each first particle comprising a first binding partner; and
   a population of cells, comprising at least one cell of interest that secretes a protein of interest having a second binding partner, wherein the first binding partner is specific to the second binding partner.

2. A method of preparing a sample for a clustering assay system, the method comprising:
   providing a population of cells, the population of cells comprising at least one cell of interest;
   combining the population of cells, a first plurality of particles, and an encapsulation reagent to create a mixture, wherein each particle of the first plurality of particles is suspended in aqueous media and comprises a first binding partner that is specific to a second binding partner secreted by the at least one cell of interest; and
   agitating the mixture to create an emulsion, thereby encapsulating the population of cells into a plurality of polydisperse sample entities.

3. A method of selecting at least one cell of interest from a population of cells, the method comprising:
   providing an emulsion comprising the population of cells and a first plurality of particles, wherein the population of cells and the first plurality of particles are encapsulated into a plurality of polydisperse sample entities, and wherein each particle of the first plurality of particles is suspended in aqueous media and comprises a first binding partner that is specific to a second binding partner secreted by the at least one cell of interest;
   measuring a signal for at least one sample entity, wherein the signal is at least partially associated with binding of the first and second binding partners; and identifying the at least one cell of interest based at least in part on the measured signal.

4. The method of claim 3, wherein the second binding partner is coupled to a first component of a protein of interest secreted by the at least one cell of interest, and wherein the measured signal quantifies the protein of interest in the at least one sample entity.

5. The method of claim 4, wherein identifying the at least one cell of interest comprises identifying at least a portion of the sample entities that has a measured signal greater than a predetermined threshold.

6. The method of claim 3, wherein measuring the signal for the at least one sample entity comprises receiving at least one shadow image of the at least one sample entity, and determining a size score of at least one object in the sample entity based on the at least one shadow image, wherein the measured signal is based at least in part on the size score.

7. The method of claim 3, the emulsion further comprising a second plurality of particles encapsulated into the plurality of polydisperse sample entities, wherein each particle of the second plurality of particles comprises a third binding partner that is specific to a fourth binding partner secreted by the at least one cell of interest, and wherein the signal is at least partially associated with a binding of the first and second binding partners, and at least partially associated with a binding of the third and fourth binding partners.

8. The method of claim 7, wherein the second binding partner and the fourth binding partner are associated with a protein of interest secreted by the at least one cell of interest, and wherein the measured signal quantifies binding affinity of the protein of interest to the first binding partner or the third binding partner.

9. The method of claim 3, further comprising the step of removing the at least one cell of interest from the polydisperse sample entities.

10. The method of claim 3, wherein the first plurality of particles comprise a second population of cells, and the first binding partner comprises antigens expressed on the second population of cells.

* * * * *